United States Patent
Tsao et al.

(10) Patent No.: US 11,796,535 B2
(45) Date of Patent: *Oct. 24, 2023

(54) METHODS AND SYSTEMS FOR MULTIPLEX ASSAYS

(71) Applicants: Plexbio Co., Ltd., Taipei (TW); Dean Tsao, Hillsborough, CA (US)

(72) Inventors: Dean Tsao, Hillsborough, CA (US); Chin-Shiou Huang, Santa Clara, CA (US); Yao-Kuang Chung, New Taipei (TW)

(73) Assignee: Plexbio Co., Ltd., Taipei (TW)

( * ) Notice: Subject to any disclaimer, the term of this patent is extended or adjusted under 35 U.S.C. 154(b) by 1227 days.

This patent is subject to a terminal disclaimer.

(21) Appl. No.: 16/332,271

(22) PCT Filed: Nov. 21, 2016

(86) PCT No.: PCT/US2016/063202
§ 371 (c)(1),
(2) Date: Mar. 11, 2019

(87) PCT Pub. No.: WO2018/052464
PCT Pub. Date: Mar. 22, 2018

(65) Prior Publication Data
US 2019/0369091 A1    Dec. 5, 2019

Related U.S. Application Data

(60) Provisional application No. 62/396,056, filed on Sep. 16, 2016.

(51) Int. Cl.
*G01N 33/543* (2006.01)
*G01N 33/545* (2006.01)
*C08L 63/00* (2006.01)

(52) U.S. Cl.
CPC ..... *G01N 33/54333* (2013.01); *G01N 33/545* (2013.01); *C08L 63/00* (2013.01)

(58) Field of Classification Search
CPC ........ B01J 2219/00459; B01J 2219/005; B01J 2219/00556; B01J 2219/00558; B01J 2219/0056; B01J 2219/00693; B01J 2219/00702; B01J 2219/00722; B01J 2219/00725; B01J 2219/0074; C08L 63/00; C40B 20/04; G01N 33/54333; G01N 33/545
See application file for complete search history.

(56) References Cited

U.S. PATENT DOCUMENTS

| | | |
|---|---|---|
| 4,677,045 A | 6/1987 | Champ et al. |
| 5,237,498 A | 8/1993 | Tenma et al. |
| 5,354,873 A | 10/1994 | Allen et al. |
| 5,492,795 A | 2/1996 | Allen et al. |
| 5,641,634 A | 6/1997 | Mandecki |
| 5,656,750 A | 8/1997 | Allen et al. |
| 5,795,981 A | 8/1998 | Lee et al. |
| 6,916,661 B2 | 7/2005 | Chandler et al. |
| 7,858,307 B2 | 12/2010 | Ho |
| 7,871,770 B2 | 1/2011 | Ho |
| 7,884,719 B2 | 2/2011 | Oberle |
| 8,148,139 B2 | 4/2012 | Ho |
| 8,232,092 B2 | 7/2012 | Ho et al. |
| 8,610,848 B2 | 12/2013 | Shim et al. |
| 8,697,334 B2 | 4/2014 | True et al. |
| 8,939,376 B1 | 1/2015 | De Smedt et al. |
| 8,967,483 B2 | 3/2015 | De Smedt et al. |
| 9,040,463 B2 | 5/2015 | Demierre et al. |
| 9,063,044 B2 | 6/2015 | Kao et al. |
| 9,255,922 B2 | 2/2016 | Ho et al. |
| 10,019,815 B2 | 7/2018 | Chung et al. |
| 10,302,640 B2 | 5/2019 | Tsao et al. |
| 10,436,776 B2 | 10/2019 | Chung et al. |
| 10,436,778 B2 * | 10/2019 | Tsao ................. C40B 40/04 |
| 10,859,910 B2 | 12/2020 | Tsao et al. |
| 10,894,975 B2 * | 1/2021 | Tsao ................. C12Q 1/6834 |
| 11,579,522 B2 * | 2/2023 | Tsao ................. G09G 3/3648 |
| 2002/0094116 A1 | 7/2002 | Frost et al. |
| 2002/0150909 A1 | 10/2002 | Stuelpnagel et al. |
| 2002/0155618 A1 | 10/2002 | O'Hagan |
| 2003/0134330 A1 | 7/2003 | Ravkin et al. |
| 2006/0097056 A1 | 5/2006 | De Smedt et al. |
| 2006/0205115 A1 | 9/2006 | Oberle |
| 2007/0148599 A1 | 6/2007 | True |
| 2007/0172823 A1 | 7/2007 | Steinberg et al. |
| 2007/0238140 A1 | 10/2007 | Pentoney et al. |

(Continued)

FOREIGN PATENT DOCUMENTS

| | | |
|---|---|---|
| CN | 1271410 C | 8/2006 |
| CN | 102246037 B | 5/2014 |

(Continued)

OTHER PUBLICATIONS

European search opinion for European Application No. 16 916 388.8 dated Mar. 30, 2020.*
Pelras et al. "Transparent Low Molecular Weight Poly(Ethylene Glycol) Diacrylate-Based Hydrogels as Film Media for Photoswitchable Drugs," Polymers, 2017, vol. 9, No. 12, 639, pp. 1-14.*
Arnason et al., "Morphology, Tumor Genetics, and Outcomes in Five Cases of Biliary Adenofibroma", Laboratory Investigation, vol. 94, Suppl. 1, 2014, p. 417A.
Bong et al., "Magnetic Barcoded Hydrogel Microparticles for Multiplexed Detection", Langmuir, vol. 26, No. 11, Jun. 2010, pp. 8008-8014.
Braeckmans et al., "Encoding Microcarriers: Present and Future Technologies", Nature Reviews Drug Discovery, vol. 1, Jun. 2002, pp. 447-456.

(Continued)

*Primary Examiner* — Galina M. Yakovleva
(74) *Attorney, Agent, or Firm* — MORRISON & FOERSTER LLP

(57) ABSTRACT

Disclosed herein are compositions comprising beads with unique analog code identifiers for storing information about a multiplex assay as well as methods for using the same in multiplex chemical and biological assays.

12 Claims, 25 Drawing Sheets

(56) References Cited

U.S. PATENT DOCUMENTS

| | | |
|---|---|---|
| 2008/0129455 A1 | 6/2008 | Oberle |
| 2008/0234144 A1 | 9/2008 | Ho et al. |
| 2009/0032592 A1 | 2/2009 | Christensen |
| 2009/0201504 A1 | 8/2009 | Ho et al. |
| 2010/0075438 A1 | 3/2010 | Ho et al. |
| 2010/0081215 A1 | 4/2010 | De geest et al. |
| 2010/0210477 A1 | 8/2010 | Ho |
| 2010/0246005 A1 | 9/2010 | Moon et al. |
| 2010/0248257 A1 | 9/2010 | Jacobsen et al. |
| 2011/0007955 A1 | 1/2011 | Ho et al. |
| 2012/0088691 A1 | 4/2012 | Chen et al. |
| 2012/0200950 A1 | 8/2012 | Shim et al. |
| 2013/0095574 A1 | 4/2013 | Demierre et al. |
| 2013/0302910 A1 | 11/2013 | Demierre |
| 2014/0242614 A1 | 8/2014 | Kao et al. |
| 2014/0274778 A1 | 9/2014 | Tsao et al. |
| 2015/0057190 A1 | 2/2015 | De Smedt et al. |
| 2015/0190803 A1 | 7/2015 | Demierre et al. |
| 2016/0178624 A1 | 6/2016 | Lesser |
| 2017/0146545 A1 | 5/2017 | Chung et al. |
| 2017/0160272 A1 | 6/2017 | Tsao et al. |
| 2017/0270690 A1 | 9/2017 | Chung et al. |
| 2018/0195113 A1 | 7/2018 | Tsao et al. |
| 2018/0201983 A1 | 7/2018 | Tsao et al. |
| 2019/0242884 A1 | 8/2019 | Tsao et al. |
| 2019/0265567 A1 | 8/2019 | Tsao et al. |

FOREIGN PATENT DOCUMENTS

| | | |
|---|---|---|
| CN | 105143886 A | 12/2015 |
| EP | 1173760 B1 | 6/2005 |
| EP | 2100143 A1 | 9/2009 |
| EP | 2179289 A1 | 4/2010 |
| EP | 2342561 A1 | 7/2011 |
| EP | 2367633 A1 | 9/2011 |
| EP | 2484447 A1 | 8/2012 |
| EP | 2673086 A1 | 12/2013 |
| EP | 2774997 A1 | 9/2014 |
| EP | 1903337 B1 | 7/2015 |
| JP | 2010536029 A | 11/2010 |
| JP | 2014504733 A | 2/2014 |
| WO | 1997/15390 A1 | 5/1997 |
| WO | 2000/63695 A1 | 10/2000 |
| WO | 2002/33419 A1 | 4/2002 |
| WO | 2002/057743 A2 | 7/2002 |
| WO | 2002/059603 A2 | 8/2002 |
| WO | WO-2004027378 A2 | 4/2004 |
| WO | WO-2007036905 A2 | 4/2007 |
| WO | 2008/034275 A1 | 3/2008 |
| WO | WO-2008116093 A2 | 9/2008 |
| WO | 2009/020506 A1 | 2/2009 |
| WO | WO-2009048530 A2 | 4/2009 |
| WO | 2009/128938 A1 | 10/2009 |
| WO | 2010/042745 A1 | 4/2010 |
| WO | 2010/072011 A1 | 7/2010 |
| WO | 2011/014879 A2 | 2/2011 |
| WO | 2011/156432 A2 | 12/2011 |
| WO | 2012/106827 A1 | 8/2012 |
| WO | WO-2013070990 A1 | 5/2013 |
| WO | 2014/031997 A1 | 2/2014 |
| WO | 2014/144016 A1 | 9/2014 |
| WO | 2016/198954 A1 | 12/2016 |

OTHER PUBLICATIONS

Derveaux et al., "Layer-by-Layer Coated Digitally Encoded Microcarriers for Quantification of Proteins in Serum and Plasma", Analytical Chemistry, Dec. 4, 2007, pp. 85-94.

Extended European Search Report (includes Supplementary European Search Report and European Search Opinion) received for European Patent Application No. 16806958.1, dated Sep. 25, 2018, 8 pages.

Final Office Action received for U.S. Appl. No. 14/208,481, dated May 5, 2017, 13 pages.

Friedman et al., "A Rapid Multiplex Mass Spectrometry Assay for Mutational Profiling of Colorectal Cancer", Laboratory Investigation, vol. 95, Suppl 1, 2015, pp. 514A.

Final Office Action received for U.S. Appl. No. 14/208,481, dated Apr. 26, 2018, 12 pages.

Final Office Action received for U.S. Appl. No. 15/374,930, dated Aug. 3, 2018, 23 pages.

International Preliminary Report on Patentability received for PCT Patent Application No. PCT/IB2016/000937, dated Dec. 21, 2017, 5 pages.

International Preliminary Report on Patentability received for PCT Patent Application No. PCT/US2014/028246, dated Sep. 24, 2015, 8 pages.

International Preliminary Report on Patentability received for PCT Patent Application No. PCT/US2016/063202, dated Mar. 28, 2019, 5 pages.

International Search Report and Written Opinion received for PCT Patent Application No. PCT/IB2016/000937, dated Oct. 27, 2016, 7 pages.

International Search Report and Written Opinion received for PCT Patent Application No. PCT/US2016/063202, dated Apr. 24, 2017, 8 pages.

International Search Report received for PCT Patent Application No. PCT/US2014/028246, dated Aug. 11, 2014, 4 pages.

International Written Opinion received for PCT Patent Application No. PCT/US2014/028246, dated Aug. 11, 2014, 6 pages.

Non-Final Office Action received for U.S. Appl. No. 14/208,481 dated Sep. 7, 2016, 10 pages.

Non-Final Office Action received for U.S. Appl. No. 14/208,481, dated Feb. 27, 2019, 13 pages.

Non-Final Office Action received for U.S. Appl. No. 14/208,481, dated Sep. 27, 2017, 11 pages.

Non-Final Office Action received for U.S. Appl. No. 15/374,930, dated Nov. 17, 2017, 23 pages.

Notice of Allowance received for U.S. Appl. No. 14/208,481, dated Jun. 26, 2019, 6 pages.

Notice of Allowance received for U.S. Appl. No. 15/374,930, dated Jan. 18, 2019, 17 pages.

Office Action received for Chinese Patent Application No. 201480010176.3, dated Mar. 2, 2018, 29 pages (20 pages of English Translation and 9 pages of Official Copy).

Restriction Requirement received for U.S. Appl. No. 15/374,930, dated Aug. 24, 2017, 10 pages.

Sukhanova et al., "Nanocrystal-Encoded Fluorescent Microbeads for Proteomics Antibody Profiling and Diagnostics of Autoimmune Diseases", Nano Letters, vol. 7, No. 8, 2007, pp. 2322-2327.

Tsao et al., Unpublished U.S. Appl. No. 16/386,087, filed Apr. 16, 2019, titled "Image Differentiated Multiplex Assays", (U.S. Patent Application is not submitted herewith pursuant to the waiver of 37 C.F.R. § 1,98(a)(2)(iii) issued by the Office on Sep. 21, 2004.).

Tsao et al., Unpublished U.S. Appl. No. 16/386,092, filed Apr. 16, 2019, titled "Image Differentiated Multiplex Assays", (U.S. Patent Application is not submitted herewith pursuant to the waiver of 37 C.F.R. § 1,98(a)(2)(iii) issued by the Office on Sep. 21, 2004.).

Voorham et al., "Comprehensive Mutation Analysis in Colorectal Flat Adenomas", PLOS One, vol. 7, No. 7, 2012, pp. 1-8.

Zhang et al., "Colorimetric Detection of Anthrax DNA with a Peptide Nucleic Acid Sandwich-Hybridization Assay", Journal of the American Chemical Society, vol. 129, No. 27, 2007, pp. 8424-8425.

Corrected Notice of Allowance received for U.S. Appl. No. 14/208,481, dated Aug. 19, 2019, 3 pages.

Law et al., "Squaraine Chemistry. Synthesis, Characterization, and Optical Properties of a Class of Novel Unsymmetrical Squaraines: [4-(Dimethylamino)phenyl](4'-Methoxyphenyl)squaraine and its Derivatives", The Journal of Organic Chemistry, vol. 57, No. 12, 1992, pp. 3278-3286.

Maahs et al., "Syntheses and Derivatives of Squaric Acid", Angewandte Chemie International Edition, vol. 5, No. 10, 1966, pp. 888-893.

(56) References Cited

OTHER PUBLICATIONS

Needels et al., "Generation and Screening of an Oligonucleotide-Encoded Synthetic Peptide Library", Proc. Natl. Acad. Sci., vol. 90, Nov. 1993, pp. 10700-10704.
Sprenger et al., "Cyclobutendiylium-Farbstoffe", Angewandte Chemie., vol. 80, No. 14, 1968, pp. 541-546 (English Abstract Submitted).
Sprenger et al., "Das Cyclobuten-diylium-Kation, ein neuartiger Chromophor aus Quadratsaure", Angew. Chem., vol. 79, No. 12, 1967, 2 pages (English Abstract Submitted).
Unpublished U.S. Appl. No. 17/758,511, internationally filed on Jan. 7, 2021 titled "Image Differentiated Multiplex Assays for Detection of Dna Mutations in Lung Cancer," (Copy not submitted herewith pursuant to the waiver of 37 C.F.R. § 1,98(a)(2)(iii)).

* cited by examiner

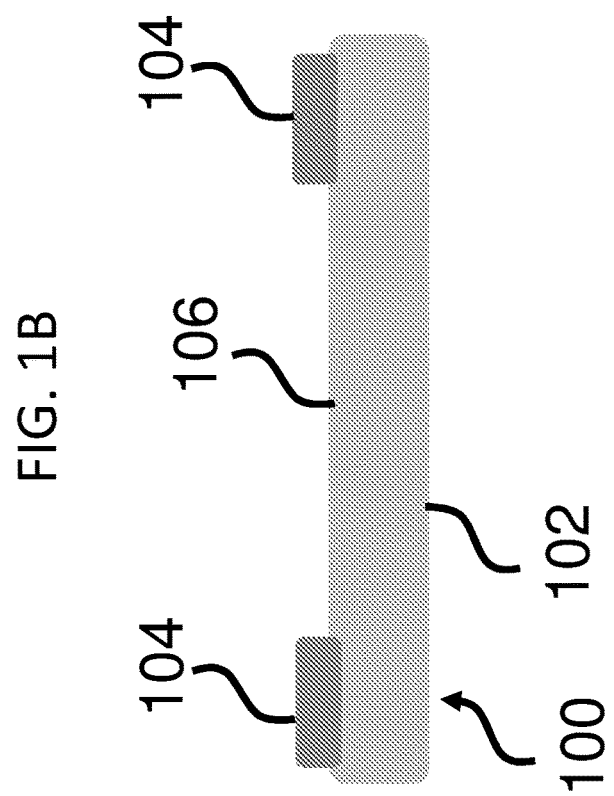
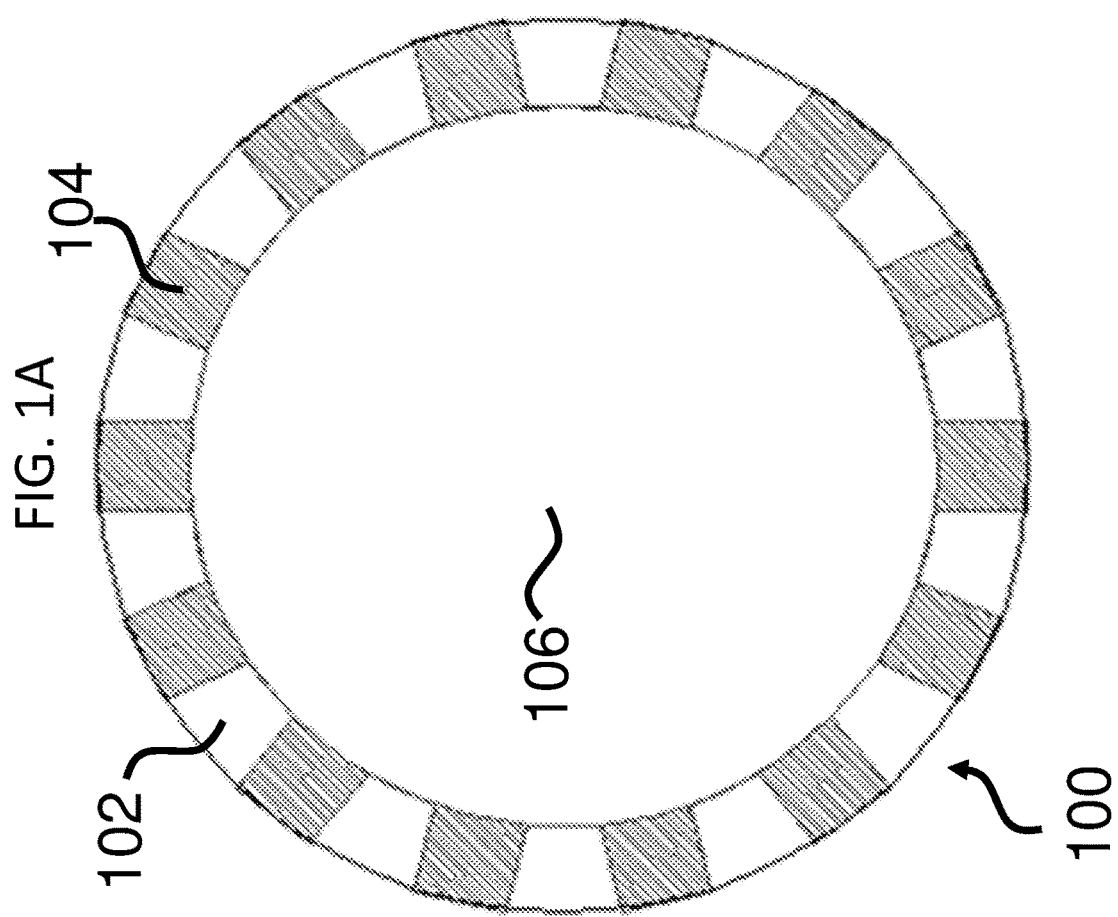

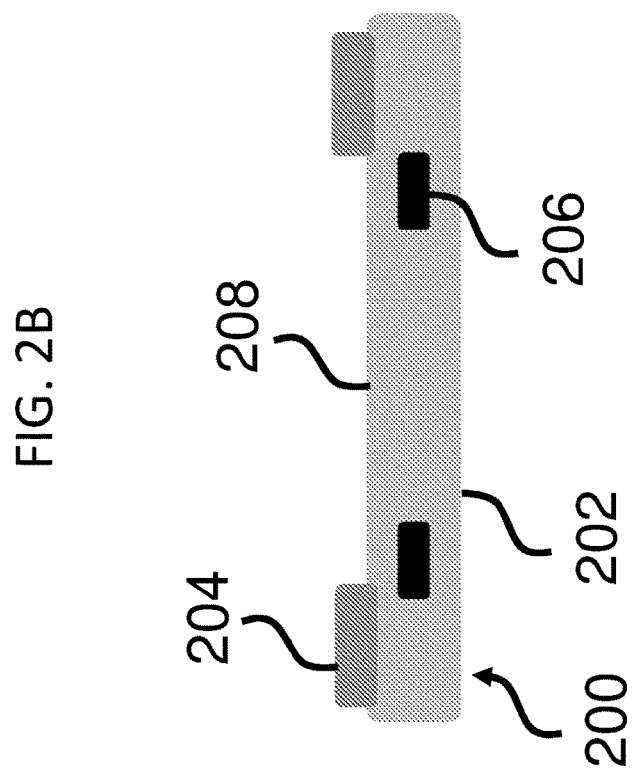
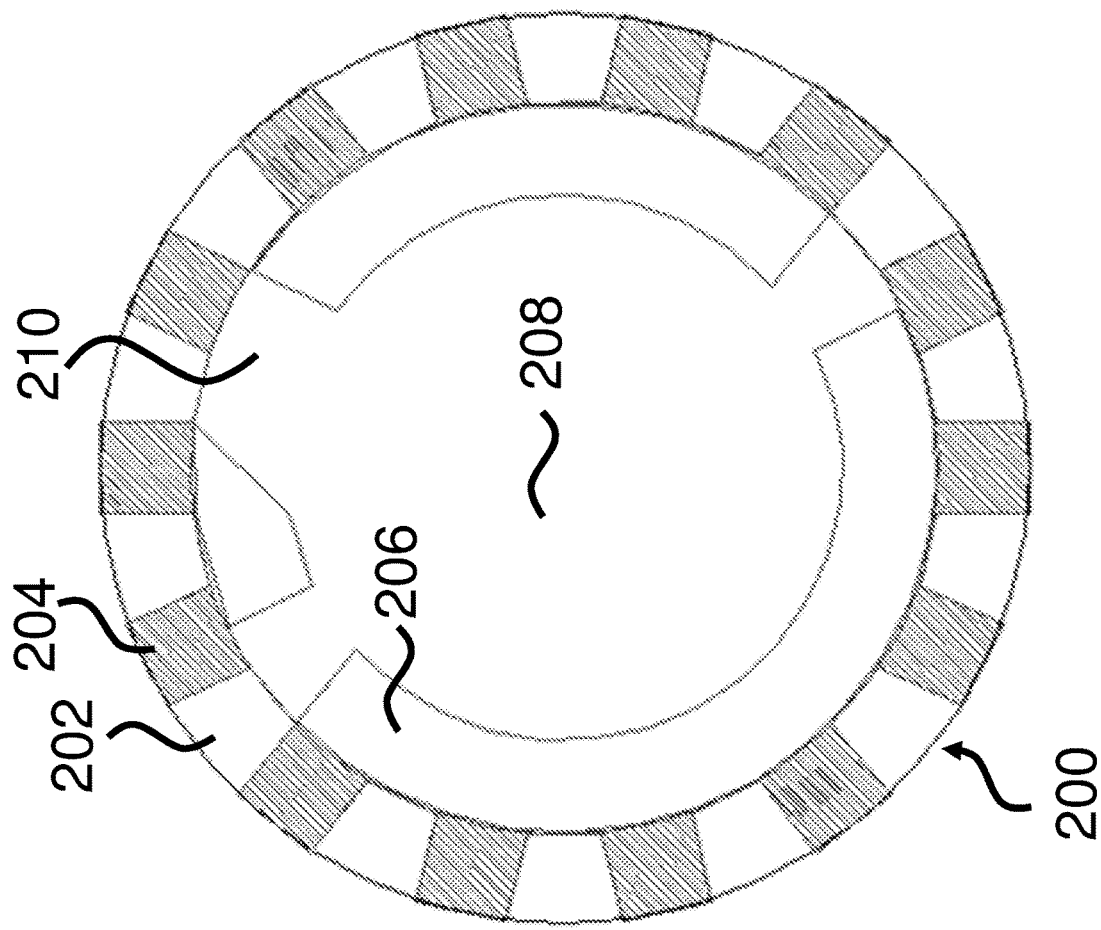

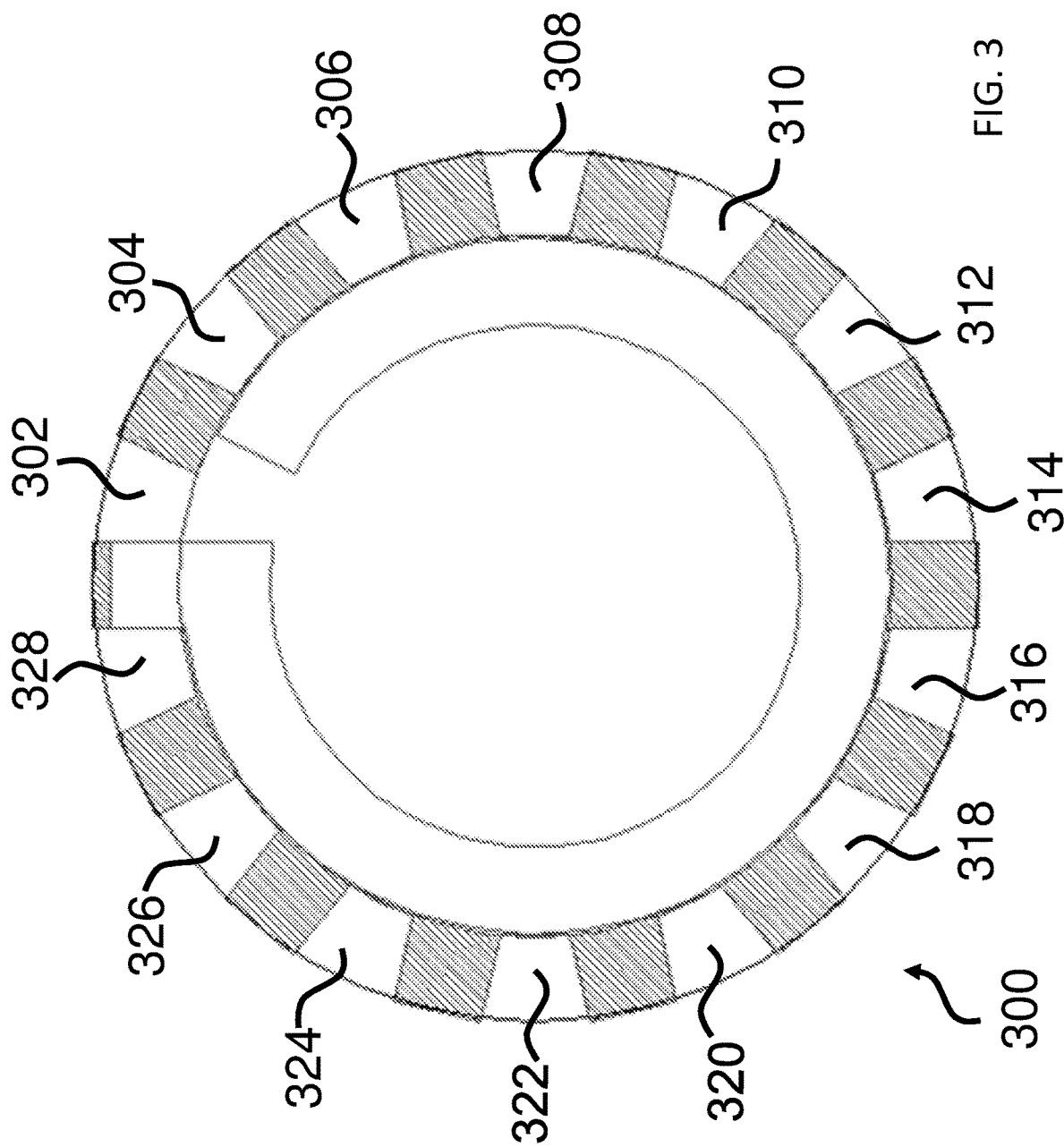

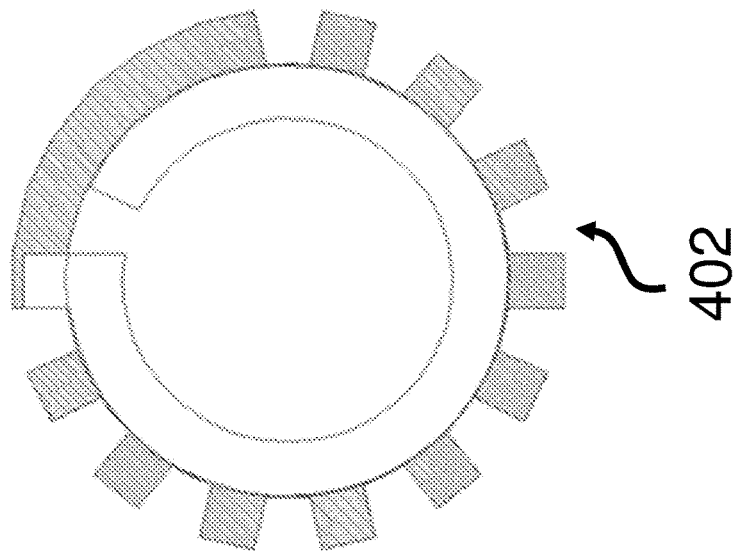
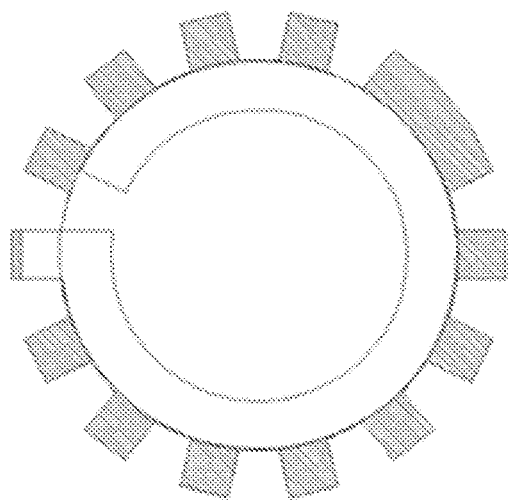
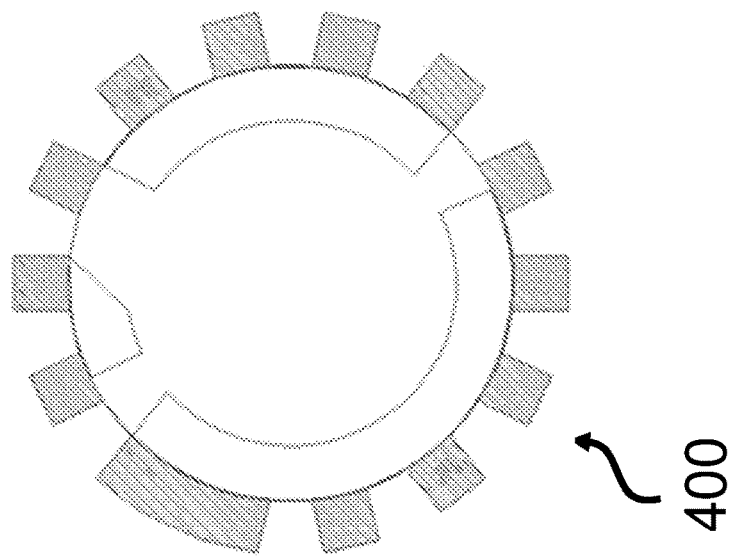
FIG. 4A

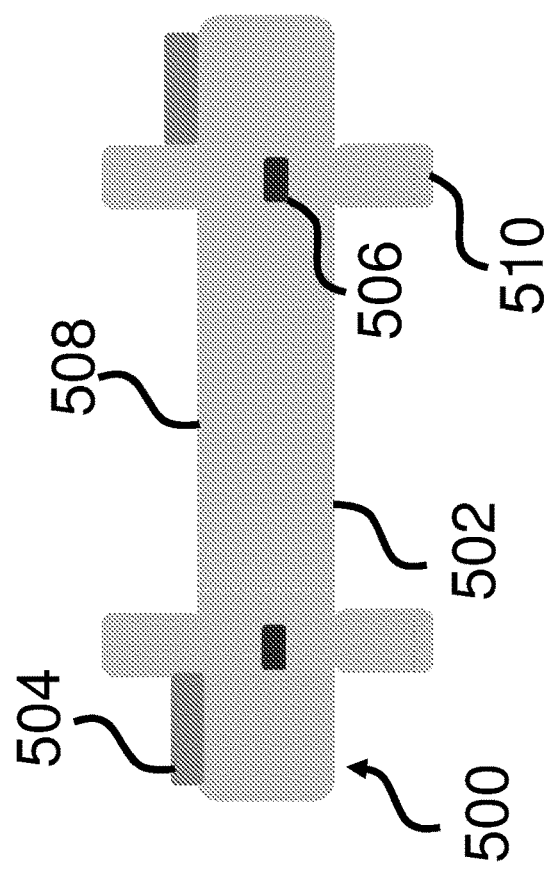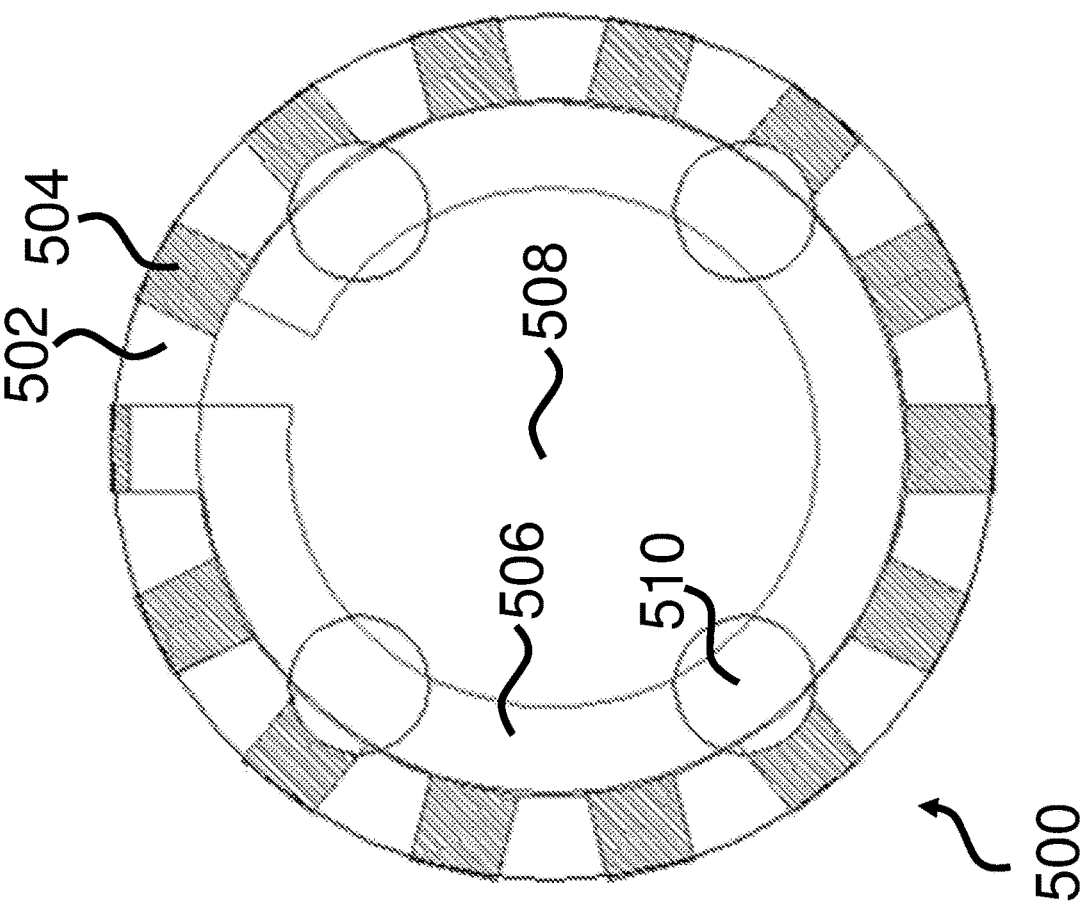

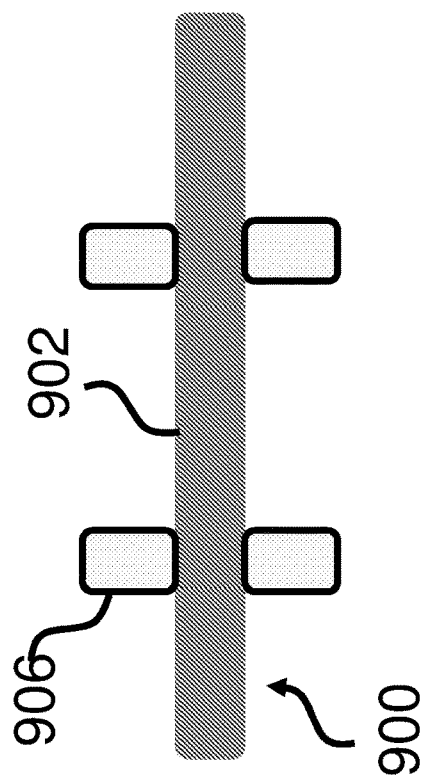
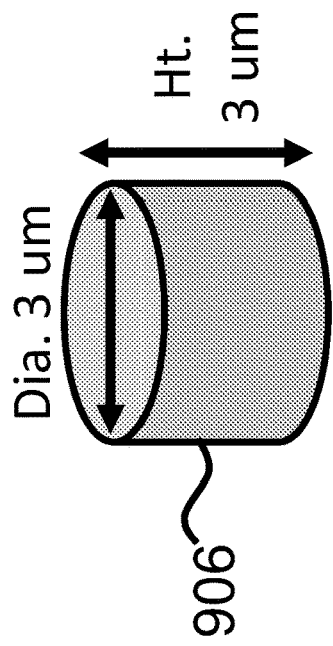
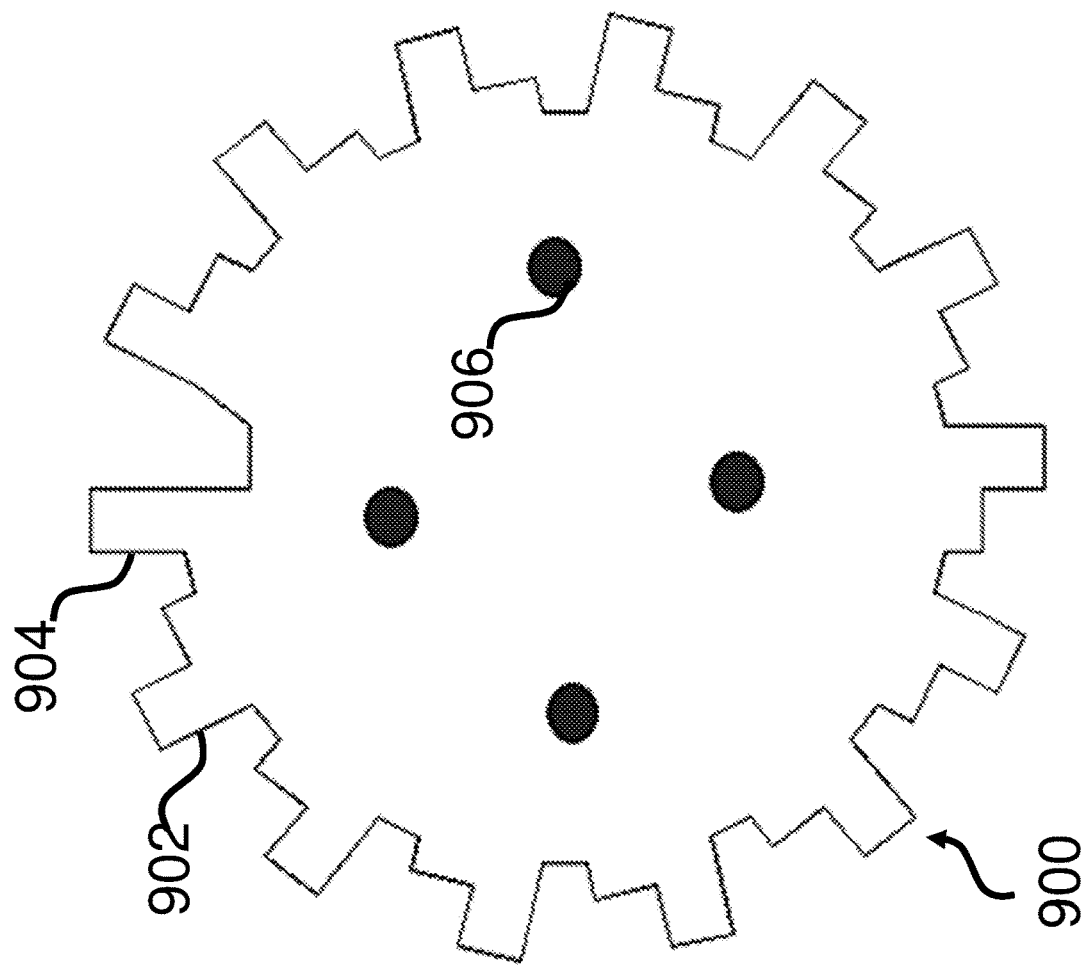

METHODS AND SYSTEMS FOR MULTIPLEX ASSAYS

CROSS REFERENCE TO RELATED APPLICATIONS

This application is a national stage application under 35 U.S.C. § 371 of International Application No. PCT/US2016/063202, filed internationally on Nov. 21, 2016, which claims the priority benefit of U.S. Provisional Application Ser. No. 62/396,056, filed Sep. 16, 2016, each of which is incorporated herein by reference in its entirety.

TECHNICAL FIELD

This application pertains to compositions comprising beads encoded with unique analog code identifiers as well as methods of making and using the same in multiplex chemical and biological assays.

BACKGROUND

Immunological and molecular diagnostic assays play a critical role both in the research and clinical fields. Often it is necessary to perform assays for a panel of multiple targets to gain meaningful or bird's-eye view results to facilitate research or clinical decision-making. This is particularly true in the era of genomics and proteomics, where an abundance of genetic markers and/or biomarkers are thought to influence or be predictive of particular disease states. In theory, assay of multiple targets can be accomplished by testing each target separately in parallel or sequentially in different reaction vessels (i.e., multiple singleplexing). However, not only are assays adopting a singleplexing strategy often cumbersome, but they also typically required large sample volumes, especially when the targets to be analyzed are large in number.

A multiplex assay simultaneously measures multiple analytes (two or more) in a single assay. Multiplex assays are commonly used in high-throughput screening settings, where many specimens can be analyzed at once. It is the ability to assay many analytes simultaneously and many specimens in parallel that is the hallmark of multiplex assays and is the reason that such assays have become a powerful tool in fields ranging from drug discovery to functional genomics to clinical diagnostics. In contrast to singleplexing, by combining all targets in the same reaction vessel, the assay is much less cumbersome and much easier to perform since only one reaction vessel is handled per sample. The required test samples can thus be dramatically reduced in volume, which is especially important when samples (e.g., tumor tissues, cerebral spinal fluid, or bone marrow) are difficult and/or invasive to retrieve in large quantities. Equally important is the fact that the reagent cost can be decreased and assay throughput increased drastically.

Many technologies for multiplex detection are available, including fluorescent-coded beads, barcoded magnetic beads, etc. Traditionally, all these suspension array beads are utilized for performing the actual bioassays. In these bead-based multiplex assay systems, there are two identification systems for every bead in the assay. One system is for the identification of the capture agent attached to the surface of the beads while the second identification system is used to indicate the presence or quantity of the analyte that binds to the particular capture agent. The Luminex technology is an example of a bead-based multiplex detection system centered on latex beads that have two different fluorophores associated with any given bead. The first fluorescent dye is injected into the beads during the latex polymerization process and is used to reveal the identity of the beads (i.e. the identification of the capture agent associated with the bead). The second fluorophore is conjugated to an analyte binder introduced to the beads when there is an analyte molecule captured by the bead-linked analyte capture agent. In other bead-based assays, the first identification system can be replaced by systems other than those which are fluorescence-based. For example, in Applied Biocode's BMB system, the first identification system is replaced by a barcode.

In spite of these advances, there remains a need for methods and systems utilizing individually identifiable beads for use in multiplex high-throughput assays that not only ensure high precision and reproducibility of experimental results, but which also are capable of performing other functions related to information and data storage that are not directly related to the assays per se.

Throughout this specification, various patents, patent applications and other types of publications (e.g., journal articles) are referenced. The disclosure of all patents, patent applications, and publications cited herein are hereby incorporated by reference in their entirety for all purposes.

SUMMARY

The present disclosure discloses, inter alia, compositions of beads (such as, polymeric beads) of substantially identical size and shape encoded with unique information-storing identifiers and methods for use of the same in multiplex chemical and biological assays.

Accordingly, provided herein are methods for conducting a multiplex assay comprising the steps of: a) contacting a sample with beads in an assay system, wherein each bead in the system comprises (1) a substantially transparent polymer layer having a first surface and a second surface, the first and the second surfaces being parallel to each other; (2) a substantially non-transparent polymer layer, wherein the substantially non-transparent polymer layer is affixed to the first surface of the substantially transparent polymer layer and encloses a center portion of the substantially transparent polymer layer, and wherein the substantially non-transparent polymer layer comprises a two-dimensional shape representing an analog code identifier; wherein the system comprises (i) at least one bead with an analog code identifier that is recognized by an imaging processor as a specific assay or assay kit, specific analyte, manufacturing lot, individual, locational identifier, or calibration signal; and (ii) a plurality of beads, wherein each bead of the plurality of beads comprises a capture agent that specifically binds to an analyte, wherein the capture agent is immobilized on at least one of the first surface and the second surface of the substantially transparent polymer layer in at least the center portion of the substantially transparent polymer layer, and wherein each bead of the plurality of beads comprises an analog code identifier corresponding to the capture agent; and simultaneously or sequentially, in any order: b) identifying the identifier that is recognized by the imaging processor as the specific assay; and c) detecting the binding of the analyte in the sample by analyzing the binding of the analyte to the capture agent immobilized on the surface of the bead based on the identification of the analog code identifier corresponding to the capture agent. In some embodiments, the system further comprises (iii) at least two beads, at least three beads, at least four beads, at least five beads, or at least six beads, each with an analog code identifier that is recognized by an imaging processor as a specific assay or assay kit, specific analyte, manufacturing lot, individual, locational identifier, or calibration signal. In some embodiments, the system further comprises (iv) at least one bead recognized by the imaging processor as a positive or negative control. In some embodiments, the locational identifier corresponds to a hospital, a diagnostic laboratory, an address, a health care professional's office, or a research laboratory. In some embodiments, the system further comprises (v) at least one bead that is pre-labeled for monitoring functions of the imaging processor. In some embodiments, the beads comprise a spherical or rectangular shape. In some embodiments, the beads are less than about 300 µm in diameter. In some embodiments, the surface of the bead is smooth and lacks surface irregularities. In some embodiments, at least one surface of the bead comprises at least one site for chemical attachment of the capture agent. In some embodiments, the capture agent is selected from the group consisting of: a DNA molecule, a DNA-analog-molecule, an RNA-molecule, an RNA-analog-molecule, a polynucleotide, a protein, an enzyme, a lipid, a phospho-lipid, a carbohydrate moiety, a polysaccharide, an antigen, a virus, a cell, an antibody, and an antibody fragment. In some embodiments, the plurality of beads are magnetic or non-magnetic. In some embodiments, the beads further comprise: (3) a magnetic, substantially non-transparent layer that encloses the center portion of the substantially transparent polymer layer between the substantially non-transparent polymer layer and the center portion of the substantially transparent polymer layer, wherein the magnetic, substantially non-transparent layer is affixed to the first surface or the second surface of the substantially transparent polymer layer. In some embodiments, the beads further comprise: (4) a second substantially transparent polymer layer aligned with the first substantially transparent polymer layer, the second substantially transparent polymer layer having a center portion that is aligned with the center portion of the first substantially transparent polymer layer, wherein the second substantially transparent polymer layer is affixed to the second surface of the first substantially transparent polymer layer and does not extend beyond the two-dimensional shape of the first substantially transparent polymer layer; and (5) a magnetic, substantially non-transparent layer that encloses the center portion of the first substantially transparent polymer layer between the substantially non-transparent polymer layer and the center portion of the substantially transparent polymer layer, wherein the magnetic, substantially non-transparent layer is affixed between the first and the second substantially transparent polymer layers. In some embodiments, the beads further comprise an orientation indicator for orienting the analog code identifier of the substantially non-transparent polymer layer. In some embodiments, the orientation indicator comprises an asymmetry of the magnetic, substantially non-transparent layer. In some embodiments, the magnetic, substantially non-transparent layer comprises nickel. In some embodiments, the magnetic, substantially non-transparent layer is between about 50 nm and about 10 µm in thickness. In some embodiments, the magnetic, substantially non-transparent layer is about 0.1 µm in thickness. In some embodiments, the two-dimensional shape of the substantially non-transparent polymer layer comprises one or more rings enclosing the center portion of the substantially transparent polymer layer, wherein at least one of the one or more rings comprises a discontinuity. In some embodiments, the two-dimensional shape of the substantially non-transparent polymer layer comprises a gear shape comprising a plurality of gear teeth, and wherein the analog code identifier is represented by one or more aspects selected from the group consisting of the height of one or more gear teeth of the plurality, the width of one or more gear teeth of the plurality, the number of gear teeth in the plurality, and the arrangement of one or more gear teeth within the plurality. In some embodiments, the plurality of gear teeth comprises one or more gear teeth that are between about 1 µm and about 10 µm wide. In some embodiments, the plurality of gear teeth comprises one or more gear teeth that are between about 1 µm and about 10 µm tall. In some embodiments, the plurality of gear teeth comprises two or more gear teeth that are spaced between about 1 µm and about 10 µm apart. In some embodiments, the beads further comprise: (6) one or more columns projecting from the first surface of the first substantially transparent polymer layer, wherein the one or more columns are not within the center portion of the first substantially transparent polymer layer; and/or (7) one or more columns projecting from the second surface of the first substantially transparent polymer layer or a surface of the second substantially transparent polymer layer that is not affixed to the first substantially transparent polymer layer, wherein the one or more columns are not within the center portions of the first or the second substantially transparent polymer layer. In some embodiments, the beads are a substantially circular disc. In some embodiments, the center portion of the first substantially transparent polymer layer comprises between about 5% and about 90% of the surface area of the first substantially transparent polymer layer. In some embodiments, the center portion of the first substantially transparent polymer layer comprises about 25% of the surface area of the first substantially transparent polymer layer. In some embodiments, the beads are less than about 200 µm in diameter. In some embodiments, the beads are about 50 µm in diameter. In some embodiments, the beads are less than about 50 µm in thickness. In some embodiments, the beads are about 10 µm in thickness. In some embodiments, the analyte is selected from the group consisting of a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, a small molecule, a bacterial cell, a cellular organelle, and an antibody fragment. In some embodiments, the substantially transparent polymer of the first or the second substantially transparent polymer layer comprises an epoxy-based polymer. In some embodiments, the epoxy-based polymer is SU-8.

In other aspects, provided herein are kits for conducting a multiplex assay comprising: a) a set of beads, wherein each bead in the set comprises (1) a substantially transparent polymer layer having a first surface and a second surface, the first and the second surfaces being parallel to each other; (2) a substantially non-transparent polymer layer, wherein the substantially non-transparent polymer layer is affixed to the first surface of the substantially transparent polymer layer and encloses a center portion of the substantially transparent polymer layer, and wherein the set of beads comprises (i) at least one bead with an analog code identifier that is recognized by an imaging processor as a specific assay or assay kit, specific analyte, manufacturing lot, individual, locational identifier, or calibration signal, and (ii) a plurality of additional beads, wherein each bead of the plurality of beads comprises a capture agent that specifically binds to an analyte, wherein the capture agent is immobilized on at least one of the first surface and the second surface of the substantially transparent polymer layer in at least the center portion of the substantially transparent polymer layer, and wherein each bead of the plurality of beads comprises an analog code identifier corresponding to the capture agent; and b) a signal-emitting entity capable of directly or indirectly binding to the analyte or capture agent. In some embodiments, the signal-emitting entity indirectly binds to the analyte or capture agent via a secondary antibody that is conjugated to the signal-emitting entity. In some embodiments, the signal-emitting entity indirectly binds to the analyte or capture agent via a nucleotide probe that is conjugated to the signal-emitting entity. In some embodiments, the signal-emitting entity is phycoerythrin, GFP, RFP, CFP, YFP, FITC, horseradish peroxidase, alkaline phosphatase, or a radiolabel. In some embodiments, the kit further comprises at least two beads, at least three beads, at least four beads, at least five beads, or at least six beads, each with an analog code identifier that is recognized by an imaging processor as a specific assay or assay kit, specific analyte, manufacturing lot, individual, locational identifier, or calibration signal. In some embodiments, the kit further comprises an imaging processor for (i) identifying the at least one bead with an identifier that is recognized by the imaging processor as a specific assay, (ii) identifying the identifier on the plurality of beads, (iii) detecting the amount of signal produced by the signal-emitting entity, (iv) identifying the at least one bead with an identifier that is recognized by the imaging processor as a manufacturing lot, (v) identifying the at least one bead with an identifier that is recognized by the imaging processor as an individual, (vi) identifying the at least one bead with an identifier that is recognized by the imaging processor as a locational identifier, or (vii) identifying the at least one bead that is pre-labeled for calibration of the imaging processor. In some embodiments, the kit further comprises an entity capable of directly or indirectly binding to the analyte or capture agent, wherein the entity comprises an affinity tag. In some embodiments, the affinity tag is biotin, $His_6$, or maltose. In some embodiments of any of the above embodiments, the kit further comprises at least one bead that is pre-labeled for monitoring functions of the imaging processor. In some embodiments, the beads comprise a spherical or rectangular shape. In some embodiments, the beads are less than about 300 µm in diameter. In some embodiments, the surface of the bead is smooth and lacks surface irregularities. In some embodiments, at least one surface of the bead comprises at least one site for chemical attachment of the capture agent. In some embodiments, the capture agent is selected from the group consisting of: a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, a small molecule, and an antibody fragment. In some embodiments, the plurality of beads are magnetic or non-magnetic. In some embodiments, the bead further comprises: (3) a magnetic, substantially non-transparent layer that encloses the center portion of the substantially transparent polymer layer between the substantially non-transparent polymer layer and the center portion of the substantially transparent polymer layer, wherein the magnetic, substantially non-transparent layer is affixed to the first surface or the second surface of the substantially transparent polymer layer. In some embodiments, the bead further comprises: (4) a second substantially transparent polymer layer aligned with the first substantially transparent polymer layer, the second substantially transparent polymer layer having a center portion that is aligned with the center portion of the first substantially transparent polymer layer, wherein the second substantially transparent polymer layer is affixed to the second surface of the first substantially transparent polymer layer and does not extend beyond the two-dimensional shape of the first substantially transparent polymer layer; and (5) a magnetic, substantially non-transparent layer that encloses the center portion of the first substantially transparent polymer layer between the substantially non-transparent polymer layer and the center portion of the substantially transparent polymer layer, wherein the magnetic, substantially non-transparent layer is affixed between the first and the second substantially transparent polymer layers. In some embodiments, the bead further comprises an orientation indicator for orienting the analog code identifier of the substantially non-transparent polymer layer. In some embodiments, the orientation indicator comprises an asymmetry of the magnetic, substantially non-transparent layer. In some embodiments, the magnetic, substantially non-transparent layer comprises nickel. In some embodiments, the magnetic, substantially non-transparent layer is between about 50 nm and about 10 µm in thickness. In some embodiments, the magnetic, substantially non-transparent layer is about 0.1 µm in thickness. In some embodiments, the two-dimensional shape of the substantially non-transparent polymer layer comprises one or more rings enclosing the center portion of the substantially transparent polymer layer, wherein at least one of the one or more rings comprises a discontinuity. In some embodiments, the two-dimensional shape of the substantially non-transparent polymer layer comprises a gear shape comprising a plurality of gear teeth, and wherein the analog code identifier is represented by one or more aspects selected from the group consisting of the height of one or more gear teeth of the plurality, the width of one or more gear teeth of the plurality, the number of gear teeth in the plurality, and the arrangement of one or more gear teeth within the plurality. In some embodiments, the plurality of gear teeth comprises one or more gear teeth that are between about 1 µm and about 10 µm wide. In some embodiments, the plurality of gear teeth comprises one or more gear teeth that are between about 1 µm and about 10 µm tall. In some embodiments, the plurality of gear teeth comprises two or more gear teeth that are spaced between about 1 µm and about 10 µm apart. In some embodiments, the beads further comprise: (6) one or more columns projecting from the first surface of the first substantially transparent polymer layer, wherein the one or more columns are not within the center portion of the first substantially transparent polymer layer; and/or (7) one or more columns projecting from the second surface of the first substantially transparent polymer layer or a surface of the second substantially transparent polymer layer that is not affixed to the first substantially transparent polymer layer, wherein the one or more columns are not within the center portions of the first or the second substantially transparent polymer layer. In some embodiments, the bead is a substantially circular disc. In some embodiments, the center portion of the first substantially transparent polymer layer comprises between about 5% and about 90% of the surface area of the first substantially transparent polymer layer. In some embodiments, the center portion of the first substantially transparent polymer layer comprises about 25% of the surface area of the first substantially transparent polymer layer. In some embodiments, the beads are less than about 200 µm in diameter. In some embodiments, the beads are about 50 µm in diameter. In some embodiments, the beads are less than about 50 µm in thickness. In some embodiments, the beads are about 10 µm in thickness. In some embodiments, the analyte is selected from the group consisting of a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, a small molecule, a bacterial cell, a cellular organelle, and an antibody fragment. In some embodiments, the substantially transparent polymer of the first or the second substantially transparent polymer layer comprises an epoxy-based polymer. In some embodiments, the epoxy-based polymer is SU-8.

In other aspects, provided herein are multiplex assay systems comprising a) a plurality of beads in the kit according to any one of the above embodiments; and b) an apparatus comprising an imaging processor system and a reaction detection system, wherein the identification of an identifier that corresponds to one or more of (i) a specific assay or assay kit, (ii) a specific analyte, (iii) a manufacturing lot, (iv) an individual, (v) a locational identifier, and/or (vi) a calibration signal by the imaging processor in the decoding system activates the use of a software analyzing detection signals detected by reaction detection system correlated to the specific assay.

In other aspects, provided herein are methods for conducting a multiplex assay comprising the steps of: a) contacting a sample with beads in an assay system, wherein each bead in the system comprises a substantially non-transparent polymer layer having a first surface and a second surface, the first and the second surfaces being parallel to each other, wherein an outline of the substantially non-transparent polymer layer comprises a two-dimensional shape that represents an analog code identifier; wherein the system comprises (i) at least one bead with an analog code identifier that is recognized by an imaging processor as a specific assay or assay kit, specific analyte, manufacturing lot, individual, locational identifier, or calibration signal, and (ii) a plurality of beads, wherein each bead of the plurality of beads comprises a capture agent that specifically binds to an analyte, wherein the capture agent is immobilized on at least one of the first surface and the second surface of the substantially transparent polymer layer in at least the center portion of the substantially transparent polymer layer, and wherein each bead of the plurality of beads comprises an analog code identifier corresponding to the capture agent; and simultaneously or sequentially, in any order: b) identifying the identifier that is recognized by the imaging processor as the specific assay; and c) detecting the binding of the analyte in the sample by analyzing the binding of the analyte to the capture agent immobilized on the surface of the bead based on the identification of the analog code identifier corresponding to the capture agent. In some embodiments, the system further comprises (iii) at least two beads, at least three beads, at least four beads, at least five beads, or at least six beads, each with an analog code identifier that is recognized by an imaging processor as a specific assay or assay kit, specific analyte, manufacturing lot, individual, locational identifier, or calibration signal. In some embodiments, the system further comprises (iv) at least one bead recognized by the imaging processor as a positive or negative control. In some embodiments, the locational identifier corresponds to a hospital, a diagnostic laboratory, an address, a health care professional's office, or a research laboratory. In some embodiments, the system further comprises (v) at least one bead that is pre-labeled for monitoring functions of the imaging processor. In some embodiments, the beads comprise a spherical or rectangular shape. In some embodiments, the beads are less than about 300 µm in diameter. In some embodiments, the surface of the bead is smooth and lacks surface irregularities. In some embodiments, at least one surface of the bead comprises at least one site for chemical attachment of the capture agent. In some embodiments, the capture agent is selected from the group consisting of: a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, and an antibody fragment. In some embodiments, the plurality of beads are magnetic or non-magnetic. In some embodiments, the beads further comprise: (2) a magnetic, substantially non-transparent layer that encloses the center portion of the substantially transparent polymer layer between the substantially non-transparent polymer layer and the center portion of the substantially transparent polymer layer, wherein the magnetic, substantially non-transparent layer is affixed to the first surface or the second surface of the substantially transparent polymer layer. In some embodiments, the beads further comprise: (3) a second substantially transparent polymer layer aligned with the first substantially transparent polymer layer, the second substantially transparent polymer layer having a center portion that is aligned with the center portion of the first substantially transparent polymer layer, wherein the second substantially transparent polymer layer is affixed to the second surface of the first substantially transparent polymer layer and does not extend beyond the two-dimensional shape of the first substantially transparent polymer layer; and (4) a magnetic, substantially non-transparent layer that encloses the center portion of the first substantially transparent polymer layer between the substantially non-transparent polymer layer and the center portion of the substantially transparent polymer layer, wherein the magnetic, substantially non-transparent layer is affixed between the first and the second substantially transparent polymer layers. In some embodiments, the beads further comprise an orientation indicator for orienting the analog code identifier of the substantially non-transparent polymer layer. In some embodiments, the orientation indicator comprises an asymmetry of the magnetic, substantially non-transparent layer. In some embodiments, the magnetic, substantially non-transparent layer comprises nickel. In some embodiments, the magnetic, substantially non-transparent layer is between about 50 nm and about 10 µm in thickness. In some embodiments, the magnetic, substantially non-transparent layer is about 0.1 µm in thickness. In some embodiments, the two-dimensional shape of the substantially non-transparent polymer layer comprises one or more rings enclosing the center portion of the substantially transparent polymer layer, wherein at least one of the one or more rings comprises a discontinuity. In some embodiments, the two-dimensional shape of the substantially non-transparent polymer layer comprises a gear shape comprising a plurality of gear teeth, and wherein the analog code identifier is represented by one or more aspects selected from the group consisting of the height of one or more gear teeth of the plurality, the width of one or more gear teeth of the plurality, the number of gear teeth in the plurality, and the arrangement of one or more gear teeth within the plurality. In some embodiments, the plurality of gear teeth comprises one or more gear teeth that are between about 1 µm and about 10 µm wide. In some embodiments, the plurality of gear teeth comprises one or more gear teeth that are between about 1 µm and about 10 µm tall. In some embodiments, the plurality of gear teeth comprises two or more gear teeth that are spaced between about 1 µm and about 10 µm apart. In some embodiments, the beads further comprise: (5) one or more columns projecting from the first surface of the first substantially transparent polymer layer, wherein the one or more columns are not within the center portion of the first substantially transparent polymer layer; and/or (6) one or more columns projecting from the second surface of the first substantially transparent polymer layer or a surface of the second substantially transparent polymer layer that is not affixed to the first substantially transparent polymer layer, wherein the one or more columns are not within the center portions of the first or the second substantially transparent polymer layer. In some embodiments, the beads are a substantially circular disc. In some embodiments, the center portion of the first substantially transparent polymer layer comprises between about 5% and about 90% of the surface area of the first substantially transparent polymer layer. In some embodiments, the center portion of the first substantially transparent polymer layer comprises about 25% of the surface area of the first substantially transparent polymer layer. In some embodiments, the beads are less than about 200 μm in diameter. In some embodiments, the beads are about 50 μm in diameter. In some embodiments, the beads are less than about 50 μm in thickness. In some embodiments, the beads are about 10 μm in thickness. In some embodiments, the analyte is selected from the group consisting of a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, a small molecule, a bacterial cell, a cellular organelle, and an antibody fragment. In some embodiments, the substantially transparent polymer of the first or the second substantially transparent polymer layer comprises an epoxy-based polymer. In some embodiments, the epoxy-based polymer is SU-8.

In other aspects, provided herein are kits for conducting a multiplex assay comprising: a) a set of beads, wherein each bead in the set comprises a substantially non-transparent polymer layer having a first surface and a second surface, the first and the second surfaces being parallel to each other, wherein an outline of the substantially non-transparent polymer layer comprises a two-dimensional shape that represents an analog code identifier; and wherein the set of beads comprises (i) at least one bead with an analog code identifier that is recognized by an imaging processor as a specific assay or assay kit, specific analyte, manufacturing lot, individual, locational identifier, or calibration signal, and (ii) a plurality of additional beads, wherein each bead of the plurality of beads comprises a capture agent that specifically binds to an analyte, wherein the capture agent is immobilized on at least one of the first surface and the second surface of the substantially transparent polymer layer in at least the center portion of the substantially transparent polymer layer, and wherein each bead of the plurality of beads comprises an analog code identifier corresponding to the capture agent; and b) a signal-emitting entity capable of directly or indirectly binding to the analyte or capture agent. In some embodiments, the signal-emitting entity indirectly binds to the analyte or capture agent via a secondary antibody that is conjugated to the signal-emitting entity. In some embodiments, the signal-emitting entity indirectly binds to the analyte or capture agent via a nucleotide probe that is conjugated to the signal-emitting entity. In some embodiments, the signal-emitting entity is phycoerythrin, GFP, RFP, CFP, YFP, FITC, horseradish peroxidase, alkaline phosphatase, or a radiolabel. In some embodiments, the kit further comprises at least two beads, at least three beads, at least four beads, at least five beads, or at least six beads, each with an analog code identifier that is recognized by an imaging processor as a specific assay or assay kit, specific analyte, manufacturing lot, individual, locational identifier, or calibration signal. In some embodiments, the kit further comprises an imaging processor for (i) identifying the at least one bead with an identifier that is recognized by the imaging processor as a specific assay, (ii) identifying the identifier on the plurality of beads, (iii) detecting the amount of signal produced by the signal-emitting entity, (iv) identifying the at least one bead with an identifier that is recognized by the imaging processor as a manufacturing lot, (v) identifying the at least one bead with an identifier that is recognized by the imaging processor as an individual, (vi) identifying the at least one bead with an identifier that is recognized by the imaging processor as a locational identifier, or (vii) identifying the at least one bead that is pre-labeled for calibration of the imaging processor. In some embodiments, the kit further comprises an entity capable of directly or indirectly binding to the analyte or capture agent, wherein the entity comprises an affinity tag. In some embodiments, the affinity tag is biotin, $His_6$, or maltose. In some embodiments, the kit further comprises at least one bead that is pre-labeled for monitoring functions of the imaging processor. In some embodiments, the beads comprise a spherical or rectangular shape. In some embodiments, the beads are less than about 300 μm in diameter. In some embodiments, the surface of the bead is smooth and lacks surface irregularities. In some embodiments, at least one surface of the bead comprises at least one site for chemical attachment of the capture agent. In some embodiments, the capture agent is selected from the group consisting of: a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, a small molecule, and an antibody fragment. In some embodiments, the plurality of beads are magnetic or non-magnetic. In some embodiments, the bead further comprises: (2) a magnetic, substantially non-transparent layer that encloses the center portion of the substantially transparent polymer layer between the substantially non-transparent polymer layer and the center portion of the substantially transparent polymer layer, wherein the magnetic, substantially non-transparent layer is affixed to the first surface or the second surface of the substantially transparent polymer layer. In some embodiments, the bead further comprises: (3) a second substantially transparent polymer layer aligned with the first substantially transparent polymer layer, the second substantially transparent polymer layer having a center portion that is aligned with the center portion of the first substantially transparent polymer layer, wherein the second substantially transparent polymer layer is affixed to the second surface of the first substantially transparent polymer layer and does not extend beyond the two-dimensional shape of the first substantially transparent polymer layer; and (4) a magnetic, substantially non-transparent layer that encloses the center portion of the first substantially transparent polymer layer between the substantially non-transparent polymer layer and the center portion of the substantially transparent polymer layer, wherein the magnetic, substantially non-transparent layer is affixed between the first and the second substantially transparent polymer layers. In some embodiments, the bead further comprises an orientation indicator for orienting the analog code identifier of the substantially non-transparent polymer layer. In some embodiments, the orientation indicator comprises an asymmetry of the magnetic, substantially non-transparent layer. In some embodiments, the magnetic, substantially non-transparent layer comprises nickel. In some embodiments, the magnetic, substantially non-transparent layer is between about 50 nm and about 10 μm in thickness. In some embodiments, the magnetic, substantially non-transparent layer is about 0.1 μm in thickness. In some embodiments, the two-dimensional shape of the substantially non-transparent polymer layer comprises one or more rings enclosing the center portion of the substantially transparent polymer layer, wherein at least one of the one or more rings comprises a discontinuity. In some embodiments, the two-dimensional shape of the substantially non-transparent polymer layer comprises a gear shape comprising a plurality of gear teeth, and wherein the analog code identifier is represented by one or more aspects selected from the group consisting of the height of one or more gear teeth of the plurality, the width of one or more gear teeth of the plurality, the number of gear teeth in the plurality, and the arrangement of one or more gear teeth within the plurality. In some embodiments, the plurality of gear teeth comprises one or more gear teeth that are between about 1 μm and about 10 μm wide. In some embodiments, the plurality of gear teeth comprises one or more gear teeth that are between about 1 μm and about 10 μm tall. In some embodiments, the plurality of gear teeth comprises two or more gear teeth that are spaced between about 1 μm and about 10 μm apart. In some embodiments, the beads further comprise: (5) one or more columns projecting from the first surface of the first substantially transparent polymer layer, wherein the one or more columns are not within the center portion of the first substantially transparent polymer layer; and/or (6) one or more columns projecting from the second surface of the first substantially transparent polymer layer or a surface of the second substantially transparent polymer layer that is not affixed to the first substantially transparent polymer layer, wherein the one or more columns are not within the center portions of the first or the second substantially transparent polymer layer. In some embodiments, the bead is a substantially circular disc. In some embodiments, the center portion of the first substantially transparent polymer layer comprises between about 5% and about 90% of the surface area of the first substantially transparent polymer layer. In some embodiments, the center portion of the first substantially transparent polymer layer comprises about 25% of the surface area of the first substantially transparent polymer layer. In some embodiments, the beads are less than about 200 μm in diameter. In some embodiments, the beads are about 50 μm in diameter. In some embodiments, the beads are less than about 50 μm in thickness. In some embodiments, the beads are about 10 μm in thickness. In some embodiments, the analyte is selected from the group consisting of a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, a small molecule, a bacterial cell, a cellular organelle, and an antibody fragment. In some embodiments, the substantially transparent polymer of the first or the second substantially transparent polymer layer comprises an epoxy-based polymer. In some embodiments, the epoxy-based polymer is SU-8.

In other aspects, provided herein are multiplex assay systems comprising a) a plurality of beads in the kit according to any of the above embodiments; and b) an apparatus comprising an imaging processor system and a reaction detection system, wherein the identification of an identifier that corresponds to one or more of (i) a specific assay or assay kit, (ii) a specific analyte, (iii) a manufacturing lot, (iv) an individual, (v) a locational identifier, and/or (vi) a calibration signal by the imaging processor in the decoding system activates the use of a software analyzing detection signals detected by reaction detection system correlated to the specific assay or assay kit.

It is to be understood that one, some, or all of the properties of the various embodiments described above and herein may be combined to form other embodiments of the present invention. These and other aspects of the present disclosure will become apparent to one of skill in the art. These and other embodiments of the present disclosure are further described by the detailed description that follows.

BRIEF DESCRIPTION OF THE DRAWINGS

FIGS. 1A & 1B show two views of an exemplary bead.
FIGS. 2A & 2B show two views of an exemplary bead.
FIG. 3 shows an exemplary analog encoding scheme that includes multiple shape variation points for generating unique analog codes.
FIG. 4A shows three examples of beads, each having a unique analog code.
FIGS. 5A & 5B show two views of an exemplary bead.
FIGS. 9A-9C show two views of an exemplary bead (FIG. 9A and FIG. 9B), along with a depiction of an optional feature (FIG. 9C).

DETAILED DESCRIPTION

Figure 1D:
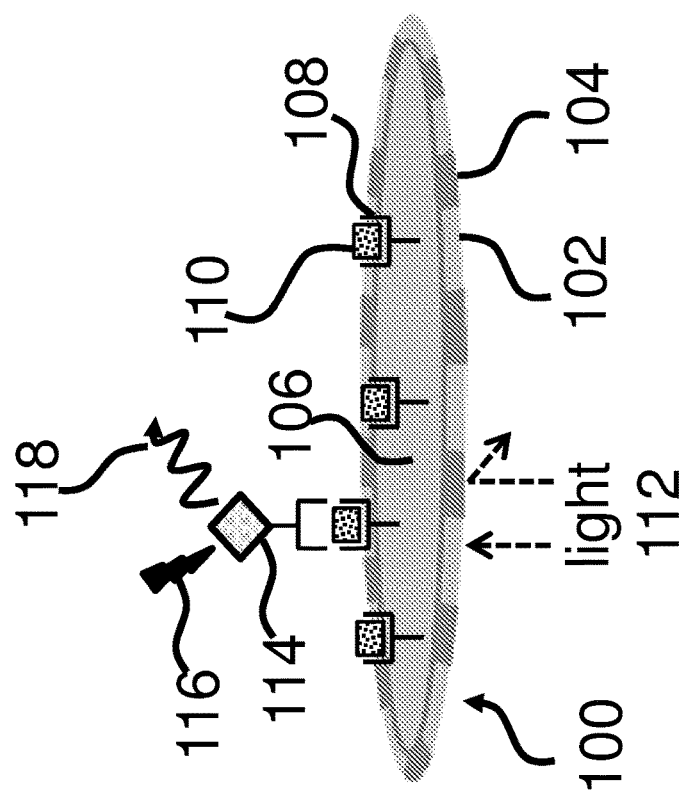
FIGS. 1C & 1D show an exemplary assay for analyte detection using an exemplary bead.

This present disclosure provides, inter alia, bead (such as polymeric bead) compositions for use in multiplex biological and chemical assays as well as methods of making and using the same. Each individual bead in a composition possesses a unique analog code identifier and specific capture agents (for example, chemical compounds and/or biomolecules) that can be attached to the surface of each bead. Such beads are therefore useful for conducting high throughput and multiplex chemical and biological assays, since, by virtue of each bead containing a unique analog code identifier corresponding to the capture agent, the identity of any individual capture agent attached to the bead can be readily ascertained. Additional beads with analog code identifiers can be included for purposes of specific information storage including, but not limited to, identification of the manufacturing lot number for the beads, identification of the assay or assay kit for which the beads will be used, identification of a location (such as, but not limited to, the origin of a sample used in an assay, or the lab or hospital where the assay was conducted), and/or identification of an individual (such as, but not limited to, an individual who supplied a given sample to be assayed), by virtue of the additional bead containing an analog code identifier corresponding to the specific information. Additional beads in the composition can be labeled with analog code identifiers for purposes of calibrating an imaging processor used to identify the identifier associated with each bead in the composition.

I. General Techniques

The practice of the present disclosure will employ, unless otherwise indicated, conventional techniques in polymer technology, photolithography, microfluidics, organic chemistry, biochemistry, oligonucleotide synthesis and modification, bioconjugate chemistry, nucleic acid hybridization, molecular biology, microbiology, genetics, recombinant DNA, and related fields as are within the skill of the art. The techniques are described in the references cited herein and are fully explained in the literature.

For molecular biology and recombinant DNA techniques, see, for example, (Maniatis, T. et al. (1982), *Molecular Cloning: A Laboratory Manual*, Cold Spring Harbor; Ausubel, F. M. (1987), *Current Protocols in Molecular Biology*, Greene Pub. Associates and Wiley-Interscience; Ausubel, F. M. (1989), *Short Protocols in Molecular Biology: A Compendium of Methods from Current Protocols in Molecular Biology*, Greene Pub. Associates and Wiley-Interscience; Sambrook, J. et al. (1989), *Molecular Cloning: A Laboratory Manual*, Cold Spring Harbor; Innis, M. A. (1990), *PCR Protocols: A Guide to Methods and Applications*, Academic Press; Ausubel, F. M. (1992), *Short Protocols in Molecular Biology: A Compendium of Methods from Current Protocols in Molecular Biology*, Greene Pub. Associates; Ausubel, F. M. (1995), *Short Protocols in Molecular Biology: A Compendium of Methods from Current Protocols in Molecular Biology*, Greene Pub. Associates; Innis, M. A. et al. (1995), *PCR Strategies*, Academic Press; Ausubel, F. M. (1999), *Short Protocols in Molecular Biology: A Compendium of Methods from Current Protocols in Molecular Biology*, Wiley, and annual updates.

For DNA synthesis techniques and nucleic acids chemistry, see for example, Gait, M. J. (1990), *Oligonucleotide Synthesis: A Practical Approach*, IRL Press; Eckstein, F. (1991), *Oligonucleotides and Analogues: A Practical Approach*, IRL Press; Adams, R. L. et al. (1992), *The Biochemistry of the Nucleic Acids*, Chapman & Hall; Shabarova, Z. et al. (1994), Advanced *Organic Chemistry of Nucleic Acids*, Weinheim; Blackburn, G. M. et al. (1996), *Nucleic Acids in Chemistry and Biology*, Oxford University Press; Hermanson, G. T. (1996), *Bioconjugate Techniques*, Academic Press).

For microfabrication, see for example, (Campbell, S. A. (1996), *The Science and Engineering of Microelectronic Fabrication*, Oxford University Press; Zaut, P. V. (1996), *Micromicroarray Fabrication: a Practical Guide to Semiconductor Processing*, Semiconductor Services; Madou, M. J. (1997), *Fundamentals of Microfabrication*, CRC Press; Rai-Choudhury, P. (1997). Handbook of Microlithography, Micromachining, & Microfabrication: Microlithography).

II. Definitions

As used herein, the singular form "a", "an", and "the" includes plural references unless indicated otherwise.

As used herein, "biomolecule" means any molecule that is produced by a living organism, including, but not limited to, large polymeric molecules such as proteins, polysaccharides, lipids, and nucleic acids as well as small molecules such as, but not limited to, primary metabolites, secondary metabolites, and natural products.

As used herein, "sample" refers to a composition containing a material, such as a molecule, to be detected. In one embodiment, the sample is a "biological sample" (i.e., any material obtained from a living source (e.g. human, animal, plant, bacteria, fungi, protist, virus)). The biological sample can be in any form, including solid materials (e.g. tissue, cell pellets and biopsies) and biological fluids (e.g. urine, blood, saliva, lymph, tears, sweat, prostatic fluid, seminal fluid, semen, bile, mucus, amniotic fluid and mouth wash (containing buccal cells)). Solid materials typically are mixed with a fluid. Sample can also refer to an environmental sample such as water, air, soil, or any other environmental source.

"Analyte," as used herein, is a broad term and is used in its ordinary sense as a substance the presence, absence, or quantity of which is to be determined, including, without limitation, to refer to a substance or chemical constituent in a sample such as a biological sample or cell or population of cells that can be analyzed. An analyte can be a substance for which a naturally occurring binding member exists, or for which a binding member can be prepared. Non-limiting examples of analytes include, for example, antibodies, antigens, polynucleotides (such as RNA, DNA, or cDNA), polypeptides, proteins, hormones, cytokines, growth factors, steroids, vitamins, toxins, drugs, and metabolites of the above substances, as well as bacteria, viruses, fungi, algae, fungal spores and the like.

As used herein, a "biological sample" refers to material that can be derived from a living source. Such samples include biomolecules and biopolymers.

As used herein, the term "chemical compound" means any chemical substance consisting of two or more different chemical elements with a unique and defined chemical structure.

It is understood that aspects and embodiments of the present disclosure described herein include "comprising," "consisting," and "consisting essentially of" aspects and embodiments.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The term "polymer" as used herein may refer to any macromolecular structure comprising repeated monomers. A polymer may be natural (e.g., found in nature) or synthetic (e.g., man-made, such as a polymer composed of non-natural monomer(s) and/or polymerized in a configuration or combination not found in nature).

The terms "substantially transparent" and "substantially non-transparent" as used herein may refer to the ability of light (e.g., of a particular wavelength, such as infrared, visible, UV, and so forth) to pass through a substrate, such as a polymer layer. A substantially transparent polymer may refer to one that is transparent, translucent, and/or pervious to light, whereas a substantially non-transparent polymer may refer to one that reflects and/or absorbs light. It is to be appreciated that whether a material is substantially transparent or substantially non-transparent may depend upon the wavelength and/or intensity of light illuminating the material, as well as the means detecting the light traveling through the material (or a decrease or absence thereof). In some embodiments, a substantially non-transparent material causes a perceptible decrease in transmitted light as compared to the surrounding material or image field, e.g., as imaged by light microscopy (e.g., bright field, dark field, phase contrast, differential interference contrast (DIC), Nomarski interference contrast (NIC), Nomarski, Hoffman modulation contrast (HMC), or fluorescence microscopy). In some embodiments, a substantially transparent material allows a perceptible amount of transmitted light to pass through the material, e.g., as imaged by light microscopy (e.g., bright field, dark field, phase contrast, differential interference contrast (DIC), Nomarski interference contrast (NIC), Nomarski, Hoffman modulation contrast (HMC), or fluorescence microscopy).

The term "analog code" as used herein may refer to any code in which the encoded information is represented in a non-quantized and/or non-discrete manner, e.g., as opposed to a digital code. For example, a digital code is sampled at discrete positions for a limited set of values (e.g., 0/1 type values), whereas an analog code may be sampled at a greater range of positions (or as a continuous whole) and/or may contain a wider set of values (e.g., shapes). In some embodiments, an analog code may be read or decoded using one or more analog shape recognition techniques.

The term "capture agent" as used herein is a broad term and is used in its ordinary sense to refer to any compound or substance capable of specifically recognizing an analyte of interest. In some embodiments, specific recognition may refer to specific binding. Non-limiting examples of capture agents include, for example, a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, a small molecule, a bacterial cell, a cellular organelle, and an antibody fragment.

The term "antibody" is used in the broadest sense and includes monoclonal antibodies (including full length antibodies which have an immunoglobulin Fc region), polyclonal antibodies, multispecific antibodies (e.g., bispecific antibodies, diabodies, and single-chain molecules), as well as antibody fragments (e.g., Fab, F(ab')$_2$, and Fv).

III. Bead Compositions

Provided herein are encoded beads suitable for analyte detection, e.g., multiplex analyte detection. As used herein, the terms bead(s) and microcarrier(s) are used interchangeably. Multiple configurations for encoded beads are contemplated, described, and exemplified herein.

In some aspects, provided herein are encoded beads that comprise: a substantially transparent polymer layer having a first surface and a second surface, the first and the second surfaces being parallel to each other; a substantially non-transparent polymer layer, wherein the substantially non-transparent polymer layer is affixed to the first surface of the substantially transparent polymer layer and encloses a center portion of the substantially transparent polymer layer, and wherein the substantially non-transparent polymer layer comprises a two-dimensional shape representing an analog code. In some embodiments, the beads further comprise a capture agent for capturing an analyte, wherein the capture agent is coupled to at least one of the first surface and the second surface of the substantially transparent polymer layer in at least the center portion of the substantially transparent polymer layer. Thus, the bead contains at least two layers: one of which is substantially transparent, and the other of which is a substantially non-transparent, two-dimensional shape that represents an analog code. Advantageously, these beads may employ a variety of two-dimensional shapes while still retaining a uniform overall form (e.g., the perimeter of the substantially transparent polymer layer) for uniformity of aspects including, for example, overall dimensions, physical properties, and/or behavior in solution. Examples of this type of bead and aspects thereof are illustrated in FIGS. 1A-5B.

In some embodiments, the bead further includes a magnetic, substantially non-transparent layer affixed to a surface of the substantially transparent polymer layer that encloses the center portion of the substantially transparent polymer layer. In some embodiments, the magnetic, substantially non-transparent layer is between the substantially non-transparent polymer layer and the center portion of the substantially transparent polymer layer.

In some embodiments, the bead further includes a second substantially transparent polymer layer aligned with and affixed to the first substantially transparent polymer layer. In some embodiments, the first and second substantially transparent polymer layers each have a center portion, and the center portions of both the first and second substantially transparent polymer layers are aligned. In some embodiments, the bead further includes a magnetic, substantially non-transparent layer that encloses the center portions of both the first and second substantially transparent polymer layers. In some embodiments, the magnetic, substantially non-transparent layer is affixed between the first and second substantially transparent polymer layers. In some embodiments, the magnetic, substantially non-transparent layer is between the substantially non-transparent polymer layer and the center portions of both the first and second substantially transparent polymer layers.

In some embodiments, the magnetic, substantially non-transparent layer is between about 50 nm and about 10 μm in thickness. In some embodiments, the thickness of the magnetic, substantially non-transparent layer is less than about any of the following thicknesses (in nm): 10000, 9500, 9000, 8500, 8000, 7500, 7000, 6500, 6000, 5500, 5000, 4500, 4000, 3500, 3000, 2500, 2000, 1500, 1000, 950, 900, 850, 800, 750, 700, 650, 600, 550, 500, 450, 400, 350, 300, 250, 200, 150, or 100. In some embodiments, the thickness of the magnetic, substantially non-transparent layer is greater than about any of the following thicknesses (in nm): 50, 100, 150, 200, 250, 300, 350, 400, 450, 500, 550, 600, 650, 700, 750, 800, 850, 900, 950, 1000, 1500, 2000, 2500, 3000, 3500, 4000, 4500, 5000, 5500, 6000, 6500, 7000, 7500, 8000, 8500, 9000, or 9500. That is, the thickness of the magnetic, substantially non-transparent layer may be any of a range of thicknesses (in nm) having an upper limit of 10000, 9500, 9000, 8500, 8000, 7500, 7000, 6500, 6000, 5500, 5000, 4500, 4000, 3500, 3000, 2500, 2000, 1500, 1000, 950, 900, 850, 800, 750, 700, 650, 600, 550, 500, 450, 400, 350, 300, 250, 200, 150, or 100 and an independently selected lower limit of 50, 100, 150, 200, 250, 300, 350, 400, 450, 500, 550, 600, 650, 700, 750, 800, 850, 900, 950, 1000, 1500, 2000, 2500, 3000, 3500, 4000, 4500, 5000, 5500, 6000, 6500, 7000, 7500, 8000, 8500, 9000, or 9500, wherein the lower limit is less than the upper limit.

In some embodiments, the magnetic, substantially non-transparent layer is about 0.1 μm in thickness. In some embodiments, the magnetic, substantially non-transparent layer is about 50 nm, about 100 nm, about 150 nm, about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, about 1 μm, about 1.5 μm, about 2 μm, about 2.5 μm, about 3 μm, about 3.5 μm, about 4 μm, about 4.5 μm, about 5 μm, about 5.5 μm, about 6 μm, about 6.5 μm, about 7 μm, about 7.5 μm, about 8 μm, about 8.5 μm, about 9 μm, about 9.5 μm, or about 10 μm in thickness. In some embodiments, the thickness of the magnetic, substantially non-transparent layer is about 0.01 μm, about 0.02 μm, about 0.03 μm, about 0.04 μm, about 0.05 μm, about 0.06 μm, about 0.07 μm, about 0.08 μm, about 0.09 μm, about 0.1 μm, about 0.11 μm, about 0.12 μm, about 0.13 μm, about 0.14 μm, about 0.15 μm, about 0.16 μm, about 0.17 μm, about 0.18 μm, about 0.19 μm, about 0.20 μm, about 0.25 μm, about 0.30 μm, about 0.35 μm, about 0.40 μm, about 0.45 μm, or about 0.50 μm.

In some embodiments, the bead further includes an orientation indicator for orienting the analog code of the substantially non-transparent polymer layer. Any feature of the bead that is visible and/or detectable by imaging (e.g., a form of microscopic or other imaging described herein) and/or by image recognition software may serve as an orientation indicator. An orientation indicator may serve as a point of reference, e.g., for an image recognition algorithm, to orient the image of an analog code in a uniform orientation (i.e., the shape of the substantially non-transparent polymer layer). Advantageously, this simplifies image recognition, as the algorithm would only need to compare the image of a particular analog code against a library of analog codes in the same orientation, and not against a library including all analog codes in all possible orientations. In some embodiments, the orientation indicator may be independent of the substantially non-transparent polymer layer. For example, it may be formed as a part of a magnetic layer and/or substantially transparent polymer layer. In other embodiments, the orientation indicator may be formed as part of the substantially non-transparent polymer layer. In some embodiments, the orientation indicator comprises an asymmetry of the magnetic, substantially non-transparent layer (e.g., as illustrated by gap 210 in FIG. 2A).

In some embodiments, the bead further includes one or more columns projecting from a surface of the bead (e.g., the top and/or bottom surface of the bead). As used herein, a "column" may refer to any geometric shape that projects from the bead surface and does not necessarily denote any regularity in dimensions, nor any cylindrical character. For example, the outer surface of a column may or may not be parallel with the bead surface. Examples of columnar shapes that may project from a bead include without limitation a rectangular prism, a triangle, a pyramid, a cube, a cylinder, a sphere or half-sphere, a cone, and so forth. In some embodiments, the one or more columns are not within a center portion of the first and/or the second substantially transparent polymer layer. In some embodiments, the one or more columns may project from an outside-facing surface (e.g., a surface not affixed to another layer) of one or more of the first and the second substantially transparent polymer layers. It is to be noted that any descriptions of bead thickness herein do not include the one or more columns in the stated dimensions. That is to say, bead thickness as described herein is independent of any optional columns projecting therefrom.

In some embodiments, the one or more columns are between about 1 μm and about 10 μm tall. In some embodiments, the one or more columns are about 1 μm tall, about 1.5 μm tall, about 2 μm tall, about 2.5 μm tall, about 3 μm tall, about 3.5 μm tall, about 4 μm tall, about 4.5 μm tall, about 5 μm tall, about 5.5 μm tall, about 6 μm tall, about 6.5 μm tall, about 7 μm tall, about 7.5 μm tall, about 8 μm tall, about 8.5 μm tall, about 9 μm tall, about 9.5 μm tall, or about 10 μm tall. In some embodiments, the one or more columns are less than about any of the following heights (in μm): 10, 9.5, 9, 8.5, 8, 7.5, 7, 6.5, 6, 5.5, 5, 4.5, 4, 3.5, 3, 2.5, 2, or 1.5. In some embodiments, the one or more columns are greater than about any of the following heights (in μm): 1, 1.5, 2, 2.5, 3, 3.5, 4, 4.5, 5, 5.5, 6, 6.5, 7, 7.5, 8, 8.5, 9, or 9.5. That is, the one or more columns can be any of a range of heights having an upper limit of 10, 9.5, 9, 8.5, 8, 7.5, 7, 6.5, 6, 5.5, 5, 4.5, 4, 3.5, 3, 2.5, 2, or 1.5 and an independently selected lower limit of 1, 1.5, 2, 2.5, 3, 3.5, 4, 4.5, 5, 5.5, 6, 6.5, 7, 7.5, 8, 8.5, 9, or 9.5, wherein the lower limit is less than the upper limit.

In some embodiments, the one or more columns may be cylindrical in shape. In some embodiments, the one or more columns have a diameter between about 1 μm and about 10 μm. In some embodiments, the one or more columns have a diameter of about 1 μm, about 1.5 μm, about 2 μm, about 2.5 μm, about 3 μm, about 3.5 μm, about 4 μm, about 4.5 μm, about 5 μm, about 5.5 μm, about 6 μm, about 6.5 μm, about 7 μm, about 7.5 μm, about 8 μm, about 8.5 μm, about 9 μm, about 9.5 μm, or about 10 μm. In some embodiments, the one or more columns have a diameter less than about any of the following lengths (in μm): 10, 9.5, 9, 8.5, 8, 7.5, 7, 6.5, 6, 5.5, 5, 4.5, 4, 3.5, 3, 2.5, 2, or 1.5. In some embodiments, the one or more columns have a diameter greater than about any of the following lengths (in μm): 1, 1.5, 2, 2.5, 3, 3.5, 4, 4.5, 5, 5.5, 6, 6.5, 7, 7.5, 8, 8.5, 9, or 9.5. That is, the one or more columns can have any of a range of diameters having an upper limit of 10, 9.5, 9, 8.5, 8, 7.5, 7, 6.5, 6, 5.5, 5, 4.5, 4, 3.5, 3, 2.5, 2, or 1.5 and an independently selected lower limit of 1, 1.5, 2, 2.5, 3, 3.5, 4, 4.5, 5, 5.5, 6, 6.5, 7, 7.5, 8, 8.5, 9, or 9.5, wherein the lower limit is less than the upper limit. In other embodiments, the one or more columns may have roughly the same width as any diameter described supra, or a range of widths roughly the same as any range of diameters described supra, but the one or more columns may adopt the shape of an elliptical cylinder, parabolic cylinder, hyperbolic cylinder, or any other cylindrical or polyhedral shape described herein or known in the art.

In other aspects, provided herein are encoded beads that comprise a substantially non-transparent polymer layer having a first surface and a second surface, the first and the second surfaces being parallel to each other, wherein an outline of the substantially non-transparent polymer layer comprises a two-dimensional shape that represents an analog code. In some embodiments, the beads further comprise a capture agent for capturing an analyte, wherein the capture agent is coupled to at least one of the first surface and the second surface of the substantially non-transparent polymer layer in at least a center portion of the substantially non-transparent polymer layer. Thus, the bead is encoded by the shape (e.g., outline) of the bead itself: a two-dimensional shape that represents an analog code. Advantageously, these beads may be manufactured efficiently and with high precision, allowing for highly accurate decoding and cost-efficient production. Examples of this type of bead and aspects thereof are illustrated in FIGS. 6A-9C.

In some embodiments, the bead further includes one or more columns projecting from a surface of the substantially non-transparent polymer layer. As described in greater detail supra, a "column" may refer to any geometric shape that projects from the bead surface and does not necessarily denote any regularity in columnar dimension(s). Any of the exemplary columnar shapes described above may be used.

In some embodiments, the one or more columns are between about 1 μm and about 10 μm tall. In some embodiments, the one or more columns are about 1 μm tall, about 1.5 μm tall, about 2 μm tall, about 2.5 μm tall, about 3 μm tall, about 3.5 μm tall, about 4 μm tall, about 4.5 μm tall, about 5 μm tall, about 5.5 μm tall, about 6 μm tall, about 6.5 μm tall, about 7 μm tall, about 7.5 μm tall, about 8 μm tall, about 8.5 μm tall, about 9 μm tall, about 9.5 μm tall, or about 10 μm tall. In some embodiments, the one or more columns are less than about any of the following heights (in μm): 10, 9.5, 9, 8.5, 8, 7.5, 7, 6.5, 6, 5.5, 5, 4.5, 4, 3.5, 3, 2.5, 2, or 1.5. In some embodiments, the one or more columns are greater than about any of the following heights (in μm): 1, 1.5, 2, 2.5, 3, 3.5, 4, 4.5, 5, 5.5, 6, 6.5, 7, 7.5, 8, 8.5, 9, or 9.5. That is, the one or more columns can be any of a range of heights having an upper limit of 10, 9.5, 9, 8.5, 8, 7.5, 7, 6.5, 6, 5.5, 5, 4.5, 4, 3.5, 3, 2.5, 2, or 1.5 and an independently selected lower limit of 1, 1.5, 2, 2.5, 3, 3.5, 4, 4.5, 5, 5.5, 6, 6.5, 7, 7.5, 8, 8.5, 9, or 9.5, wherein the lower limit is less than the upper limit.

In some embodiments, the one or more columns may be cylindrical in shape. In some embodiments, the one or more columns have a diameter between about 1 μm and about 10 μm. In some embodiments, the one or more columns have a diameter of about 1 μm, about 1.5 μm, about 2 μm, about 2.5 μm, about 3 μm, about 3.5 μm, about 4 μm, about 4.5 μm, about 5 μm, about 5.5 μm, about 6 μm, about 6.5 μm, about 7 μm, about 7.5 μm, about 8 μm, about 8.5 μm, about 9 μm, about 9.5 μm, or about 10 μm. In some embodiments, the one or more columns have a diameter less than about any of the following lengths (in μm): 10, 9.5, 9, 8.5, 8, 7.5, 7, 6.5, 6, 5.5, 5, 4.5, 4, 3.5, 3, 2.5, 2, or 1.5. In some embodiments, the one or more columns have a diameter greater than about any of the following lengths (in μm): 1, 1.5, 2, 2.5, 3, 3.5, 4, 4.5, 5, 5.5, 6, 6.5, 7, 7.5, 8, 8.5, 9, or 9.5. That is, the one or more columns can have any of a range of diameters having an upper limit of 10, 9.5, 9, 8.5, 8, 7.5, 7, 6.5, 6, 5.5, 5, 4.5, 4, 3.5, 3, 2.5, 2, or 1.5 and an independently selected lower limit of 1, 1.5, 2, 2.5, 3, 3.5, 4, 4.5, 5, 5.5, 6, 6.5, 7, 7.5, 8, 8.5, 9, or 9.5, wherein the lower limit is less than the upper limit. In other embodiments, the one or more columns may have roughly the same width as any diameter described supra, or a range of widths roughly the same as any range of diameters described supra, but the one or more columns may adopt the shape of an elliptical cylinder, parabolic cylinder, hyperbolic cylinder, or any other cylindrical or polyhedral shape described herein or known in the art.

In some embodiments, the bead further includes a magnetic layer comprising a magnetic material affixed to a surface of the substantially non-transparent polymer layer. In some embodiments, the magnetic layer does not extend beyond the two-dimensional shape of the substantially non-transparent polymer layer. That is to say, if the outline of the substantially non-transparent polymer layer were to be imaged, the resulting image would not be altered by the presence or absence of the magnetic layer. In some embodiments, the magnetic layer may include the one or more columns described above. That is, the one or more columns described above may be made of a magnetic material described herein.

In some embodiments, the bead further includes an orientation indicator for orienting the analog code of the substantially non-transparent polymer layer. Any feature of the bead that is visible and/or detectable by imaging (e.g., a form of microscopic or other imaging described herein) and/or by image recognition software may serve as an orientation indicator. An orientation indicator may serve as a point of reference, e.g., for an image recognition algorithm, to orient the image of an analog code in a uniform orientation (i.e., the shape of the substantially non-transparent polymer layer). Advantageously, this simplifies image recognition, as the algorithm would only need to compare the image of a particular analog code against a library of analog codes in the same orientation, and not against a library including all analog codes in all possible orientations. In some embodiments, the orientation indicator comprises an asymmetry of the outline of the substantially non-transparent polymer layer. For example, the orientation indicator may comprise a visible feature, such as an asymmetry, of the outline of the bead (e.g., as illustrated by start positions 804 and 904 in FIGS. 8A and 9A).

Any of the beads described herein may include one or more of the features, elements, or aspects described below. In addition, one or more of the features, elements, or aspects described below may adopt different characteristics depending on the embodiment of the bead, e.g., as described above.

In some embodiments, a substantially transparent polymer of the present disclosure comprises an epoxy-based polymer. Suitable epoxy-based polymers for fabrication of the compositions described herein include, but are not limited to, the EPON™ family of epoxy resins provided by Hexion Specialty Chemicals, Inc. (Columbus, Ohio) and any number of epoxy resins provided by The Dow Chemical Company (Midland, Mich.). Many examples of suitable polymers are commonly known in the art, including without limitation SU-8, EPON 1002F, EPON 165/154, and a poly (methyl methacrylate)/poly(acrylic acid) block copolymer (PMMA-co-PAA). For additional polymers, see, for example, Warad, *IC Packaging: Package Construction Analysis in Ultra Small IC Packaging*, LAP LAMBERT Academic Publishing (2010); *The Electronic Packaging Handbook*, CRC Press (Blackwell, ed.), (2000); and Pecht et al., *Electronic Packaging Materials and Their Properties*, CCR Press, 1$^{st}$ ed., (1998). These types of materials have the advantage of not swelling in aqueous environments which ensures that uniform bead size and shape are maintained within the population of beads. In some embodiments, the substantially transparent polymer is a photoresist polymer. In some embodiments, the epoxy-based polymer is an epoxy-based, negative-tone, near-UV photoresist. In some embodiments, the epoxy-based polymer is SU-8.

In some embodiments, the substantially non-transparent polymer is a polymer described herein (e.g., SU-8) mixed with one or more non-transparent or colored dye(s). In other embodiments, the substantially non-transparent polymer is a black matrix resist. Any black matrix resist known in the art may be used; see, e.g., U.S. Pat. No. 8,610,848 for exemplary black matrix resists and methods related thereto. In some embodiments, the black matrix resist may be a photoresist colored with a black pigment, e.g., as patterned on the color filter of an LCD as part of a black matrix. Black matrix resists may include without limitation those sold by Toppan Printing Co. (Tokyo), Tokyo OHKA Kogyo (Kawasaki), and Daxin Materials Corp. (Taichung City, Taiwan).

In some embodiments, reference may be made to a center portion of one or more polymer layers. A center portion of the present disclosure may take any shape. In some embodiments, the shape of the center portion may reflect or correspond to the shape (e.g., outline) of the corresponding polymer layer. In other embodiments, the shape of the center portion may be independent of the shape (e.g., outline) of the corresponding polymer layer. For example, a center portion of a circular bead surface may be circular in some embodiments and square in other embodiments. A center portion of a square bead surface may be square in some embodiments and circular in other embodiments.

In some embodiments, a center portion of a polymer layer of the present disclosure is about 5%, about 7%, about 10%, about 15%, about 20%, about 25%, about 30%, about 35%, about 40%, about 45%, about 50%, about 55%, about 60%, about 65%, about 70%, about 75%, about 80%, about 85%, or about 90% of the surface area of the polymer layer. In some embodiments, a center portion of a polymer layer of the present disclosure is less than about any of the following fractions of the substantially transparent polymer layer (in %): 90, 85, 80, 75, 70, 65, 60, 55, 50, 45, 40, 35, 30, 25, 20, 15, 10, or 7. In some embodiments, a center portion of a polymer layer of the present disclosure is greater than about any of the following fractions of the substantially transparent polymer layer (in %): 5, 7, 10, 15, 20, 25, 30, 35, 40, 45, 50, 55, 60, 65, 70, 75, 80, or 85. That is, the fraction of the polymer layer surface area included in the center portion may be any of a range of percentages having an upper limit of 90, 85, 80, 75, 70, 65, 60, 55, 50, 45, 40, 35, 30, 25, 20, 15, 10, or 7 and an independently selected lower limit of 5, 7, 10, 15, 20, 25, 30, 35, 40, 45, 50, 55, 60, 65, 70, 75, 80, or 85, wherein the lower limit is less than the upper limit. In some embodiments, the center portion of a polymer layer comprises about 25% of the surface area of the polymer layer. In some embodiments, a center portion of a bead surface includes the entire surface minus an outline portion of the bead.

As described above, a bead of the present disclosure may further include a magnetic layer, which may adopt a variety of shapes as described herein. In some embodiments, the magnetic layer may be a substantially non-transparent layer. In some embodiments, the magnetic layer may comprise a magnetic material. A magnetic layer of the present disclosure may be made of any suitable magnetic material, such as a material with paramagnetic, ferromagnetic, or ferrimagnetic properties. Examples of magnetic materials include without limitation iron, nickel, cobalt, and some rare earth metals (e.g., gadolinium, dysprosium, neodymium, and so forth), as well as alloys thereof. In some embodiments, the magnetic material comprises nickel, including without limitation elemental nickel and magnetic nickel alloys such as alnico and permalloy. The inclusion of a magnetic layer in a bead of the present disclosure may be advantageous, e.g., in facilitating magnetic separation, which may be useful for washing, collecting, and otherwise manipulating one or more beads.

As described above, in some embodiments, the magnetic layer may be affixed to a surface of the substantially transparent polymer layer and enclose a center portion of the substantially transparent polymer layer. In other embodiments, as described above, the magnetic layer may include one or more columns; i.e., the one or more columns described above may be made of a magnetic material described herein.

In some embodiments, a bead of the present disclosure may be encoded with a substantially non-transparent layer that constitutes a two-dimensional shape. For example, as described above, the two-dimensional shape may constitute the shape of a substantially non-transparent layer that contrasts with a substantially transparent layer of the bead, or it may constitute the shape of the bead itself (e.g., the perimeter). Any two-dimensional shape that can encompass a plurality of resolvable and distinctive varieties may be used. In some embodiments, the two-dimensional shape comprises one or more of linear, circular, elliptical, rectangular, quadrilateral, or higher polygonal aspects, elements, and/or shapes.

Figure 4B:
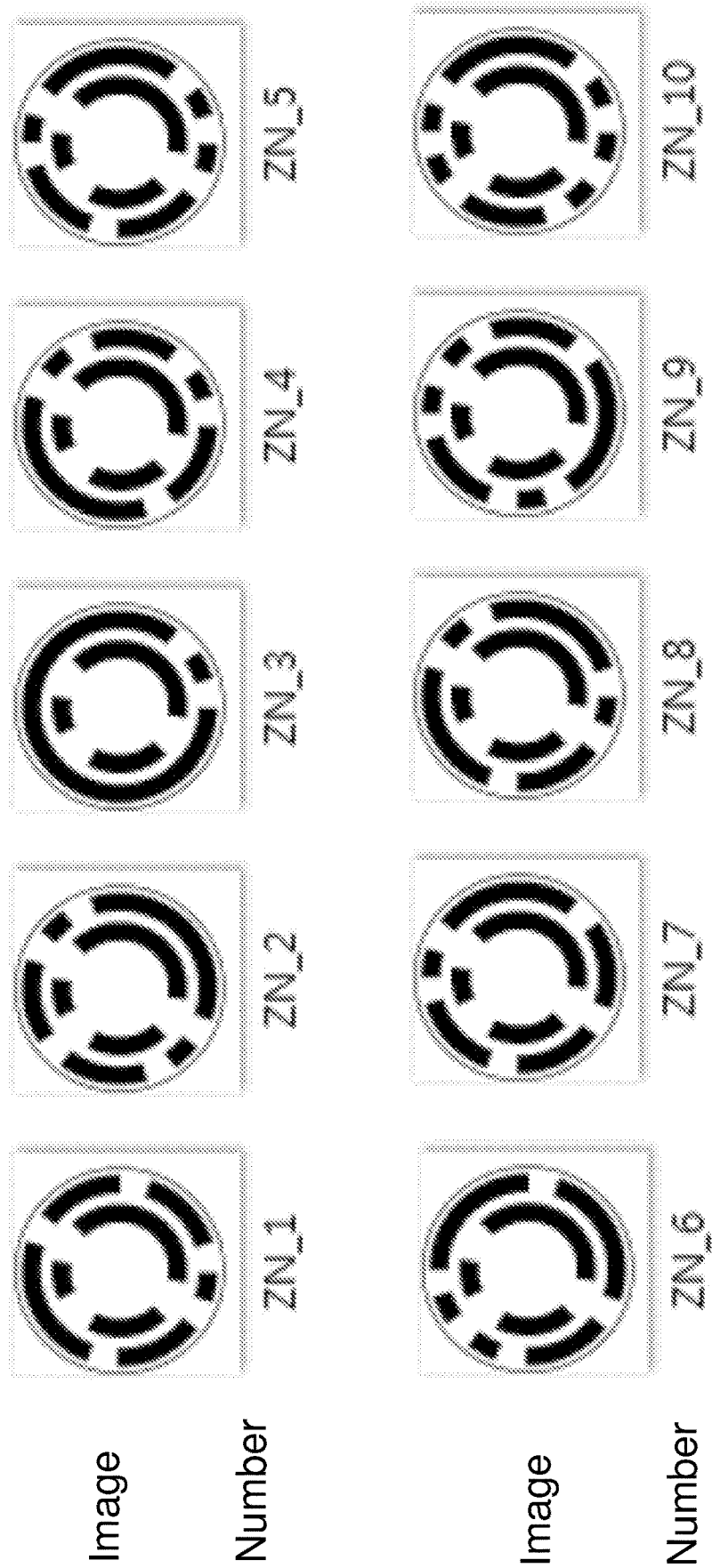
FIG. 4B shows examples of beads with a unique analog code, in accordance with some embodiments.

In some embodiments, the two-dimensional shape of the substantially non-transparent polymer layer comprises one or more rings enclosing the center portion of the substantially transparent polymer layer. In some embodiments, at least one of the one or more rings comprises a discontinuity. Exemplary and non-limiting two-dimensional shapes formed using one or more rings (e.g., two rings) having varying numbers and configurations of discontinuities are illustrated in FIG. 4B.

In some embodiments, the two-dimensional shape of the substantially non-transparent polymer layer comprises a gear shape. A gear shape as used herein may refer to a plurality of shapes (e.g., gear teeth) arrayed on the perimeter of a substantially round, elliptical, or circular body, where at least two of the shapes of the plurality are spatially separated. In some embodiments, the gear shape comprises a plurality of gear teeth. In some embodiments, the analog code is represented by one or more aspects selected from the height of one or more gear teeth of the plurality, the width of one or more gear teeth of the plurality, the number of gear teeth in the plurality, and the arrangement of one or more gear teeth within the plurality. Advantageously, a gear shape encompasses multiple aspects, including the height of gear teeth, the width of gear teeth, the number of gear teeth, and the arrangement of gear teeth, that may be varied in order to generate a large diversity of potential unique two-dimensional shapes. It is to be appreciated, however, that since the gear shapes of the present disclosure are used for encoding and are not required to physically intermesh with another gear (e.g., as with mechanical gears that transmit torque), gear teeth of the present disclosure are not constrained by the need for identical or intermeshing shapes, either within one gear shape or between multiple gear shapes. As such, the variety of shapes that may be considered a gear tooth of the present disclosure is significantly greater than with a mechanical gear.

In some embodiments, the plurality of gear teeth comprises one or more gear teeth that are between about 1 μm and about 10 μm wide. In some embodiments, the plurality of gear teeth comprises one or more gear teeth that are about 1 μm wide, about 1.5 μm wide, about 2 μm wide, about 2.5 μm wide, about 3 μm wide, about 3.5 μm wide, about 4 μm wide, about 4.5 μm wide, about 5 μm wide, about 5.5 μm wide, about 6 μm wide, about 6.5 μm wide, about 7 μm wide, about 7.5 μm wide, about 8 μm wide, about 8.5 μm wide, about 9 μm wide, about 9.5 μm wide, or about 10 μm wide. In some embodiments, the plurality of gear teeth comprises one or more gear teeth that are less than about any of the following widths (in μm): 10, 9.5, 9, 8.5, 8, 7.5, 7, 6.5, 6, 5.5, 5, 4.5, 4, 3.5, 3, 2.5, 2, or 1.5. In some embodiments, the plurality of gear teeth comprises one or more gear teeth that are greater than about any of the following widths (in μm): 1, 1.5, 2, 2.5, 3, 3.5, 4, 4.5, 5, 5.5, 6, 6.5, 7, 7.5, 8, 8.5, 9, or 9.5. That is, the plurality of gear teeth may comprise one or more gear teeth that can be any of a range of widths having an upper limit of 10, 9.5, 9, 8.5, 8, 7.5, 7, 6.5, 6, 5.5, 5, 4.5, 4, 3.5, 3, 2.5, 2, or 1.5 and an independently selected lower limit of 1, 1.5, 2, 2.5, 3, 3.5, 4, 4.5, 5, 5.5, 6, 6.5, 7, 7.5, 8, 8.5, 9, or 9.5, wherein the lower limit is less than the upper limit.

In some embodiments, the plurality of gear teeth comprises one or more gear teeth that are between about 1 µm and about 10 µm tall. In some embodiments, the plurality of gear teeth comprises one or more gear teeth that are about 1 µm tall, about 1.5 µm tall, about 2 µm tall, about 2.5 µm tall, about 3 µm tall, about 3.5 µm tall, about 4 µm tall, about 4.5 µm tall, about 5 µm tall, about 5.5 µm tall, about 6 µm tall, about 6.5 µm tall, about 7 µm tall, about 7.5 µm tall, about 8 µm tall, about 8.5 µm tall, about 9 µm tall, about 9.5 µm tall, or about 10 µm tall. In some embodiments, the plurality of gear teeth comprises one or more gear teeth that are less than about any of the following heights (in µm): 10, 9.5, 9, 8.5, 8, 7.5, 7, 6.5, 6, 5.5, 5, 4.5, 4, 3.5, 3, 2.5, 2, or 1.5. In some embodiments, the plurality of gear teeth comprises one or more gear teeth that are greater than about any of the following heights (in µm): 1, 1.5, 2, 2.5, 3, 3.5, 4, 4.5, 5, 5.5, 6, 6.5, 7, 7.5, 8, 8.5, 9, or 9.5. That is, the plurality of gear teeth may comprise one or more gear teeth that can be any of a range of heights having an upper limit of 10, 9.5, 9, 8.5, 8, 7.5, 7, 6.5, 6, 5.5, 5, 4.5, 4, 3.5, 3, 2.5, 2, or 1.5 and an independently selected lower limit of 1, 1.5, 2, 2.5, 3, 3.5, 4, 4.5, 5, 5.5, 6, 6.5, 7, 7.5, 8, 8.5, 9, or 9.5, wherein the lower limit is less than the upper limit. It is to be appreciated that a gear tooth may have different measurable heights, depending on the point of reference, if the adjacent perimeter segments from which the gear tooth extends are uneven (see, e.g., gear tooth 602 in FIG. 6C, which may be 4 or 6.5 µm tall, depending on the point of reference).

In some embodiments, the plurality of gear teeth comprises one or more gear teeth that are spaced between about 1 µm and about 10 µm apart. In some embodiments, the plurality of gear teeth comprises one or more gear teeth that are spaced about 1 µm apart, about 1.5 µm apart, about 2 µm apart, about 2.5 µm apart, about 3 µm apart, about 3.5 µm apart, about 4 µm apart, about 4.5 µm apart, about 5 µm apart, about 5.5 µm apart, about 6 µm apart, about 6.5 µm apart, about 7 µm apart, about 7.5 µm apart, about 8 µm apart, about 8.5 µm apart, about 9 µm apart, about 9.5 µm apart, or about 10 µm apart. In some embodiments, the plurality of gear teeth comprises one or more gear teeth that are spaced less than about any of the following widths apart (in µm): 10, 9.5, 9, 8.5, 8, 7.5, 7, 6.5, 6, 5.5, 5, 4.5, 4, 3.5, 3, 2.5, 2, or 1.5. In some embodiments, the plurality of gear teeth comprises one or more gear teeth that are spaced greater than about any of the following widths apart (in µm): 1, 1.5, 2, 2.5, 3, 3.5, 4, 4.5, 5, 5.5, 6, 6.5, 7, 7.5, 8, 8.5, 9, or 9.5. That is, the plurality of gear teeth may comprise one or more gear teeth that can be spaced any of a range of widths apart having an upper limit of 10, 9.5, 9, 8.5, 8, 7.5, 7, 6.5, 6, 5.5, 5, 4.5, 4, 3.5, 3, 2.5, 2, or 1.5 and an independently selected lower limit of 1, 1.5, 2, 2.5, 3, 3.5, 4, 4.5, 5, 5.5, 6, 6.5, 7, 7.5, 8, 8.5, 9, or 9.5, wherein the lower limit is less than the upper limit.

In some embodiments, a bead of the present disclosure is a substantially circular disc. As used herein, a substantially circular shape may refer to any shape having a roughly identical distance between all of the points of the shape's perimeter and the shape's geometric center. In some embodiments, a shape is considered to be substantially circular if the variation among any of the potential radii connecting the geometric center and a given point on the perimeter exhibit 10% or lesser variation in length. As used herein, a substantially circular disc may refer to any substantially circular shape wherein the thickness of the shape is significantly less than its diameter. For example, in some embodiments, the thickness of a substantially circular disc may be less than about 50%, less than about 40%, less than about 30%, less than about 20%, less than about 15%, less than about 10%, or less than about 5% of its diameter. In certain embodiments, the thickness of the substantially circular disc may about 20% of its diameter. It is to be appreciated that the beads of the present disclosure whose outline is a gear shape may also be considered substantially circular discs; for example, the shape of the bead excluding the one or more gear teeth may comprise a substantially circular disc.

In some embodiments, the bead is less than about 300 µm in diameter. For example, in some embodiments, the diameter of the bead is less than about 300 µm, less than about 200 µm, less than about 180 µm, less than about 160 µm, less than about 140 µm, less than about 120 µm, less than about 100 µm, less than about 80 µm, less than about 60 µm, less than about 40 µm, or less than about 20 µm. In some embodiments, the bead is spherical and measures about 300 µm in diameter. In other embodiments, the bead is rectangular and measures about 300 µm in diameter. In some embodiments, the bead is rectangular and measure about 40×60×5 µm.

In some embodiments, the diameter of the bead is about 180 µm, about 160 µm, about 140 µm, about 120 µm, about 100 µm, about 90 µm, about 80 µm, about 70 µm, about 60 µm, about 50 µm, about 40 µm, about 30 µm, about 20 µm, or about 10 µm. In certain embodiments, the bead is about 60 µm in diameter.

In some embodiments, the bead is less than about 50 µm in thickness. For example, in some embodiments, the thickness of the bead is less than about 70 µm, about 60 µm, about 50 µm, about 40 µm, about 30 µm, less than about 25 µm, less than about 20 µm, less than about 15 µm, less than about 10 µm, or less than about 5 µm. In some embodiments, the thickness of the bead is less than about any of the following thicknesses (in µm): 70, 65, 60, 55, 50, 45, 40, 35, 30, 25, 20, 15, 10, 9, 8, 7, 6, 5, 4, 3, or 2. In some embodiments, the thickness of the bead is greater than about any of the following thicknesses (in µm): 1, 2, 3, 4, 5, 6, 7, 8, 9, 10, 15, 20, 25, 30, 35, 40, 45, 50, 55, 60, or 65. That is, the thickness of the bead may be any of a range of thicknesses (in µm) having an upper limit of 70, 65, 60, 55, 50, 45, 40, 35, 30, 25, 20, 15, 10, 9, 8, 7, 6, 5, 4, 3, or 2 and an independently selected lower limit of 1, 2, 3, 4, 5, 6, 7, 8, 9, 10, 15, 20, 25, 30, 35, 40, 45, 50, 55, 60, or 65, wherein the lower limit is less than the upper limit.

In some embodiments, the thickness of the bead is about 50 µm, about 45 µm, about 40 µm, about 35 µm, about 30 µm, about 25 µm, about 20 µm, about 19 µm, about 18 µm, about 17 µm, about 16 µm, about 15 µm, about 14 µm, about 13 µm, about 12 µm, about 11 µm, about 10 µm, about 9 µm, about 8 µm, about 7 µm, about 6 µm, about 5 µm, about 4 µm, about 3 µm, about 2 µm, or about 1 µm. In certain embodiments, the bead is about 10 µm in thickness.

In some aspects, a bead of the present disclosure can comprise a capture agent. In some embodiments, the capture agent for a particular bead species may be a "unique capture agent," e.g., a capture agent is associated with a particular bead species having a particular identifier (e.g., analog code). The capture agent can be any biomolecule or a chemical compound capable of binding one or more analytes (such as a biomolecule or chemical compound) present in the solution. Examples of biomolecule capture agents include, but are not limited to, a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, a small molecule, a bacterial cell, a cellular organelle, and an antibody fragment.

Examples of chemical compound capture agents include, but are not limited to, individual components of chemical libraries, small molecules, or environmental toxins (for example, pesticides or heavy metals).

In some embodiments, the capture agent is coupled to a surface of the bead (in some embodiments, in at least a center portion of the bead surface). In some embodiments, the capture agent can be chemically attached to the bead. In other embodiments, the capture agent can be physically absorbed to the surface of the bead. In some embodiments, the attachment linkage between the capture agent and the bead surface can be a covalent bond. In other embodiments, the attachment linkage between the capture agent and the bead surface can be a non-covalent bond including, but not limited to, a salt bridge or other ionic bond, one or more hydrogen bonds, hydrophobic interactions, Van der Waals force, London dispersion force, a mechanical bond, one or more halogen bonds, aurophilicity, intercalation, or stacking.

In some aspects, more than one (such as two, three, four, five, six, seven, eight, nine, or ten) capture agents for the same analyte can each be associated with a bead described herein. In this embodiment, each capture agent for a particular analyte binds to the analyte with a different affinity as measured by the dissociation constant of analyte/capture agent binding. Accordingly, within a plurality of beads in a composition, there can be two or more subpopulations of beads with capture agents that bind to the same analyte, but wherein the capture agents associated with each subpopulation bind to the analyte with a different affinity. In some embodiments, the dissociation constant of the analyte for any of the capture agents is not greater than $10^{-6}$ M, such as $10^{-7}$M or $10^{-8}$M. In other embodiments, the dissociation constant of the analyte for any of the capture agents is from about $10^{-10}$ M to about $10^{-6}$ M, such from about $10^{-10}$ M to about $10^{-7}$M, about $10^{-10}$ M to about $10^{-8}$ M, about $10^{-10}$ M to about $10^{-9}$M, about $10^{-9}$ M to about $10^{-6}$M, about $10^{-9}$ M to about $10^{-7}$ M, about $10^{-9}$ M to about $10^{-8}$ M, about $10^{-8}$ M to about $10^{-6}$M, or about $10^{-8}$ M to about $10^{-7}$ M. In some embodiments, the dissociation constant of the analyte for any two capture agents differs by as much as about 3 $\log_{10}$, such as by as much as about 2.5 $\log_{10}$, 2 $\log_{10}$, 1.5 $\log_{10}$, or 1 $\log_{10}$.

In some embodiments, an analyte of the present disclosure is coupled to a bead for the capture of one or more analytes. In some embodiments, the one or more analytes may be captured from a sample, such as a biological sample described herein. In some embodiments, an analyte may include without limitation a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, a small molecule, a bacterial cell, a cellular organelle, and an antibody fragment. In other embodiments, the analyte is a chemical compound (such as a small molecule chemical compound) capable of binding to the capture agent such as individual components of chemical libraries, small molecules, or environmental toxins (for example, pesticides or heavy metals).

A sample of the present disclosure, e.g., a biological sample, can be in any form, including solid materials (e.g. tissue, cell pellets and biopsies) and biological fluids (e.g. urine, blood and components thereof such as serum, saliva, lymph, tears, sweat, prostatic fluid, seminal fluid, semen, bile, stool, mucus, amniotic fluid and mouth wash (containing buccal cells)). Solid materials typically are mixed with a fluid. Sample can also refer to an environmental sample such as water, air, soil, or any other environmental source. In some embodiments (as shown in Example 5 below), the sample comprises serum.

In some aspects, the analytes in a sample (such as a biological sample) can be labeled with a signal-emitting entity capable of emitting a detectable signal upon binding to the capture agent. In some embodiments, the signal-emitting entity can be colorimetric based. In other embodiments, the signal-emitting entity can be fluorescence-based including, but not limited to, phycoerythrin, blue fluorescent protein, green fluorescent protein, yellow fluorescent protein, cyan fluorescent protein, and derivatives thereof. In other embodiments, the signal-emitting entity can be radioisotope based, including, but not limited to, molecules labeled with $^{32}$P, $^{33}$P, $^{22}$Na, $^{36}$Cl, $^{2}$H, $^{3}$H, $^{35}$S, and $^{123}$I. In other embodiments, the signal-emitting entity is light-based including, but not limited to, luciferase (e.g., chemiluminescence-based), horseradish peroxidase, alkaline phosphatase, and derivatives thereof. In some embodiments, the biomolecules or chemical compounds present in the sample can be labeled with the signal-emitting entity prior to contact with the bead. In other embodiments, the biomolecules or chemical compounds present in the sample can be labeled with the signal-emitting entity subsequent to contact with the bead.

A. Shape of the Beads

The beads described herein can possess any three dimensional geometric shape. In some embodiments, the plurality of beads can be spherical, including semi-spherical, in shape. In other embodiments, the plurality of beads can be ovoid in shape. In some embodiments, the plurality of beads can be cubical in shape including, but not limited to, rectified cubes, rectangular cubes, truncated cubes, cantellated cubes, omnitruncated cubes, or snub cubes. In some embodiments, the plurality of beads can be cylindrical in shape including, but not limited to, right circular cylinders, elliptic cylinders, or oblique cylinders. In some embodiments, the plurality of beads can be conic in shape including, but not limited to, right circular cones or oblique circular cones. In some embodiments, the plurality of beads can be pyramidal in shape including, but not limited to, square pyramids or pentagonal pyramids. In some embodiments, the plurality of beads can be tetrahedral in shape. In some embodiments, the plurality of beads can be prismic in shape. Additionally, other embodiments of the plurality of beads can be any form of polyhedron including, but not limited to, dodecahedrons, icosidodecahedrons, rhombic triacontahedrons, or rhombic dodecahedrons.

In some aspects, the beads of some of the compositions described herein can have surfaces that are smooth and lack surface irregularities. As used herein, a bead is "smooth and lacks surface irregularities" if the distance from the gravitational center of any one bead in the composition to any two points on the surface of the bead varies by no more than about 10%. In some embodiments, the distance from the gravitational center of any one bead in the composition to any two points on the surface of the bead can vary by no more than about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, about 1%, about 0.5%, or about 0.25%, inclusive, as well as any numerical value in between these percentages. In some embodiments, microscopic examination can be used to determine that the bead surface is free from deep dents, holes, or high bumps.

B. Size of the Beads

In some aspects, the beads of the compositions described herein can be of substantially identical size and shape. As used herein, "substantially identical size" means that the variation between the distances measured at the widest dimension between any two beads (such as, polymeric beads) in a composition is less than about 10%. In some embodiments, the variation between the distances measured at the widest dimension between any two beads in a composition can be less than about 9%, about 8%, about 7%, about 6%, about 5%, about 4%, about 3%, about 2%, about 1%, about 0.5%, or about 0.25%, inclusive, as well as any numerical value in between these numbers. "Substantially identical shape," as used herein, means that each bead of a composition is the same shape as any other bead within the composition.

C. Identifiers

Each bead in the bead compositions described herein may be associated with one or more unique identifiers. In some embodiments, the identifier is an analog code identifier. In some aspects, the identifier corresponds to the identity of a capture agent immobilized to the surface of the bead (e.g., an antibody, a small molecule chemical compound, or a nucleic acid probe) for purposes of conducting a specific assay. In other aspects, the bead compositions described herein contain additional beads with analog code identifiers that can also be utilized for storing information (e.g., data) and/or performing other functions that are not directly related to the multiplex assays per se. For example, in some embodiments, the analog identifier is recognized by an imaging processor as a specific assay or assay kit, specific analyte, manufacturing lot, individual, locational identifier, or calibration signal.

In some embodiments, the bead compositions and systems comprise at least two beads, at least three beads, at least four beads, at least five beads, or at least six beads, each with an analog code identifier that is recognized by an imaging processor as a specific assay or assay kit, specific analyte, manufacturing lot, individual, locational identifier, or calibration signal. It is to be understood that each of the at least two beads, at least three beads, at least four beads, at least five beads, or at least six beads can have an analog code identifier that is recognized as a parameter independently selected from a specific assay or assay kit, specific analyte, manufacturing lot, individual, locational identifier, or calibration signal. That is to say, each of the beads can have a different identifier belonging to a different class of parameter. For example, at least two beads can be included: one with an identifier recognized as a specific assay, and one with an identifier recognized as a manufacturing lot; or one with an identifier recognized as a specific assay kit, and one with an identifier recognized as an individual. For another non-limiting example, at least three beads can be included: one with an identifier recognized as a calibration signal, one with an identifier recognized as locational identifier, and one with an identifier recognized as a specific analyte. For another non-limiting example, at least four beads can be included: one with an identifier recognized as a specific assay, one with an identifier recognized as locational identifier, one with an identifier recognized as a specific analyte, and one with an identifier recognized as a manufacturing lot. For another non-limiting example, at least five beads can be included: one with an identifier recognized as a specific assay, one with an identifier recognized as a specific assay kit, one with an identifier recognized as a specific analyte, one with an identifier recognized as a manufacturing lot, and one with an identifier recognized as a calibration signal. For another non-limiting example, at least six beads can be included: one with an identifier recognized as a specific assay, one with an identifier recognized as a specific analyte, one with an identifier recognized as a manufacturing lot, one with an identifier recognized as an individual, one with an identifier recognized as locational identifier, and one with an identifier recognized as a calibration signal.

Thus, in some embodiments, performing an assay may include identifying the capture agent coupled to each bead of a plurality of beads using an analog code identifier of the bead that corresponds to the identity of the capture agent and identifying one or more of the specific assay or assay kit, specific analyte, manufacturing lot, individual, locational identifier, and/or calibration signal using an analog code identifier with one or more additional bead(s). In one embodiment, the bead (such as, polymeric bead) compositions described herein contain at least one bead with an analog code identifier that is recognized by an imaging processor as corresponding to a particular biological or chemical multiplex assay. The assay identifier can also be used to store information related to a particular multiplex assay kit, including the function of all of the other beads in a composition contained within the kit (such as, but not limited to, the identity of capture agents associated with the beads in the composition or beads labeled with identifiers for purposes of calibrating the imaging processor used in conjunction with the assay).

In some embodiments, the bead compositions described herein contain at least one bead with an analog code identifier that is recognized by an imaging processor as corresponding to a particular manufacturing lot. The lot identifier can be used to store information related to the particular manufacturing lot of an assay kit, including the date of manufacture, expiration date, and external standard curves which can be used for calculating the concentration of one or more target analytes in a sample (such as a biological sample) to be assayed. In a further embodiment, external standard curves for each target analyte in a multiplex assay kit can be determined for each production lot and the data incorporated into software accompanying the multiplex assay kit each time a new manufacturing lot is produced. In yet another embodiment, data related to these pre-determined standard curves can be accessible over the internet by the imaging processor which can use them to calculate the concentration of one or more target analytes in a sample (such as a biological sample).

In some embodiments, the bead compositions described herein contain at least one bead with an analog code identifier that is recognized by an imaging processor as corresponding to an individual. The individual identifier can be used to store information related to, for example, individuals submitting samples for biological or chemical assay analysis or individuals ordering those assays to be performed, such as, but not limited to, a health care professional. As used herein, an "individual" can be a mammal, such as any common laboratory model organism. Mammals include, but are not limited to, humans and non-human primates, farm animals, sport animals, pets (such as dogs or cats), mice, rats, and other rodents. In some embodiments, an individual is a human. In other embodiments, an individual is a patient who has provided a biological sample to be biologically or chemically assayed. In another embodiment, an individual is a health care professional who ordered an assay to be performed. In yet another embodiment, the individual is a governmental agency or department.

In some embodiments, the bead compositions described herein contain at least one bead with an analog code identifier that is recognized by an imaging processor as corresponding to a location. The locational identifier can be used to store information related to locations related to the samples to be assayed or the location of the source of the samples to be assayed. Non-limiting examples of locational identifiers include hospitals, the offices of health care professionals, an address (such as the address of an individual, a hospital, or a health care professional), or a laboratory (such as a diagnostic laboratory, a medical laboratory, a university laboratory, or a research laboratory).

In some embodiments, the bead compositions described herein contain at least one bead with an analog code identifier that is recognized by an imaging processor as corresponding to a temporal identifier. Non-limiting examples of temporal identifiers include the date of specimen collection.

In some embodiments, the bead compositions described herein contain at least one bead with an analog code identifier that is recognized by an imaging processor as identifying the bead as a positive or negative control bead. The positive control bead may be, for example, a bead coated with biotinylated bovine serum albumin (BSA), or any other marker that may be used as a positive control. In some embodiments, the positive control bead is coated with biotin, and the positive control bead is detected using a signal-emitting entity conjugated to streptavidin or a derivative thereof (e.g., a streptavidin phycoerythrin conjugate). The negative control bead can be, for example, a bead coated with BSA, or any other marker that may be used as a negative control.

In some embodiments, the bead compositions described herein contain at least one bead that is pre-labeled for calibration of the imaging processor.

In some embodiments, the bead compositions described herein contain at least one bead with an analog code identifier that is recognized by an imaging processor as corresponding to more than one function or piece of information (such as but not limited to the particular biological or chemical multiplex assay, information related to a particular multiplex assay kit, information related to the particular manufacturing lot, an individual, a location). For example, the bead compositions described herein may contain at least one bead with an analog code identifier that is recognized by an imaging processor as corresponding to information regarding the manufacturing lot (including but not limited to the manufacturing date, expiration date, standard curves, and cut off values) as well as identifying the bead as a negative control bead. As another example, the bead compositions described herein may contain at least one bead with an analog code identifier that is recognized by an imaging processor as corresponding to information regarding the assay kit (including but not limited to the function of all of the other beads in the composition contained within the kit) as well as identifying the bead as a positive or negative control. As another example, the bead compositions described herein may contain at least one bead with an analog code identifier that is recognized by an imaging processor as corresponding to information regarding the manufacturing lot (including, but not limited to, the date of manufacture, expiration date, and external standard curves which can be used for calculating the concentration of one or more target analytes in a sample to be assayed) as well as identifying the bead as a positive or negative control. As another example, the bead compositions described herein may contain at least one bead with an analog code identifier that is recognized by an imaging processor as corresponding to the patient name and identifier, the hospital, the health care professional, the diagnostic laboratory, and the date of specimen collection. As yet another example, the bead compositions described herein may contain at least one bead with an analog code identifier that is recognized by an imaging processor as identifying the capture agent that is bound to the surface of the bead and as corresponding to information regarding the assay kit (including but not limited to the function of all of the other beads in the composition contained within the kit).

D. Capture Agents

In some aspects, the beads of the compositions described herein can be attached to a unique capture agent. By "unique capture agent," it is meant that each capture agent is associated with a specific bead having a particular identifier. The capture agent can be any biomolecule or a chemical compound capable of binding one or more biomolecules or chemical compounds present in the solution. Examples of biomolecule capture agents include, but are not limited to, a DNA molecule, a DNA-analog-molecule, an RNA-molecule, an RNA-analog-molecule, an amino-acid, a nucleotide, a protein, an enzyme, a lipid, a phospholipid, a carbohydrate moiety, a polysaccharide, an antigen, a virus, a cell, an antibody, or an antibody fragment. Examples of chemical compound capture agents include, but are not limited to, individual components of chemical libraries, small molecules, or environmental toxins (for example, pesticides or heavy metals). In some embodiments, the capture agent can be chemically attached the bead. In other embodiments, the capture agent can be physically absorbed to the surface of the bead. In some embodiments, the attachment linkage between the capture agent and the bead can be a covalent bond. In other embodiments, the attachment linkage between the capture agent and the bead can be a non-covalent bond including, but not limited to, a salt bridge or other ionic bond, one or more hydrogen bonds, hydrophobic interactions, van der Waals force, London dispersion force, a mechanical bond, one or more halogen bonds, aurophilicity, intercalation, or stacking.

In one aspect, the binding of an analyte (such as a signal-emitting entity-labeled chemical compound or biomolecule) to a capture agent-bound bead can be detected by any apparatus capable of detecting the presence of the signal-emitting entity (for example, an imagining processor). In some embodiments, flow cytometry can be used to detect the presence of the signal-emitting entity. Flow cytometry uses the principles of light scattering, light excitation, and emission from fluorochrome reporter molecules and can be used to generate specific multi-parameter data from beads bound to reporter-labeled chemical compounds or biomolecules. Bead compositions (such as those described herein) can be hydro-dynamically focused in a sheath of a buffer solution before intercepting an optimally focused light source. In some embodiments, a laser can be used as a light source in flow cytometry.

In some aspects, the bead compositions described herein can be used to detect the presence of a particular chemical compound or biomolecule in the solution. Accordingly, in some embodiments, the binding of the capture agent to a chemical compound or biomolecule in the solution can indicate the presence of the chemical compound or biomolecule in the solution.

In some aspects, the bead compositions described herein can be used to detect the concentration of a particular chemical compound or biomolecule in the solution. Accordingly, in some embodiments, the binding of the capture agent to a chemical compound or biomolecule in the solution indicates the concentration of the chemical compound or biomolecule in the solution.

In some aspects, the bead compositions described herein can be used to determine the binding affinity of the capture agent for a particular chemical compound or biomolecule in the solution. Accordingly, in some embodiments, the binding of the capture agent to a chemical compound or biomolecule in the solution indicates the binding affinity of the capture agent for a particular chemical compound or biomolecule in the solution.

E. Signal-Emitting Entities

In some aspects, analytes in a sample (such as a biological sample) that are capable of binding to a capture agent are labeled with a signal-emitting entity capable of emitting a detectable signal upon binding to the capture agent. In some embodiments, the signal-emitting entity can be colorimetric based. In other embodiments, the signal-emitting entity can be fluorescence-based including, but not limited to, phycoerythrin, blue fluorescent protein, green fluorescent protein, yellow fluorescent protein, cyan fluorescent protein, and derivatives thereof. In other embodiments, the signal-emitting entity can be radioisotope based, including, but not limited, to, molecules labeled with $^{32}P$, $^{33}P$, $^{22}Na$, $^{36}Cl$, $^{2}H$, $^{3}H$, $^{35}S$, and $^{123}I$. In other embodiments, the signal-emitting entity is light-based including, but not limited to, luciferase (e.g. chemiluminescence-based) horseradish peroxidase, alkaline phosphatase, and derivatives thereof. In some embodiments, the biomolecules or chemical compounds present in the sample can be labeled with the signal-emitting entity prior to contact with a bead (such as, polymeric bead) composition. In other embodiments, the biomolecules or chemical compounds present in the sample can be labeled with the signal-emitting entity subsequent to contact with a bead composition.

IV. Methods of Making Encoded Beads

Certain aspects of the present disclosure relate to methods for making an encoded bead, e.g., a bead described herein. The methods for making an encoded bead may include one or more of the bead features or aspects described herein, e.g., in section III above and/or the Examples that follow.

In some embodiments, the methods include depositing a substantially transparent polymer layer, where the substantially transparent polymer layer has a first surface and a second surface, the first and the second surfaces being parallel to each other In some embodiments, the first and the second surfaces that are parallel to each other may be the top and bottom surface of a single layer. Any suitable substantially transparent polymer known in the art or described herein may be used. In some embodiments, the substantially transparent polymer layer is deposited using spin coating.

In some embodiments, the substantially transparent polymer layer may be deposited on a substrate. Suitable substrates may include substrates used in standard semiconductor and/or micro-electro-mechanical systems (MEMS) fabrication techniques. In some embodiments, the substrate may comprise glass, silicon, quartz, plastic, polyethylene terephthalate (PET), an indium tin oxide (ITO) coating, or the like.

In some embodiments, a sacrificial layer may be deposited on the substrate, e.g., a substrate as described above. In some embodiments, the sacrificial layer may be made of a polymer, including without limitation polyvinyl alcohol (PVA) or OmniCoat™ (MicroChem; Newton, Mass.). Sacrificial layers may be applied, used, and dissolved or stripped, e.g., according to manufacturer's instructions.

In some embodiments, a substantially transparent polymer layer of the present disclosure is deposited on a sacrificial layer. To generate a planar bead surface using a substantially transparent polymer layer, the substantially transparent polymer layer may be deposited onto a planar sacrificial layer. To generate a bead surface with one or more columns projecting therefrom, a sacrificial layer (e.g., one deposited onto a substrate) may be patterned with one or more column-shaped holes or void areas, for example by using a standard lithographic process. In some embodiments, a substantially transparent polymer layer may be deposited over the sacrificial layer and optional substrate such that the layer is deposited in the one or more column-shaped holes or void areas. In some embodiments, another substantially transparent polymer layer may then be deposited over the sacrificial layer and the one or more column-shaped holes or void areas filled with the first substantially transparent polymer layer.

In some embodiments, a magnetic, substantially non-transparent layer of the present disclosure is deposited on the first surface of the substantially transparent polymer layer. In some embodiments, the magnetic, substantially non-transparent layer is deposited by sputtering. The magnetic, substantially non-transparent layer may be made of, e.g., any of the magnetic materials described herein. For example, in some embodiments, the magnetic, substantially non-transparent layer comprises nickel (e.g., elemental nickel, or an alloy thereof).

In some embodiments, the magnetic, substantially non-transparent layer may be etched to remove a portion of the magnetic, substantially non-transparent layer that is deposited over a center portion of the substantially transparent polymer layer. The magnetic, substantially non-transparent layer may be etched by any means known in the art. For example, in some embodiments, the magnetic, substantially non-transparent layer is etched by conventional wet etching. Exemplary dimensions, shapes, and optional asymmetries for a magnetic, substantially non-transparent layer are provided supra.

In some embodiments, a second substantially transparent polymer layer of the present disclosure is deposited over the magnetic, substantially non-transparent layer. In some embodiments, the second substantially transparent polymer layer has a first surface and a second surface that are parallel to each other (e.g., the top and bottom surface of a single layer). In some embodiments, the second surface is affixed to the magnetic, substantially non-transparent layer. In some embodiments, the second substantially transparent polymer layer is aligned with the first substantially transparent polymer layer and has a center portion that is aligned with the center portion of the substantially transparent polymer layer. Exemplary dimensions for the center portion of a substantially transparent polymer layer are provided supra.

In some embodiments, a substantially non-transparent polymer layer of the present disclosure is deposited on the first surface of the second substantially transparent polymer layer. In some embodiments, the substantially non-transparent polymer layer encloses the center portions of the first and the second substantially transparent polymer layers. In some embodiments, the substantially non-transparent polymer layer comprises a two-dimensional shape representing an analog code. Any of the two-dimensional shapes described or exemplified herein may be used, e.g., one or more rings comprising a discontinuity, or a gear shape of the present disclosure. In some embodiments, the substantially non-transparent polymer layer is deposited over the second substantially transparent polymer layer and etched (e.g., using a standard lithographic process) into the desired two-dimensional shape.

In some embodiments, one or more columns may be deposited on the substantially transparent polymer, e.g., on the first surface of the second substantially transparent polymer layer at a portion not covered by the substantially non-transparent polymer layer. The one or more columns may be deposited as described herein, e.g., using a standard lithographic process.

In some embodiments that employ an optional sacrificial layer and/or substrate of the present disclosure, the sacrificial layer may be dissolved or stripped, and/or the substrate may be removed, using a solvent. A variety of solvents useful for fabrication (e.g., in standard semiconductor or MEMS fabrication processes, such as photoresist removal) are known in the art. In some embodiments, the solvent is a photoresist stripper solvent, such as a DMSO- or 1-methyl-2-pyrrolidon (NMP)-based solvent. In some embodiments, the solvent is an AZ® photoresist stripper, such as AZ® 300T (AZ Electronic Materials; Somerville, N.J.).

In some embodiments, the methods include depositing a sacrificial layer of the present disclosure on a substrate of the present disclosure. Sacrificial layers, substrates, and suitable deposition methods are described, e.g., as above.

In some embodiments, a substantially non-transparent polymer layer of the present disclosure is deposited on the sacrificial layer. In some embodiments, the substantially non-transparent polymer layer has a first and a second surface that are parallel to each other (e.g., the top and bottom surface of a single layer). In some embodiments, the second surface is affixed to the sacrificial layer.

In some embodiments, the outline of the substantially non-transparent polymer layer is shaped into a two-dimensional shape representing an analog code, e.g., as described herein. The substantially non-transparent polymer layer may be shaped by any method known in the art or described herein, e.g., using a standard lithographic process including but not limited to spin coating, soft baking, UV exposure, etching, and hard baking.

In some embodiments, the sacrificial layer may be dissolved or stripped, and/or the substrate may be removed, using a solvent, e.g., as described above.

In other embodiments, a magnetic layer comprising a magnetic material of the present disclosure is deposited on the sacrificial layer. Exemplary magnetic materials, magnetic layer shapes/dimensions, and deposition methods related thereto are provided supra. For example, in some embodiments, the magnetic layer may be shaped into one or more columns, e.g., as illustrated by column 906. In other embodiments, the magnetic layer may be between two non-transparent polymer layers, e.g., embedded as illustrated by magnetic layer 704. The magnetic material may contain, e.g., any of the magnetic materials described herein. For example, in some embodiments, the magnetic material comprises nickel (e.g., elemental nickel, or an alloy thereof).

In some embodiments, a substantially non-transparent polymer layer of the present disclosure is deposited on the magnetic layer. In some embodiments, the substantially non-transparent polymer layer has a first and a second surface that are parallel to each other (e.g., the top and bottom surface of a single layer). In some embodiments, a surface (e.g., the second surface) of the substantially non-transparent polymer layer is affixed to the magnetic layer.

In some embodiments, the outline of the substantially non-transparent polymer layer is shaped into a two-dimensional shape representing an analog code, e.g., as described above.

In some embodiments, the sacrificial layer may be dissolved or stripped, and/or the substrate may be removed, using a solvent, e.g., as described above.

Exemplary bead shapes, dimensions, and optional features suitable for the methods described above are provided throughout the present disclosure.

In some embodiments, a capture agent may be coupled to a bead of the present disclosure, e.g., a bead described herein and/or a bead produced by any of the methods described herein. Any of the capture agents described herein, or any capture agent known in the art suitable for capturing an analyte described herein, may find use in the methods and/or beads of the present disclosure.

In some embodiments, the capture agent may be coupled to a polymer layer of the present disclosure, e.g., a substantially transparent or substantially non-transparent polymer layer described herein. In some embodiments, the capture agent may be coupled to one or both of a first or a second surface of the polymer layer. In some embodiments, the capture agent may be coupled to at least the center portion of the polymer layer (e.g., a center portion as described herein). In some embodiments, the polymer comprises an epoxy-based polymer or otherwise contains an epoxide group.

In some embodiments, coupling the capture agent involves reacting the polymer with a photoacid generator and light to generate a cross-linked polymer. In some embodiments, the light is of a wavelength that activates the photoacid generator, e.g., UV or near-UV light. Photoacid generators are commercially available from Sigma-Aldrich (St. Louis) and BASF (Ludwigshafen). Any suitable photoacid generator known in the art may be used, including without limitation triphenyl or triaryl sulfonium hexafluoroantimonate; triarylsulfonium hexafluorophosphate; triphenylsulfonium perfluoro-1-butanesulfonate; triphenylsulfonium triflate; Tris(4-tert-butylphenyl)sulfonium perfluoro-1-butanesulfonate or triflate; Bis(4-tert-butylphenyl) iodonium-containing photoacid generators such as Bis(4-tert-butylphenyl)iodonium perfluoro-1-butanesulfonate, p-toluenesulfonate, and triflate; Boc-methoxyphenyldiphenylsulfonium triflate; (tert-Butoxycarbonylmethoxynaphthyl)-diphenylsulfonium triflate; (4-tert-Butylphenyl)diphenylsulfonium triflate; diphenyliodonium hexafluorophosphate, nitrate, perfluoro-1-butanesulfonate, triflate, or p-toluenesulfonate; (4-fluorophenyl)diphenylsulfonium triflate; N-hydroxynaphthalimide triflate; N-hydroxy-5-norbornene-2,3-dicarboximide perfluoro-1-butanesulfonate; (4-iodophenyl)diphenylsulfonium triflate; (4-methoxyphenyl)diphenylsulfonium triflate; 2-(4-methoxystyryl)-4,6-bis(trichloromethyl)-1,3,5-triazine; (4-methylphenyl)diphenylsulfonium triflate; (4-methylthiophenyl) methyl phenyl sulfonium triflate; (4-phenoxyphenyl) diphenylsulfonium triflate; (4-phenylthiophenyl) diphenylsulfonium triflate; or any of the photoacid generators described in product-finder.basf.com/group/corporate/product-finder/de/literature-documentArand+Irgacure-Brochure-Photoacid+Generator+Selection+Guide-English.pdf. In some embodiments, the photoacid generator is a sulfonium-containing photoacid generator.

In some embodiments, coupling the capture agent involves reacting an epoxide of the cross-linked polymer with a functional group such as an amine, carboxyl, thiol, or the like. Alternatively, the epoxy group on the surface can be oxidized to hydroxyl group, which is subsequently used as initiation sites for graft polymerization of water soluble polymers such as poly(acrylic acid). The carboxyl groups in poly(acrylic acid) are then used to form covalent bonds with amino or hydroxyl groups in capture agents.

In some embodiments, coupling the capture agent involves reacting an epoxide of the cross-linked polymer with a compound that contains an amine and a carboxyl. In some embodiments, the amine of the compound reacts with the epoxide to form a compound-coupled, cross-linked polymer. Without wishing to be bound to theory, it is thought that the capture agent may be coupled to the polymer before the polymer is cross-linked; however, this may reduce the uniformity of the resulting surface. Any compound with a primary amine and a carboxyl group may be used. Compounds may include without limitation glycine, amino undecanoic acid, amino caproic acid, acrylic acid, 2-carboxyethyl acrylic acid, 4-vinylbenzoic acid, 3-acrylamido-3-methyl-1-butanoic acid, glycidyl methacrylate, and the like. In some embodiments, the carboxyl of the compound-coupled, cross-linked polymer reacts with an amine (e.g., a primary amine) of the capture agent to couple the capture agent to the substantially transparent polymer.

V. Methods Using Encoded Beads

Provided herein are methods using the beads as described herein for conducting biological or chemical multiplex assays.

A. Attachment of Capture Agents to Bead Surfaces

In some aspects, the methods for producing the plurality of bead compositions described herein can further include attaching a capture agent (such as, but not limited to, a chemical compound or biomolecule) to the surface of the beads. The epoxy groups on the surface of fabricated beads can be modified to facilitate attachment to various chemical compounds or biomolecules. Suitable biomolecules for attachment to the beads include, but are not limited to, a DNA molecule, a DNA-analog-molecule, an RNA-molecule, an RNA-analog-molecule, an amino-acid, a nucleotide, a protein, an enzyme, a lipid, a phospholipid, a carbohydrate moiety, a polysaccharide, an antigen, a virus, a cell, an antibody, a small molecule chemical compound, or an antibody fragment. Furthermore, any suitable chemical compound can be attached to the surface of the beads including, for example, individual components of multi-member chemical libraries. In other embodiments, one or more biomolecules or chemical compounds can be physically absorbed to the surface of the bead. In some embodiments, the attachment linkage between the chemical compound or biomolecule and the bead can be a covalent bond. In other embodiments, the attachment linkage between the chemical compound or biomolecule and the bead can be a non-covalent bond including, but not limited to, a salt bridge or other ionic bond, one or more hydrogen bonds, hydrophobic interactions, van der Waals force, London dispersion force, a mechanical bond, one or more halogen bonds, aurophilicity, intercalation, or stacking.

In one non-limiting embodiment, a carbonyl group can be introduced onto the surface of an epoxy polymeric bead by reacting with amino acids such as beta-alanine. These carboxyl functionalities can then be used to form covalent bonds with amino groups of any chemical compound or biomolecule. In another non-limiting embodiment, the epoxy groups on the surface of the beads can be treated with cystamine followed by reduction using dithiothreonine (DTT). This results in free thiol becoming available to form disulfide bonds with sulfhydral groups of any chemical compound or biomolecule. In another non-limiting embodiment, the polymer surface can be decorated with free amines by reacting the epoxy polymer with excess ethylenediamine. The resulting free amino groups will attach to chemical compounds or biomolecules via carboxyl groups. In yet another non-limiting embodiment, the epoxide on the surface can be hydrolyzed to form hydroxyl groups. These high density hydroxyl groups can then be silanized with various siloxanes. Silanization has been widely used in the chemical industry to create vast different kinds of surfaces, and there are many types of silanxones available commercially and known in the art. Silanization can therefore be used to create many different surfaces for attachment of chemical compounds or biomolecules to the surface of the bead compositions described herein. In some embodiments, large biomolecules, such as proteins can be attached to the beads by physical absorption due to formation of one or more non-covalent bonds including, but not limited to, one or more salt bridge or other ionic bond, one or more hydrogen bonds, hydrophobic interactions, van der Waals force, London dispersion force, a mechanical bond, one or more halogen bonds, aurophilicity, intercalation, or stacking between proteins and the surface properties of the beads. The attachment by physical absorption does not require any chemical reaction and is often used, for example, in the preparation of solid phase for immunoassays.

A combinatorial chemical library is a collection of multiple species of chemical compounds comprised of smaller subunits or monomers. Combinatorial libraries come in a variety of sizes, ranging from a few hundred to many hundreds of thousand different species of chemical compounds. There are also a variety of library types, including oligomeric and polymeric libraries comprised of compounds such as peptides, carbohydrates, oligonucleotides, and small organic molecules, etc. Such libraries have a variety of uses, such as immobilization and chromatographic separation of chemical compounds, as well as uses for identifying and characterizing ligands capable of binding an acceptor molecule or mediating a biological activity of interest.

Various techniques for synthesizing libraries of compounds on solid-phase supports are known in the art. Solid-phase supports are typically polymeric objects with surfaces that are functionalized to bind with subunits or monomers to form the compounds of the library. Synthesis of one library typically involves a large number of solid-phase supports.

To make a combinatorial library, solid-phase supports are reacted with one or more subunits of the compounds and with one or more numbers of reagents in a carefully controlled, predetermined sequence of chemical reactions. In other words, the library subunits are "grown" on the solid-phase supports. The larger the library, the greater the number of reactions required, complicating the task of keeping track of the chemical composition of the multiple species of compounds that make up the library. Thus, it is important to have methods and apparatuses which facilitate the efficient production of large numbers of chemical compounds, yet allow convenient tracking of the compounds over a number of reaction steps necessary to make the compounds.

The beads (such as, polymeric beads) of the compositions of the present disclosure are applicable to any type of chemical reaction that can be carried out on a solid support. Such chemical reactions include, but are not limited to, 2+2 cycloadditions including trapping of butadiene; [2+3] cycloadditions including synthesis of isoxazolines, furans and modified peptides; acetal formation including immobilization of diols, aldehydes and ketones; aldol condensation including derivatization of aldehydes, synthesis of propanediols; benzoin condensation including derivatization of aldehydes; cyclocondensations including benzodiazepines and hydantoins, thiazolidines, turn mimetics, porphyrins, phthalocyanines; Dieckmann cyclization including cyclization of diesters; Diels-Alder reaction including derivatization of acrylic acid; Electrophilic addition including addition of alcohols to alkenes; Grignard reaction including derivatization of aldehydes; Heck reaction including synthesis of disubstituted alkenes; Henry reaction including synthesis of nitrile oxides in situ (see 2+3 cycloaddition); catalytic hydrogenation including synthesis of pheromones and peptides (hydrogenation of alkenes); Michael reaction including synthesis of sulfanyl ketones, bicyclo[2.2.2]octanes; Mitsunobu reaction including synthesis of aryl ethers, peptidyl phosphonates and thioethers; nucleophilic aromatic substitutions including synthesis of quinolones; oxidation including synthesis of aldehydes and ketones; Pausen-Khand cycloaddition including cyclization of norbornadiene with pentynol; photochemical cyclization including synthesis of helicenes; reactions with organo-metallic compounds including derivatization of aldehydes and acyl chlorides; reduction with complex hydrides and tin compounds including reduction of carbonyl, carboxylic acids, esters and nitro groups; Soai reaction including reduction of carboxyl groups; Stille reactions including synthesis of biphenyl derivatives; Stork reaction including synthesis of substituted cyclohexanones; reductive amination including synthesis of quinolones; Suzuki reaction including synthesis of phenylacetic acid derivatives; and Wittig-Horner reactions including reactions of aldehydes, pheromones, and sulfanyl ketones.

References disclosing the synthesis of chemical libraries as well as the deconvolution of the individual compounds of those libraries onto individual solid phase supports (e.g., polymeric bead compositions such as those disclosed herein), can be found in U.S. Patent Application No. 2009/0032592; Needels et al., (1993), *Proc. Natl. Acad. Sci. USA* 90: 10700-10704; International Patent Application Publication No: WO 97/15390, the disclosures of each of which are incorporated by reference herein in their entireties.

B. Methods for Identifying One Bead Out of a Plurality of Beads

Provided herein are methods for identifying a single bead from the plurality of bead compositions described herein. When using the bead compositions described herein for multiplex screening assays, individual beads attached to a capture agent (e.g. a known chemical compound (such as an individual member of a combinatorial chemical library) or a known biomolecule) can be identified by virtue of the unique analog code identifier associated with each bead in the composition. In other embodiments, an analog code identifier associated with at least one bead in a plurality of beads (such as, polymeric beads) can be decoded by an imaging processor to identify other sources of information not strictly related to assay being conducted per se. These can include, but are not limited to, the identity of the assay, the manufacturing lot of the plurality of beads, or a locational identifier. In another embodiment, further identifiers associated with a bead in the plurality of beads can be pre-labeled for calibration of the imaging processor. In other embodiments, the identifier associated with a bead in a plurality of beads can be decoded by an imaging processor to identify more than one type of information, such as those described above.

Accordingly, in one aspect, a single bead can be identified by injecting a composition comprising a plurality of beads into a conduit comprising a width of less than twice the width of an individual bead, wherein each bead in the composition is of substantially identical size and shape, and comprises at least one (such as, at least one, two, three, or four) unique analog code identifiers followed by the step of identifying the identifier.

1. Conduits

In some aspects, the methods described herein can utilize a conduit for individually guiding or funneling a composition of a plurality of beads, such as those described herein, to an imaging processor. The conduit can be constructed in such a way as to permit only one bead to interact with the imaging processor at any one time. In one embodiment, the conduit can have (i) large openings at a first end and (ii) small openings at a second end. In another embodiment, the conduit can have a width of less than twice the width of an individual polymeric bead at its widest dimension. In some embodiments, the conduit can have a first end large enough to permit injection of a plurality of beads, such as those described herein, into the conduit. In some embodiments, the first end large enough to permit injection of a plurality of beads is located at an elevation lower than the second end, causing the plurality of bead composition to flow upwards against the force of gravity.

The transverse shape of the conduit can be any shape sufficient to accommodate the shape of the plurality of beads of substantially identical size and shape, such as the compositions described herein, that are injected into the conduit. Accordingly, the transverse shape of the conduit can be, without limitation, square, circular, rectangular, triangular, ovoid, or any other shape sufficiently identical to the beads described herein.

The conduit can be made of any suitable material including, but not limited to, steel, non-ferrous metals (e.g. aluminum, copper, tin and alloys thereof), plastic material (e.g., PE, PP. PVC, ABS), or plastic (GRP), or other materials such as, glass, fiber cement, or ceramic.

The conduit can be located near an imaging processor, to allow the imaging processor to identify the one or more identifiers associated with a bead passing near the imaging processor. In some embodiments, the conduit can be located about 300 mm or less from the imaging processor. In some embodiments, the conduit can be located between about 200-300 mm or about 100-200 mm, inclusive from the imaging processor. In other embodiments, the conduit can be located about 90 mm, about 80 mm, about 70 mm, about 60 mm, about 50 mm, about 40 mm, about 35 mm, about 30 mm, about 25 mm, about 20 mm, about 15 mm, about 14 mm, about 13 mm, about 12 mm, about 11 mm, about 10 mm, about 9 mm, about 8 mm, about 7 mm, about 6 mm, about 5 mm, about 4 mm, about 3 mm, about 2 mm, about 1 mm, 0.9 mm, 0.8 mm, 0.7 mm, 0.6 mm, 0.5 mm, 0.4 mm, 0.2 mm, or 0.1 mm, inclusive, including any value between these numbers, from the imaging processor. In another embodiment, the conduit can be located about 0.5 mm to about 1 mm from the imaging processor.

2. Encoded Pattern Readers

A. Microfluidic-Based Imaging Processors

In another aspect of the present disclosure, a microfluidic apparatus can be used in conjunction with an imaging processor to decode an encoded pattern or a combination of encoded patterns associated with a bead (such as any of the beads disclosed herein). The microfluidic apparatus comprises a conduit, such as a micro flow channel, sized and configured to guide coded beads to advance one at a time pass a decoding zone associated with the imaging processor. The decoding zone includes a code detector (such as a light scanner, a CCD sensor, etc.) that detects the pattern of transmitted light through each coded bead for decoding the code represented by the image thereon. The conduit of the microfluidic apparatus has an internal cross section that has a geometry that is sized and shaped to receive and allow the encoded bead to pass through when a particular cross section of the coded bead is aligned with the cross section of the conduit, thereby presenting the encoded bead in a particular orientation with respect to the decoding zone. In one embodiment, the geometry of the internal cross section of the conduit is sized and shaped to receive and allow the encoded bead to pass through when the smallest cross section of the encoded bead is aligned with the conduit (e.g., the long axis of the coded bead is aligned with the axis of the conduit). The microfluidic apparatus can include more than one conduit, to provide decoding of encoded beads in parallel channels.

A decoding system associated with the imaging processor, positioned with respect to the decoding zone, includes a light source and an optical sensor. In one embodiment, the light source can be a diode laser at any of 200 nm, 250 nm, 300 nm, 350 nm, 400 nm, 450 nm, 500 nm, 550 nm, 600 nm, 650 nm, 700 nm, 750 nm, 800 nm, 850 nm, or 900 nm wavelengths, inclusive, including wavelengths in between these values. In another embodiment, the decoding system has an objective lens (such as a 5×, 10×, 15×, 20×, 25×, 30×, 35×, 40×, 45×, 50×, 55×, 60×, 65×, 70×, 75×, 80×, 85×, 90×, 95×, or 100× objective lens, inclusive, including any number in between these values). In another embodiment, the optical sensor can be a high-speed photon detector and include digital readout electronics. Alternatively, an area light source (e.g., a laser beam having a large enough spot size) can be used to project light to simultaneously cover the entire area of the encoded pattern of the bead, and an area optical sensor such as a CCD sensor can be used to image simultaneously the entire coded pattern and the light transmitted there through. Alternatively, a line scan camera can be used for the optical sensor.

As the beads pass through the decoding zone associated with the imaging processor, light from the laser is transmitted through and the light intensity is detected, by the photon detector and directly converted into 1's and 0's using threshold detection. The position of the slits on the bead determines which of the bits is the least significant bit (LSB) and the most significant bit (MSB). In some embodiments, a slight orientation variation of the bead in the confined conduit does not significantly affect the efficiency of the optical detection and subsequent decoding.

In a further embodiment, the imaging processor can also comprise a reaction detection system (e.g., a fluorescence detector, an absorption detector, or a chemiluminescence detector) for detecting the result of reactions that have taken place between an analyte in a sample and the capture agent immobilized to the surface of the bead. In some embodiments, a signal-emitting entity can be used for detection of a positive or negative reaction between an analyte and the capture agent and the signal emitted from the signal emitting entity detected by the reaction detection system. The signal-emitting entity can be, without limitation, a fluorescence label, chemiluminescence label or other light-emitting label, an absorption label, or a radioactive label. Thus, for example, in configurations employing fluorescent signal-emitting entities, the reaction detection system can include a light source that produces light at an appropriate wavelength for activating the fluorescent material, as well as optics for directing the light source through an optically clear detection window for observing material in the sample cell. The light source can be any number of light sources that provide one or more appropriate wavelengths, including, e.g., lasers, laser diodes, and LEDs. Other light sources can be used in other detection systems. For example, broad band light sources can be employed in light scattering/transmissivity detection schemes, and the like.

In some aspects, any of the beads described herein can be magnetic. In one embodiment, an electromagnet can be used to temporarily immobilize the bead for decoding of one or more encoded patterns associated with the bead by the imaging processor.

B. Analog Code Decoding by Image Processing Method

In some embodiments, the methods include decoding a first analog code and a second analog code using analog shape recognition to identify a first bead and a second bead. Conceptually, this decoding may involve imaging the analog code of each bead (e.g., in a solution or sample), comparing each image against a library of analog codes, and matching each image to an image from the library, thus positively identifying the code. Optionally, as described herein, when using beads that include an orientation indicator (e.g., an asymmetry), the decoding may further include a step of rotating each image to align with a particular orientation (based in part, e.g., on the orientation indicator). For example, if the orientation indicator includes a gap, the image could be rotated until the gap reaches a predetermined position or orientation (e.g., a 0° position of the image).

Various shape recognition software, tools, and methods are known in the art. Examples of such APIs and tools include without limitation Microsoft® Research FaceSDK, OpenBR, Face and Scene Recognition from ReKognition, Betaface API, and various ImageJ plugins. In some embodiments, the analog shape recognition may include without limitation image processing steps such as foreground extraction, shape detection, thresholding (e.g., automated or manual image thresholding), and the like.

It will be appreciated by one of skill in the art that the methods and beads described herein may be adapted for various imaging devices, including without limitation a microscope, plate reader, and the like. In some embodiments, decoding the analog codes may include illuminating the first and second beads by passing light through the substantially transparent portions (e.g., substantially transparent polymer layer(s)) of the first and second beads and/or the surrounding solution. The light may then fail to pass through, or pass through with a lower intensity or other appreciable difference, the substantially non-transparent portions (e.g., substantially non-transparent polymer layer(s)) of the first and second beads to generate a first analog-coded light pattern corresponding to the first bead and a second analog-coded light pattern corresponding to the second bead.

As described supra, any type of light microscopy may be used for the methods of the present disclosure, including without limitation one or more of: bright field, dark field, phase contrast, differential interference contrast (DIC), Nomarski interference contrast (NIC), Nomarski, Hoffman modulation contrast (HMC), or fluorescence microscopy. In certain embodiments, the analog codes may be decoded using bright field microscopy, and analyte(s) may be detected using fluorescence microscopy.

In some embodiments, decoding the analog codes may further include imaging the first analog-coded light pattern to generate a first analog-coded image and imaging the second analog-coded light pattern to generate a second analog-coded image. That is to say, the pattern of imaged light may correspond to the pattern of substantially transparent/substantially non-transparent areas of the bead, thus producing an image of the analog codes. This imaging may include steps including without limitation capturing the image, thresholding the image, and any other image processing step desired to achieve more accurate, precise, or robust imaging of the analog codes.

In some embodiments, decoding the analog codes may further include using analog shape recognition to match the first analog-coded image with the first analog code and to match the second analog-coded image with the second analog code. In some embodiments, an image may be matched with an analog code (e.g., an image file from a library of image files, with each image file corresponding to a unique two-dimensional shape/analog code) within a predetermined threshold, e.g., that tolerates a predetermined amount of deviation or mismatch between the image and the exemplar analog code image. Such a threshold may be empirically determined and may naturally be based on the particular type of two-dimensional shapes used for the analog codes and the extent of variation among the set of potential two-dimensional shapes.

3. Bead Fluorescence Detection

When a positive fluorescence signal is detected by the imaging processor, it indicates a positive reaction. In some embodiments, the reaction detector of the imaging processor comprises a light source, an optical filter, and a detector. The choice of light source depends on the fluorophore or fluorophores used in the assays and as identifiers for the capture agents immobilized to the surface of the beads. For example, red diode laser (665 nm), and compact Argon Laser (488 nm) or Helium laser, can be the light source for Picogreen and Cy 5.5 fluorophore. An optical filter can remove the reflected excitation light that is mixed in the fluorescence (e.g., Picogreen: 525 nm filter and Cy5.5: 694 nm filter). Cy 3 and Cy5 are commonly used fluorescence dyes; they can be excited with green light (530 nm) and red light (635 nm), respectively. The fluorescence intensity is commonly measured with a photomultiplier tube as the detector.

In another further embodiment, the imaging processor can also comprise a reaction detection system (e.g., a fluorescence detector, an absorption detector, or a chemiluminescence detector) for detecting the result of reactions that have taken place between an analyte in a sample and the capture agent immobilized to the surface of the bead. In some embodiments, a signal-emitting entity can be used for detection of a positive or negative reaction between an analyte and the capture agent and the signal emitted from the signal emitting entity detected by the reaction detection system. The signal-emitting entity can be, without limitation, a fluorescence label, chemiluminescence label or other light-emitting label, an absorption label, or a radioactive label. Thus, for example, in configurations employing fluorescent signal-emitting entities, the reaction detection system can include a light source that produces light at an appropriate wavelength for activating the fluorescent material, as well as optics for directing the light source through an optically clear detection window for observing material in the sample cell. The light source can be any number of light sources that provide one or more appropriate wavelengths, including, e.g., lasers, laser diodes, and LEDs. Other light sources can be used in other detection systems. For example, broad band light sources can be employed in light scattering/transmissivity detection schemes, and the like.

In some aspects, the beads of any of the compositions described herein can be magnetic. In one embodiment, an electromagnet can be used to temporarily immobilize the bead for detection of fluorescent light.

4. Machine Readable Formats for Supplying the Identity of Individual Beads

In some aspects of the methods provided herein, any of the unique analog code identifiers associated with any of the beads disclosed herein can be identified by an imaging processor (such as any of the imaging processors described herein) and data corresponding to the identification stored on a fixed or data storage medium that is accessible via a system for reading the storage medium. In other aspects, the imaging processor further comprises a reaction detection system for detecting the binding of an analyte in a sample (such as a biological sample) by analyzing the binding of the analyte to the capture agent immobilized on the surface of the bead and data corresponding to the detected reaction stored on a fixed or data storage medium that is accessible via a system for reading the storage medium. The analog code identifiers may identify, e.g., the capture agent of a bead, or the specific assay/assay kit, specific analyte, manufacturing lot, individual, locational identifier, or calibration signal. For example, using the analog code identifiers, the imaging processor may identify the capture agent on each bead of a plurality of beads and identify one or more of a specific assay or assay kit, specific analyte, manufacturing lot, individual, locational identifier, or calibration signal using another analog code identifier of a different bead. In some embodiments, the identification of the capture agent of a bead may be associated with one or more measurements, e.g., detecting the binding of an analyte in a sample to the capture agent.

In some embodiments, for example, a system for reading a data storage medium can include a computer including a central processing unit ("CPU"), a working memory which can be, e.g., RAM (random access memory) or "core" memory, mass storage memory (such as one or more disk drives or CD-ROM drives), one or more display devices (e.g., cathode-ray tube ("CRT") displays, light emitting diode ("LED") displays, liquid crystal displays ("LCDs"), electroluminescent displays, vacuum fluorescent displays, field emission displays ("FEDs"), plasma displays, projection panels, etc.), one or more user input devices (e.g., keyboards, microphones, mice, touch screens, etc.), one or more input lines, and one or more output lines, all of which are interconnected by a conventional bidirectional system bus. The system can be a stand-alone computer, or can be networked (e.g., through local area networks, wide area networks, intranets, extranets, or the internet) to other systems (e.g., computers, hosts, servers, etc.). The system can also include additional computer controlled devices such as consumer electronics and appliances.

Input hardware can be coupled to the computer by input lines and can be implemented in a variety of ways. Machine-readable data of the present disclosure can be inputted via the use of a modem or modems connected by a telephone line or dedicated data line. Alternatively or additionally, the input hardware can include CD-ROM drives or disk drives. In conjunction with a display terminal, a keyboard can also be used as an input device.

Output hardware can be coupled to the computer by output lines and can similarly be implemented by conventional devices. By way of example, the output hardware can include a display device for displaying a graphical representation of an active site of the present disclosure using a program such as QUANTA. Output hardware might also include a printer, so that hard copy output can be produced, or a disk drive, to store system output for later use.

Machine-readable storage devices useful in the present disclosure include, but are not limited to, magnetic devices, electrical devices, optical devices, and combinations thereof. Examples of such data storage devices include, but are not limited to, hard disk devices, CD devices, digital video disk devices, floppy disk devices, removable hard disk devices, magneto-optic disk devices, magnetic tape devices, flash memory devices, bubble memory devices, holographic storage devices, and any other mass storage peripheral device. It should be understood that these storage devices include necessary hardware (e.g., drives, controllers, power supplies, etc.) as well as any necessary media (e.g., disks, flash cards, etc.) to enable the storage of data.

A person having skill in the art will appreciate that any other method or technique to communicate or store data is also contemplated for providing the unique identification code transmitted by an RFID chip from an individual polymeric bead in a machine readable format.

C. Methods for Conducting Multiplex Assays

Provided herein are methods for conducting multiplex biological or chemical assays using the beads as described herein. Beads can be functionalized and bound with unique capture agents that specifically bind to one or more analytes (such as, but not limited to, chemical compounds or biomolecules in a sample (such as a biological sample)). Multiple capture agents can be functionalized to multiple beads within a single composition. However, each capture agent will be identifiable by an imaging processor based on the analog code identifier associated with each individual bead.

In some aspects, a plurality of capture agent-bound beads can be added to a sample which contains one or more analytes followed by identification of one or more capture agents by an imaging processor based on the identity of the identifier associated with an individual bead. The multiplex assay can further include additional beads in the composition with identifier(s) for purposes of specific information storage including, but not limited to, identification of the manufacturing lot number for the beads, identification of the assay for which the beads will be used, identification of a location, and/or identification of an individual. These beads and/or further beads in the composition can be labeled with identifiers for purposes of calibrating the imaging processor and or reaction detection system associated with the imaging processor.

In some aspects, information corresponding to any of the identifiers associated with individual beads in a plurality of beads (such as any of the beads of any of the bead compositions described herein) can be programmed to a memory, such as a computer. As used herein, a "memory" is a data storage unit (or medium) with programmable memory, preferably a non-volatile memory. As used herein, "programming" refers to the process by which data or information corresponding to a particular identifier is entered and stored in a memory. A memory that is programmed is a memory that contains retrievable information. It includes any means needed or used for writing to and reading from the memory. A "computer" is an instrument that has been programmed with or includes information (i.e., a key) specifying a code used to encode the identifiers. This instrument, or one linked thereto, transmits the programed information and signals to the imaging processor and it receives information transmitted from the imaging processor upon receipt of the appropriate signal. The computer thus creates the appropriate signal to transmit to the imaging processor and can also interpret transmitted signals. For example, if a "1" is stored at position 1,1 in the memory of the computer, upon receipt of this corresponding information from the imaging processor, the computer can determine that this means the identifier corresponding to a capture agent is, for example, a peptide containing alanine at the N-terminus, an organic group, organic molecule, oligonucleotide or whatever this information has been predetermined to mean. In another embodiment, upon receipt of this corresponding information from the imaging processor, the computer can determine that this means the identifier corresponds to the identity of a manufacturing lot, a locational identifier, or an individual, or whatever this information has been predetermined to mean. Alternatively, the information sent to and transmitted from the computer can be encoded into the appropriate form by an individual. In some embodiments, the computer is a remote computer that is accessible by a remote accessibility means, for example, the internet. In other embodiment, the computer is programmed information (i.e., a key) specifying a code used to encode the identifiers via software provided by an external source (such as, but not limited to, a compact disk, a CD-ROM, or a downloadable program obtained over the internet).

In other aspects, the imaging processor comprises a reaction detection system for detecting the binding of an analyte in a sample (such as a biological sample). In some embodiments, the reaction detection system analyzes the binding of the analyte to the capture agent immobilized on the surface of a bead in a plurality of beads and data corresponding to the detected reaction is transmitted to a computer. The detection system can be operably coupled to a computer, e.g., via an analog to digital converter, for transmitting detected signal data to the computer for analysis, storage, data manipulation, or integration with other information obtained from the identification of identifiers by the imaging processor. The computer can integrate and store information related to the identity of the identifier associated with the capture agent with information related to the binding of an analyte to the capture agent that is detected by the reaction detection system. In another embodiment, the computer integrates and stores information related to the identity of the identifier associated with the capture agent with information related to the binding of an analyte to the capture agent that is detected by the reaction detection system along with information obtained from one or more bead present within the plurality of beads (such as, polymeric beads) with an identifier that is recognized by the imaging processor as corresponding to, without limitation, a manufacturing lot, a locational identifier, and/or an individual.

Figure 14:
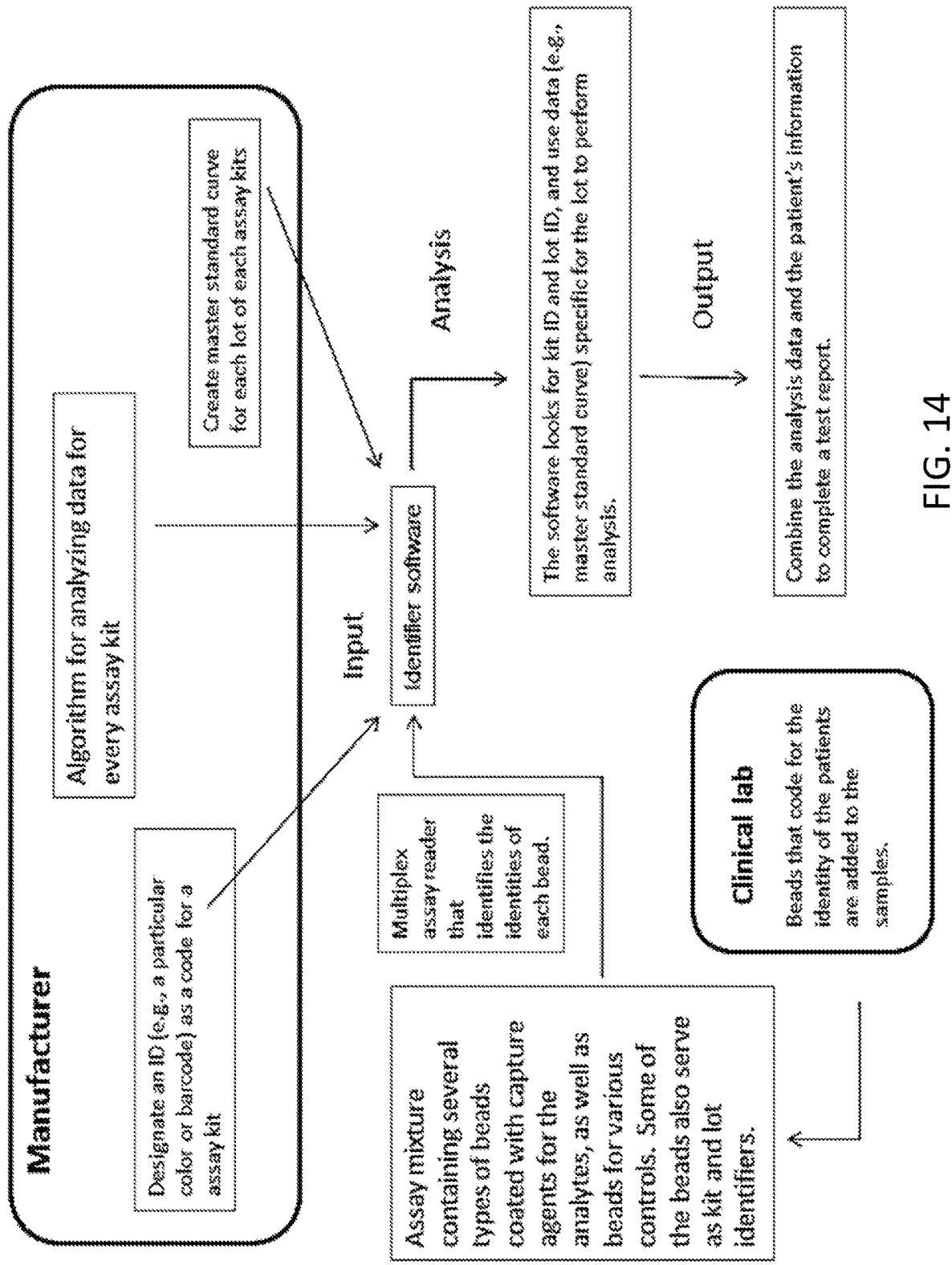
FIG. 14 depicts an exemplary method for use of the bead compositions encoded with unique identifiers described herein.

In another embodiment of the present disclosure, the analysis is multiplexed, that is, each sample is analyzed so that a signal from the signal emitting entity is detected by the reaction detection system for at least 2 analytes of interest, at least 3 analytes of interest, at least 4 analytes of interest, at least 5 analytes of interest, at least 10 analytes of interest, at least 15 analytes of interest, at least 20 analytes of interest, at least 25 analytes of interest, at least 30 analytes of interest, at least 35 analytes of interest, at least 40 analytes of interest, at least 45 analytes of interest, or at least 50 analytes of interest, or more. In one embodiment, the data are then subjected to an iterative minimization of error algorithm that takes into account variance between the datasets obtained from replicates, for example using least squares, least absolute error, etc.; and/or a monotone transformation algorithm that stabilizes the variability of the data and considers background measurements. An exemplary method for use of the compositions of beads encoded with unique identifiers is illustrated in FIG. 14.

Accordingly, provided herein is a method for conducting a multiplex assay comprising the steps of: a) contacting a sample with beads in an assay system, wherein each bead in the system comprises (1) a substantially transparent polymer layer having a first surface and a second surface, the first and the second surfaces being parallel to each other; (2) a substantially non-transparent polymer layer, wherein the substantially non-transparent polymer layer is affixed to the first surface of the substantially transparent polymer layer and encloses a center portion of the substantially transparent polymer layer, and wherein the substantially non-transparent polymer layer comprises a two-dimensional shape representing an analog code identifier; wherein the system comprises (i) at least one bead with an analog code identifier that is recognized by an imaging processor as a specific assay or assay kit, specific analyte, manufacturing lot, individual, locational identifier, or calibration signal, and (ii) a plurality of beads, wherein each bead of the plurality of beads comprises a capture agent that specifically binds to an analyte, wherein the capture agent is immobilized on at least one of the first surface and the second surface of the substantially transparent polymer layer in at least the center portion of the substantially transparent polymer layer, and wherein each bead of the plurality of beads comprises an analog code identifier corresponding to the capture agent; and simultaneously or sequentially, in any order: b) identifying the identifier that is recognized by the imaging processor as the specific assay; and c) detecting the binding of the analyte in the sample by analyzing the binding of the analyte to the capture agent immobilized on the surface of the bead based on the identification of the analog code identifier corresponding to the capture agent.

In some embodiments, the system further comprises (iii) at least two beads, at least three beads, at least four beads, at least five beads, or at least six beads, each with an analog code identifier that is recognized by an imaging processor as a specific assay or assay kit, specific analyte, manufacturing lot, individual, locational identifier, or calibration signal. In some embodiments, the system further comprises (iv) at least one bead recognized by the imaging processor as a positive or negative control. In some embodiments, the locational identifier corresponds to a hospital, a diagnostic laboratory, an address, a health care professional's office, or a research laboratory. In some embodiments, the system further comprises (v) at least one bead that is pre-labeled for monitoring functions of the imaging processor. In some embodiments, the beads comprise a spherical or rectangular shape. In some embodiments, the beads are less than about 300 µm in diameter. In some embodiments, the surface of the bead is smooth and lacks surface irregularities. In some embodiments, at least one surface of the bead comprises at least one site for chemical attachment of the capture agent. In some embodiments, the capture agent is selected from the group consisting of: a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, and an antibody fragment. In some embodiments, the plurality of beads are magnetic or non-magnetic.

In some embodiments, the beads further comprise: (3) a magnetic, substantially non-transparent layer that encloses the center portion of the substantially transparent polymer layer between the substantially non-transparent polymer layer and the center portion of the substantially transparent polymer layer, wherein the magnetic, substantially non-transparent layer is affixed to the first surface or the second surface of the substantially transparent polymer layer. In some embodiments, the beads further comprise: (4) a second substantially transparent polymer layer aligned with the first substantially transparent polymer layer, the second substantially transparent polymer layer having a center portion that is aligned with the center portion of the first substantially transparent polymer layer, wherein the second substantially transparent polymer layer is affixed to the second surface of the first substantially transparent polymer layer and does not extend beyond the two-dimensional shape of the first substantially transparent polymer layer; and (5) a magnetic, substantially non-transparent layer that encloses the center portion of the first substantially transparent polymer layer between the substantially non-transparent polymer layer and the center portion of the substantially transparent polymer layer, wherein the magnetic, substantially non-transparent layer is affixed between the first and the second substantially transparent polymer layers. In some embodiments, the beads further comprise an orientation indicator for orienting the analog code of the substantially non-transparent polymer layer. In some embodiments, the orientation indicator comprises an asymmetry of the magnetic, substantially non-transparent layer. In some embodiments, the magnetic, substantially non-transparent layer comprises nickel. In some embodiments, the magnetic, substantially non-transparent layer is between about 50 nm and about 10 µm in thickness. In some embodiments, the magnetic, substantially non-transparent layer is about 0.1 µm in thickness. In some embodiments, the two-dimensional shape of the substantially non-transparent polymer layer comprises one or more rings enclosing the center portion of the substantially transparent polymer layer, wherein at least one of the one or more rings comprises a discontinuity. In some embodiments, the two-dimensional shape of the substantially non-transparent polymer layer comprises a gear shape comprising a plurality of gear teeth, and wherein the analog code is represented by one or more aspects selected from the group consisting of the height of one or more gear teeth of the plurality, the width of one or more gear teeth of the plurality, the number of gear teeth in the plurality, and the arrangement of one or more gear teeth within the plurality. In some embodiments, the plurality of gear teeth comprises one or more gear teeth that are between about 1 µm and about 10 µm wide. In some embodiments, the plurality of gear teeth comprises one or more gear teeth that are between about 1 µm and about 10 µm tall. In some embodiments, the plurality of gear teeth comprises two or more gear teeth that are spaced between about 1 µm and about 10 µm apart. In some embodiments, the beads further comprise: (6) one or more columns projecting from the first surface of the first substantially transparent polymer layer, wherein the one or more columns are not within the center portion of the first substantially transparent polymer layer; and/or (7) one or more columns projecting from the second surface of the first substantially transparent polymer layer or a surface of the second substantially transparent polymer layer that is not affixed to the first substantially transparent polymer layer, wherein the one or more columns are not within the center portions of the first or the second substantially transparent polymer layer. In some embodiments, the beads are a substantially circular disc. In some embodiments, the center portion of the first substantially transparent polymer layer comprises between about 5% and about 90% of the surface area of the first substantially transparent polymer layer. In some embodiments, the center portion of the first substantially transparent polymer layer comprises about 25% of the surface area of the first substantially transparent polymer layer. In some embodiments, the beads are less than about 200 µm in diameter. In some embodiments, the beads are about 50 µm in diameter. In some embodiments, the beads are less than about 50 µm in thickness. In some embodiments, the beads are about 10 µm in thickness. In some embodiments, the analyte is selected from the group consisting of a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, a small molecule, a bacterial cell, a cellular organelle, and an antibody fragment. In some embodiments, the substantially transparent polymer of the first or the second substantially transparent polymer layer comprises an epoxy-based polymer. In some embodiments, the epoxy-based polymer is SU-8.

Other aspects of the present disclosure are directed to a method for conducting a multiplex assay comprising the steps of: a) contacting a sample with beads in an assay system, wherein each bead in the system comprises a substantially non-transparent polymer layer having a first surface and a second surface, the first and the second surfaces being parallel to each other, wherein an outline of the substantially non-transparent polymer layer comprises a two-dimensional shape that represents an analog code identifier; wherein the system comprises (i) at least one bead with an analog code identifier that is recognized by an imaging processor as a specific assay or assay kit, specific analyte, manufacturing lot, individual, locational identifier, or calibration signal, and (ii) a plurality of beads, wherein each bead of the plurality of beads comprises a capture agent that specifically binds to an analyte, wherein the capture agent is immobilized on at least one of the first surface and the second surface of the substantially transparent polymer layer in at least the center portion of the substantially transparent polymer layer, and wherein each bead of the plurality of beads comprises an analog code identifier corresponding to the capture agent; and simultaneously or sequentially, in any order: b) identifying the identifier that is recognized by the imaging processor as the specific assay; and c) detecting the binding of the analyte in the sample by analyzing the binding of the analyte to the capture agent immobilized on the surface of the bead based on the identification of the analog code identifier corresponding to the capture agent.

In some embodiments, the system further comprises (iii) at least two beads, at least three beads, at least four beads, at least five beads, or at least six beads, each with an analog code identifier that is recognized by an imaging processor as a specific assay or assay kit, specific analyte, manufacturing lot, individual, locational identifier, or calibration signal. In some embodiments, the system further comprises (iv) at least one bead recognized by the imaging processor as a positive or negative control. In some embodiments, the locational identifier corresponds to a hospital, a diagnostic laboratory, an address, a health care professional's office, or a research laboratory. In some embodiments, the system further comprises (v) at least one bead that is pre-labeled for monitoring functions of the imaging processor. In some embodiments, the beads comprise a spherical or rectangular shape. In some embodiments, the beads are less than about 300 µm in diameter. In some embodiments, the surface of the bead is smooth and lacks surface irregularities. In some embodiments, at least one surface of the bead comprises at least one site for chemical attachment of the capture agent. In some embodiments, the capture agent is selected from the group consisting of: a DNA molecule, a DNA-analog-molecule, an RNA-molecule, an RNA-analog-molecule, a polynucleotide, a protein, an enzyme, a lipid, a phospho-lipid, a carbohydrate moiety, a polysaccharide, an antigen, a virus, a cell, an antibody, and an antibody fragment. In some embodiments, the plurality of beads are magnetic or non-magnetic.

In some embodiments, the beads further comprise: (3) a magnetic, substantially non-transparent layer that encloses the center portion of the substantially transparent polymer layer between the substantially non-transparent polymer layer and the center portion of the substantially transparent polymer layer, wherein the magnetic, substantially non-transparent layer is affixed to the first surface or the second surface of the substantially transparent polymer layer. In some embodiments, the beads further comprise: (4) a second substantially transparent polymer layer aligned with the first substantially transparent polymer layer, the second substantially transparent polymer layer having a center portion that is aligned with the center portion of the first substantially transparent polymer layer, wherein the second substantially transparent polymer layer is affixed to the second surface of the first substantially transparent polymer layer and does not extend beyond the two-dimensional shape of the first substantially transparent polymer layer; and (5) a magnetic, substantially non-transparent layer that encloses the center portion of the first substantially transparent polymer layer between the substantially non-transparent polymer layer and the center portion of the substantially transparent polymer layer, wherein the magnetic, substantially non-transparent layer is affixed between the first and the second substantially transparent polymer layers. In some embodiments, the beads further comprise an orientation indicator for orienting the analog code of the substantially non-transparent polymer layer. In some embodiments, the orientation indicator comprises an asymmetry of the magnetic, substantially non-transparent layer. In some embodiments, the magnetic, substantially non-transparent layer comprises nickel. In some embodiments, the magnetic, substantially non-transparent layer is between about 50 nm and about 10 µm in thickness. In some embodiments, the magnetic, substantially non-transparent layer is about 0.1 µm in thickness. In some embodiments, the two-dimensional shape of the substantially non-transparent polymer layer comprises one or more rings enclosing the center portion of the substantially transparent polymer layer, wherein at least one of the one or more rings comprises a discontinuity. In some embodiments, the two-dimensional shape of the substantially non-transparent polymer layer comprises a gear shape comprising a plurality of gear teeth, and wherein the analog code is represented by one or more aspects selected from the group consisting of the height of one or more gear teeth of the plurality, the width of one or more gear teeth of the plurality, the number of gear teeth in the plurality, and the arrangement of one or more gear teeth within the plurality. In some embodiments, the plurality of gear teeth comprises one or more gear teeth that are between about 1 µm and about 10 µm wide. In some embodiments, the plurality of gear teeth comprises one or more gear teeth that are between about 1 µm and about 10 µm tall. In some embodiments, the plurality of gear teeth comprises two or more gear teeth that are spaced between about 1 µm and about 10 µm apart. In some embodiments, the beads further comprise: (6) one or more columns projecting from the first surface of the first substantially transparent polymer layer, wherein the one or more columns are not within the center portion of the first substantially transparent polymer layer; and/or (7) one or more columns projecting from the second surface of the first substantially transparent polymer layer or a surface of the second substantially transparent polymer layer that is not affixed to the first substantially transparent polymer layer, wherein the one or more columns are not within the center portions of the first or the second substantially transparent polymer layer. In some embodiments, the beads are a substantially circular disc. In some embodiments, the center portion of the first substantially transparent polymer layer comprises between about 5% and about 90% of the surface area of the first substantially transparent polymer layer. In some embodiments, the center portion of the first substantially transparent polymer layer comprises about 25% of the surface area of the first substantially transparent polymer layer. In some embodiments, the beads are less than about 200 µm in diameter. In some embodiments, the beads are about 50 µm in diameter. In some embodiments, the beads are less than about 50 µm in thickness. In some embodiments, the beads are about 10 µm in thickness. In some embodiments, the analyte is selected from the group consisting of a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, a small molecule, a bacterial cell, a cellular organelle, and an antibody fragment. In some embodiments, the substantially transparent polymer of the first or the second substantially transparent polymer layer comprises an epoxy-based polymer. In some embodiments, the epoxy-based polymer is SU-8.

VI. Kits

In further aspects, provided herein are kits or conducting a multiplex assay comprising: a) a set of beads, wherein each bead in the set comprises a substantially non-transparent polymer layer having a first surface and a second surface, the first and the second surfaces being parallel to each other, wherein an outline of the substantially non-transparent polymer layer comprises a two-dimensional shape that represents an analog code identifier; and wherein the set of beads comprises (i) at least one bead with an analog code identifier that is recognized by an imaging processor as a specific assay or assay kit, specific analyte, manufacturing lot, individual, locational identifier, or calibration signal, and (ii) a plurality of additional beads, wherein each bead of the plurality of beads comprises a capture agent that specifically binds to an analyte, wherein the capture agent is immobilized on at least one of the first surface and the second surface of the substantially transparent polymer layer in at least the center portion of the substantially transparent polymer layer, and wherein each bead of the plurality of beads comprises an analog code identifier corresponding to the capture agent; and b) a signal-emitting entity capable of directly or indirectly binding to the analyte or capture agent.

In some embodiments, the signal-emitting entity indirectly binds to the analyte or capture agent via a secondary antibody that is conjugated to the signal-emitting entity. In some embodiments, the signal-emitting entity indirectly binds to the analyte or capture agent via a nucleotide probe that is conjugated to the signal-emitting entity. In some embodiments, the signal-emitting entity is phycoerythrin, GFP, RFP, CFP, YFP, FITC, horseradish peroxidase, alkaline phosphatase, or a radiolabel.

In some embodiments, the kit further comprises at least two beads, at least three beads, at least four beads, at least five beads, or at least six beads, each with an analog code identifier that is recognized by an imaging processor as a specific assay or assay kit, specific analyte, manufacturing lot, individual, locational identifier, or calibration signal. In some embodiments, the kit further comprises an imaging processor for (i) identifying the at least one bead with an identifier that is recognized by the imaging processor as a specific assay, (ii) identifying the identifier on the plurality of beads, (iii) detecting the amount of signal produced by the signal-emitting entity, (iv) identifying the at least one bead with an identifier that is recognized by the imaging processor as a manufacturing lot, (v) identifying the at least one bead with an identifier that is recognized by the imaging processor as an individual, (vi) identifying the at least one bead with an identifier that is recognized by the imaging processor as a locational identifier, or (vii) identifying the at least one bead that is pre-labeled for calibration of the imaging processor. In some embodiments, the kit further comprises an entity capable of directly or indirectly binding to the analyte or capture agent, wherein the entity comprises an affinity tag. In some embodiments, the kit further comprises at least one bead that is pre-labeled for monitoring functions of the imaging processor.

In some embodiments, the affinity tag is biotin, $His_6$, or maltose. In some embodiments, the beads comprise a spherical or rectangular shape. In some embodiments, the beads are less than about 300 µm in diameter. In some embodiments, the surface of the bead is smooth and lacks surface irregularities. In some embodiments, at least one surface of the bead comprises at least one site for chemical attachment of the capture agent. In some embodiments, the capture agent is selected from the group consisting of: a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, a small molecule, and an antibody fragment. In some embodiments, the plurality of beads are magnetic or non-magnetic.

In some embodiments, the bead further comprises: (3) a magnetic, substantially non-transparent layer that encloses the center portion of the substantially transparent polymer layer between the substantially non-transparent polymer layer and the center portion of the substantially transparent polymer layer, wherein the magnetic, substantially non-transparent layer is affixed to the first surface or the second surface of the substantially transparent polymer layer. In some embodiments the bead further comprises: (4) a second substantially transparent polymer layer aligned with the first substantially transparent polymer layer, the second substantially transparent polymer layer having a center portion that is aligned with the center portion of the first substantially transparent polymer layer, wherein the second substantially transparent polymer layer is affixed to the second surface of the first substantially transparent polymer layer and does not extend beyond the two-dimensional shape of the first substantially transparent polymer layer; and (5) a magnetic, substantially non-transparent layer that encloses the center portion of the first substantially transparent polymer layer between the substantially non-transparent polymer layer and the center portion of the substantially transparent polymer layer, wherein the magnetic, substantially non-transparent layer is affixed between the first and the second substantially transparent polymer layers. In some embodiments, the bead further comprises an orientation indicator for orienting the analog code of the substantially non-transparent polymer layer. In some embodiments, the orientation indicator comprises an asymmetry of the magnetic, substantially non-transparent layer. In some embodiments, the magnetic, substantially non-transparent layer comprises nickel. In some embodiments, the magnetic, substantially non-transparent layer is between about 50 nm and about 10 µm in thickness. In some embodiments, the magnetic, substantially non-transparent layer is about 0.1 µm in thickness. In some embodiments, the two-dimensional shape of the substantially non-transparent polymer layer comprises one or more rings enclosing the center portion of the substantially transparent polymer layer, wherein at least one of the one or more rings comprises a discontinuity. In some embodiments, the two-dimensional shape of the substantially non-transparent polymer layer comprises a gear shape comprising a plurality of gear teeth, and wherein the analog code is represented by one or more aspects selected from the group consisting of the height of one or more gear teeth of the plurality, the width of one or more gear teeth of the plurality, the number of gear teeth in the plurality, and the arrangement of one or more gear teeth within the plurality. In some embodiments, the plurality of gear teeth comprises one or more gear teeth that are between about 1 μm and about 10 μm wide. In some embodiments, the plurality of gear teeth comprises one or more gear teeth that are between about 1 μm and about 10 μm tall. In some embodiments, the plurality of gear teeth comprises two or more gear teeth that are spaced between about 1 μm and about 10 μm apart.

In some embodiments, the beads further comprise: (6) one or more columns projecting from the first surface of the first substantially transparent polymer layer, wherein the one or more columns are not within the center portion of the first substantially transparent polymer layer; and/or (7) one or more columns projecting from the second surface of the first substantially transparent polymer layer or a surface of the second substantially transparent polymer layer that is not affixed to the first substantially transparent polymer layer, wherein the one or more columns are not within the center portions of the first or the second substantially transparent polymer layer. In some embodiments, the bead is a substantially circular disc. In some embodiments, the center portion of the first substantially transparent polymer layer comprises between about 5% and about 90% of the surface area of the first substantially transparent polymer layer. In some embodiments, the center portion of the first substantially transparent polymer layer comprises about 25% of the surface area of the first substantially transparent polymer layer. In some embodiments, the beads are less than about 200 μm in diameter. In some embodiments, the beads are about 50 μm in diameter. In some embodiments, the beads are less than about 50 μm in thickness. In some embodiments, the beads are about 10 μm in thickness. In some embodiments, the analyte is selected from the group consisting of a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, a small molecule, a bacterial cell, a cellular organelle, and an antibody fragment. In some embodiments, the substantially transparent polymer of the first or the second substantially transparent polymer layer comprises an epoxy-based polymer. In some embodiments, the epoxy-based polymer is SU-8.

Other aspects of the present disclosure are directed to kits comprising: a) a set of beads, wherein each bead in the set comprises a substantially non-transparent polymer layer having a first surface and a second surface, the first and the second surfaces being parallel to each other, wherein an outline of the substantially non-transparent polymer layer comprises a two-dimensional shape that represents an analog code identifier; and wherein the set of beads comprises (i) at least one bead with an analog code identifier that is recognized by an imaging processor as a specific assay or assay kit, specific analyte, manufacturing lot, individual, locational identifier, or calibration signal, and (ii) a plurality of additional beads, wherein each bead of the plurality of beads comprises a capture agent that specifically binds to an analyte, wherein the capture agent is immobilized on at least one of the first surface and the second surface of the substantially transparent polymer layer in at least the center portion of the substantially transparent polymer layer, and wherein each bead of the plurality of beads comprises an analog code identifier corresponding to the capture agent; and b) a signal-emitting entity capable of directly or indirectly binding to the analyte or capture agent.

In some embodiments, the signal-emitting entity indirectly binds to the analyte or capture agent via a secondary antibody that is conjugated to the signal-emitting entity. In some embodiments, the signal-emitting entity indirectly binds to the analyte or capture agent via a nucleotide probe that is conjugated to the signal-emitting entity. In some embodiments, the signal-emitting entity is phycoerythrin, GFP, RFP, CFP, YFP, FITC, horseradish peroxidase, alkaline phosphatase, or a radiolabel.

In some embodiments, the kit further comprises at least two beads, at least three beads, at least four beads, at least five beads, or at least six beads, each with an analog code identifier that is recognized by an imaging processor as a specific assay or assay kit, specific analyte, manufacturing lot, individual, locational identifier, or calibration signal. In some embodiments, the kit further comprises an imaging processor for (i) identifying the at least one bead with an identifier that is recognized by the imaging processor as a specific assay, (ii) identifying the identifier on the plurality of beads, (iii) detecting the amount of signal produced by the signal-emitting entity, (iv) identifying the at least one bead with an identifier that is recognized by the imaging processor as a manufacturing lot, (v) identifying the at least one bead with an identifier that is recognized by the imaging processor as an individual, (vi) identifying the at least one bead with an identifier that is recognized by the imaging processor as a locational identifier, or (vii) identifying the at least one bead that is pre-labeled for calibration of the imaging processor. In some embodiments, the kit further comprises an entity capable of directly or indirectly binding to the analyte or capture agent, wherein the entity comprises an affinity tag. In some embodiments, the kit further comprises at least one bead that is pre-labeled for monitoring functions of the imaging processor.

In some embodiments, the affinity tag is biotin, $His_6$, or maltose. In some embodiments, the beads comprise a spherical or rectangular shape. In some embodiments, the beads are less than about 300 μm in diameter. In some embodiments, the surface of the bead is smooth and lacks surface irregularities. In some embodiments, at least one surface of the bead comprises at least one site for chemical attachment of the capture agent. In some embodiments, the capture agent is selected from the group consisting of: a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, a small molecule, and an antibody fragment. In some embodiments, the plurality of beads are magnetic or non-magnetic.

In some embodiments, the bead further comprises: (3) a magnetic, substantially non-transparent layer that encloses the center portion of the substantially transparent polymer layer between the substantially non-transparent polymer layer and the center portion of the substantially transparent polymer layer, wherein the magnetic, substantially non-transparent layer is affixed to the first surface or the second surface of the substantially transparent polymer layer. In some embodiments the bead further comprises: (4) a second substantially transparent polymer layer aligned with the first substantially transparent polymer layer, the second substantially transparent polymer layer having a center portion that is aligned with the center portion of the first substantially transparent polymer layer, wherein the second substantially transparent polymer layer is affixed to the second surface of the first substantially transparent polymer layer and does not extend beyond the two-dimensional shape of the first substantially transparent polymer layer; and (5) a magnetic, substantially non-transparent layer that encloses the center portion of the first substantially transparent polymer layer between the substantially non-transparent polymer layer and the center portion of the substantially transparent polymer layer, wherein the magnetic, substantially non-transparent layer is affixed between the first and the second substantially transparent polymer layers. In some embodiments, the bead further comprises an orientation indicator for orienting the analog code of the substantially non-transparent polymer layer. In some embodiments, the orientation indicator comprises an asymmetry of the magnetic, substantially non-transparent layer. In some embodiments, the magnetic, substantially non-transparent layer comprises nickel. In some embodiments, the magnetic, substantially non-transparent layer is between about 50 nm and about 10 µm in thickness. In some embodiments, the magnetic, substantially non-transparent layer is about 0.1 µm in thickness. In some embodiments, the two-dimensional shape of the substantially non-transparent polymer layer comprises one or more rings enclosing the center portion of the substantially transparent polymer layer, wherein at least one of the one or more rings comprises a discontinuity. In some embodiments, the two-dimensional shape of the substantially non-transparent polymer layer comprises a gear shape comprising a plurality of gear teeth, and wherein the analog code is represented by one or more aspects selected from the group consisting of the height of one or more gear teeth of the plurality, the width of one or more gear teeth of the plurality, the number of gear teeth in the plurality, and the arrangement of one or more gear teeth within the plurality. In some embodiments, the plurality of gear teeth comprises one or more gear teeth that are between about 1 µm and about 10 µm wide. In some embodiments, the plurality of gear teeth comprises one or more gear teeth that are between about 1 µm and about 10 µm tall. In some embodiments, the plurality of gear teeth comprises two or more gear teeth that are spaced between about 1 µm and about 10 µm apart.

In some embodiments, the beads further comprise: (6) one or more columns projecting from the first surface of the first substantially transparent polymer layer, wherein the one or more columns are not within the center portion of the first substantially transparent polymer layer; and/or (7) one or more columns projecting from the second surface of the first substantially transparent polymer layer or a surface of the second substantially transparent polymer layer that is not affixed to the first substantially transparent polymer layer, wherein the one or more columns are not within the center portions of the first or the second substantially transparent polymer layer. In some embodiments, the bead is a substantially circular disc. In some embodiments, the center portion of the first substantially transparent polymer layer comprises between about 5% and about 90% of the surface area of the first substantially transparent polymer layer. In some embodiments, the center portion of the first substantially transparent polymer layer comprises about 25% of the surface area of the first substantially transparent polymer layer. In some embodiments, the beads are less than about 200 µm in diameter. In some embodiments, the beads are about 50 µm in diameter. In some embodiments, the beads are less than about 50 µm in thickness. In some embodiments, the beads are about 10 µm in thickness. In some embodiments, the analyte is selected from the group consisting of a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, a small molecule, a bacterial cell, a cellular organelle, and an antibody fragment. In some embodiments, the substantially transparent polymer of the first or the second substantially transparent polymer layer comprises an epoxy-based polymer. In some embodiments, the epoxy-based polymer is SU-8.

VII. Systems

In other aspects, provided herein are multiplex assay systems. In some embodiments, the systems comprise a plurality of beads as described herein, such as any of the beads disclosed in any of the compositions, methods, or kits provided herein. The system also comprises an apparatus comprising an imaging processor system and a reaction detection system, wherein the identification of an analog code identifier that corresponds to one or more of a specific assay or assay kit, a specific capture agent, a manufacturing lot, an individual, a locational identifier, and/or a calibration signal by the imaging processor in the decoding system activates the use of a software analyzing detection signals detected by the reaction detection system correlated to the specific assay or assay kit.

EXAMPLES

The present disclosure will be more fully understood by reference to the following examples. They should not, however, be construed as limiting the scope of the present disclosure. It is understood that the examples and embodiments described herein are for illustrative purposes only and that various modifications or changes in light thereof will be suggested to persons skilled in the art and are to be included within the spirit and purview of this application and scope of the appended claims.

Example 1: Encoded Beads with a Two-Dimensional, Analog Code and Uniform Shape

As described above, analog-encoded beads are highly advantageous for multiplexed assays due to the vast number of potential unique identifiers and reduced recognition error. This Example describes various types of beads encoded with a two-dimensional shape, which may be used as an analog code for identification. It is to be understood that the encoded beads of the present disclosure may include some or all of the optional features set forth below in any combination.

FIGS. 1A & 1B show two views of exemplary bead 100. Bead 100 is a circular disc of approximately 50 µm in diameter and 10 µm in thickness. FIG. 1A provides a view of bead 100 looking at a circular face of the disc, while FIG. 1B shows a side view of bead 100 orthogonal to the surface shown in FIG. 1A. Two components of bead 100 are shown. First, substantially transparent polymer layer 102 provides the body of the bead. Layer 102 may be produced, e.g., using a polymer such as SU-8, as described above.

Substantially non-transparent polymer layer 104 is affixed to a surface of layer 102. While the cross-section of bead 100 shown in FIG. 1B shows a discontinuous view of layer 104, the view shown in FIG. 1A illustrates that layer 104 is shaped like a circular gear with a plurality of teeth. The shape, number, size, and spacing of these gear teeth constitutes a two-dimensional shape, and one or more of these aspects of the gear teeth may be modified in order to produce multiple two-dimensional shapes for analog encoding. Advantageously, the outside edge of layer 104's gear teeth fit within the perimeter of layer 102. This allows for a variety of analog codes, each representing a unique identifier for one species of bead, while maintaining a uniform overall shape across multiple species of bead. Stated another way, each bead species within a population of multiple species may have a different two-dimensional gear shape (i.e., analog code), but each bead will have the same perimeter, leading to greater uniformity of physical properties (e.g., size, shape, behavior in solution, and the like). Layer 104 may be produced, e.g., using a polymer such as SU-8 mixed with a dye, or using a black matrix resist, as described above.

Layer 104 surrounds center portion 106 of layer 102. A capture agent for capturing an analyte is coupled to at least center portion 106 on one or both surfaces (i.e., upper/lower surfaces) of layer 102. Advantageously, this allows center portion 106 to be imaged without any potential for interference resulting from layer 104.

Figure 1C:
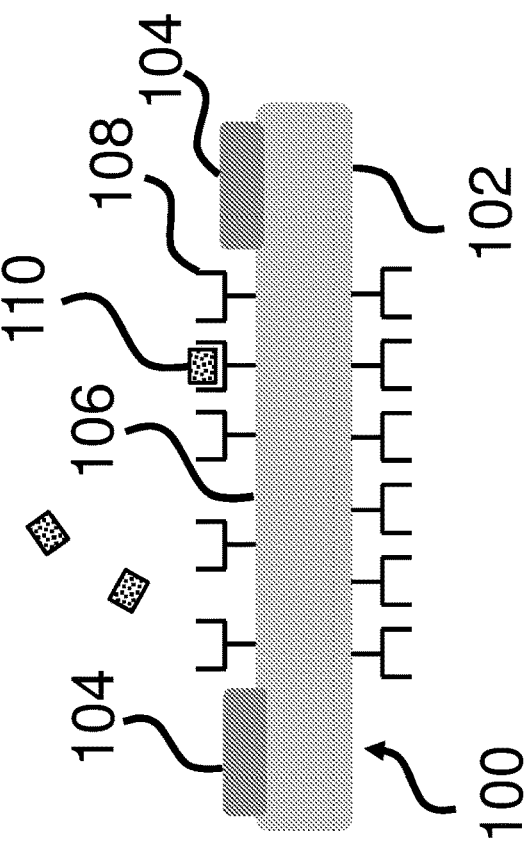

FIGS. 1C & 1D show an exemplary assay using bead 100 for analyte detection. FIG. 1C shows that bead 100 may include capture agent 108 coupled to one or more surfaces in at least center portion 106. Bead 100 is contacted with a solution containing analyte 110, which is captured by capture agent 108. As described above, various capture agents may be used to capture different types of analytes, ranging from small molecules, nucleic acids, and proteins (e.g., antibodies) to organelles, viruses, and cells. FIG. 1C illustrates a single bead species (i.e., bead 100), which captures analyte 110, but in a multiplex assay multiple bead species are used, each species having a particular capture agent that recognizes a specific analyte.

FIG. 1D illustrates an exemplary process for "reading" bead 100. This process includes two steps that may be accomplished simultaneously or separately. First, the capture of analyte 110 by capture agent 108 is detected. In the example shown in FIG. 1D, detection agent 114 binds to analyte 110. Analyte not captured by a capture agent coupled to bead 100 may have been washed off prior to detection, such that only analytes bound to bead 100 are detected. Detection agent 114 also includes a reagent for detection. As one example, detection agent 114 may include a fluorophore that, when excited by light 116 at a wavelength within the excitation spectrum of the fluorophore, emits light 118 (e.g., a photon). Light 118 may be detected by any suitable detection means, such as a fluorescence microscope, plate reader, and the like.

In addition, bead 100 is read for its unique identifier. In the example shown in FIG. 1D, light 112 is used to illuminate the field containing bead 100 (in some embodiments, light 112 may have a different wavelength than lights 116 and 118). When light 112 illuminates the field containing bead 100, it passes through substantially transparent polymer layer 102 but is blocked by substantially non-transparent polymer layer 104, as shown in FIG. 1D. This generates a light pattern that can be imaged, for example, by light microscopy (e.g., using differential interference contrast, or DIC, microscopy). This light pattern is based on the two-dimensional shape (i.e., analog code) of bead 100. Standard image recognition techniques may be used to decode the analog code represented by the image of bead 100.

The analyte detection and identifier imaging steps may occur in any order, or simultaneously. Advantageously, both detection steps shown in FIG. 1D may be accomplished on one imaging device. As one example, a microscope capable of both fluorescence and light (e.g., bright field) microscopy may be used to quantify the amount of analyte 110 bound to bead 100 (e.g., as detected by detection agent 114) and image the analog code created by layers 102 and 104. This allows for a more efficient assay process with fewer equipment requirements.

Turning now to FIGS. 2A & 2B, another exemplary bead 200 is shown. Like bead 100, bead 200 includes substantially transparent polymer layer 202 and substantially non-transparent polymer layer 204. In addition, bead 200 includes magnetic layer 206. As shown in FIG. 2A, magnetic layer 206 may be shaped as a ring between center portion 208 and substantially non-transparent layer 204.

FIG. 2B shows that magnetic layer 206 may be embedded within layer 202. Layer 202 may also include more than one layer, such that magnetic layer 206 is sandwiched between two substantially transparent polymer layers (e.g., as in FIG. 2B). Alternatively, magnetic layer 206 may be affixed to the same surface of layer 202 as layer 204, or magnetic layer 206 may be affixed to the surface of layer 202 opposite layer 204. In some embodiments, magnetic layer 206 may include nickel.

Magnetic layer 206 bestows magnetic properties onto bead 200, which advantageously may be used for many applications. For example, bead 200 may be affixed to a surface by magnetic attraction during a washing step, allowing for effective washing without losing or otherwise disrupting the beads.

In addition to its magnetic properties, layer 206 is also substantially non-transparent. When imaged as shown in FIG. 1D (e.g., using light 112), layer 206 will block, either in part or in whole, transmitted light, thereby creating a pattern for imaging. As shown in FIG. 2A, layer 206 is also asymmetric—in this example, it includes gap 210. This asymmetry creates an orientation indicator that can be imaged, for example, as shown in FIG. 1D using light 112. Advantageously, an orientation indicator may be utilized during image recognition to orient the two-dimensional shape created by imaging layer 204 in a uniform orientation for easier analog code recognition. This allows beads imaged in any orientation to be decoded.

FIG. 3 shows the vast number of potential analog codes possible using the gear shape shown in FIGS. 1A-2B. FIG. 3 illustrates an exemplary coding scheme in which multiple shape variation points are labeled, e.g., at positions 302, 304, 306, 308, 310, 312, 314, 316, 318, 320, 322, 324, 326, and 328 on exemplary bead 300. Even if a simple "filled or not filled" scheme is used, up to $2^{14}$ unique codes are possible based on the use of 14 shape variation points. This scheme is convenient for both manufacturing and for generating two-dimensional shapes that are easily distinguishable for image recognition analysis. However, since analog encoding is used, more complex schemes using more than 2 possibilities (e.g., at each shape variation point as labeled in FIG. 3) are possible, thereby exponentially expanding the number of unique identifiers. For example, multiple gear tooth shapes and/or multiple sizes of gear teeth are possible. A two-dimensional gear shape as shown in FIGS. 1A-3 facilitates a wide range of unique analog codes while providing a large center portion (e.g., center portions 106 and 208) for analyte detection.

FIG. 4A illustrates three exemplary embodiments of the coding scheme shown in FIG. 3: beads 400, 402, and 404. The unique codes of beads 400, 402, and 404 are generated using the simple "filled or not filled" scheme of FIG. 3. FIG. 4B illustrates 10 exemplary embodiments of the cod, inter alia, in terms of number of shapes (e.g., two distinct shapes in code ZN_3, as compared to seven distinct shapes in code ZN_10) and/or size of shapes (e.g., large, small, and intermediate-sized shapes in code ZN_2). Importantly, as described above, more complex encoding schemes are available using analog image recognition, thereby greatly expanding the number of potential unique codes.

Turning now to FIGS. 5A & 5B, another exemplary bead 500 is shown. Like bead 200, bead 500 includes substantially transparent polymer layer 502, substantially non-transparent polymer layer 504, magnetic layer 506, and center portion 508. In addition, bead 500 has four columns including column 510, which may be of any shape that extends from the surface of layer 502. As shown in FIG. 5A, these columns may be arrayed in alignment with magnetic layer 506, preventing any potential for interfering with analyte detection in center portion 508 or with reading the two-dimensional shape (i.e., the analog code) of layer 504. FIG. 5B shows that these columns may extend from the upper and lower surfaces of bead 500. Column 510 may be made, for example, using the same substantially transparent polymer as layer 502 (exemplary methods of production are described infra). Advantageously, one or more columns such as column 510 may be used to prevent beads from sticking to each other and/or a container (e.g., the side of a well in a multiwell plate), e.g., through optical contact bonding.

Example 2: Beads with a Two-Dimensional, Analog Code Encoded in the Bead Shape

The previous Example illustrates multiple exemplary embodiments of beads in which an analog code is provided by a non-transparent layer affixed to a transparent polymer layer. This is advantageous, for example, in allowing greater uniformity between different species of beads (i.e., each has the same perimeter shape provided by the transparent polymer layer).

However, it may be advantageous for other reasons to use the perimeter of the bead itself as the two-dimensional shape for analog encoding. For example, if the analog code is provided by the shape of the bead itself, only one layer is required, thereby streamlining the manufacturing process. Moreover, shaping the perimeter of the bead may be accomplished by highly precise manufacturing techniques, allowing a highly reproducible shape for more accurate image recognition.

Figure 6B:
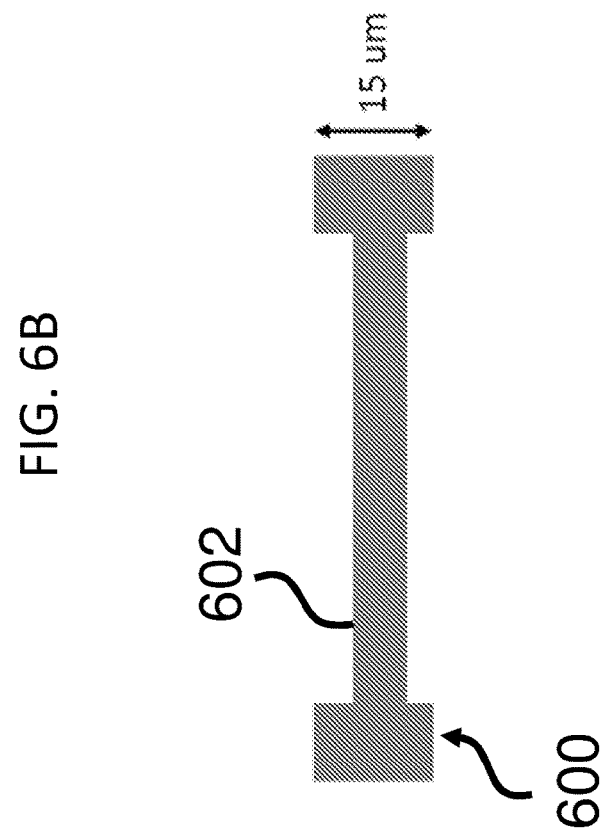
FIGS. 6A & 6B show two views of an exemplary bead.
Figure 6A:
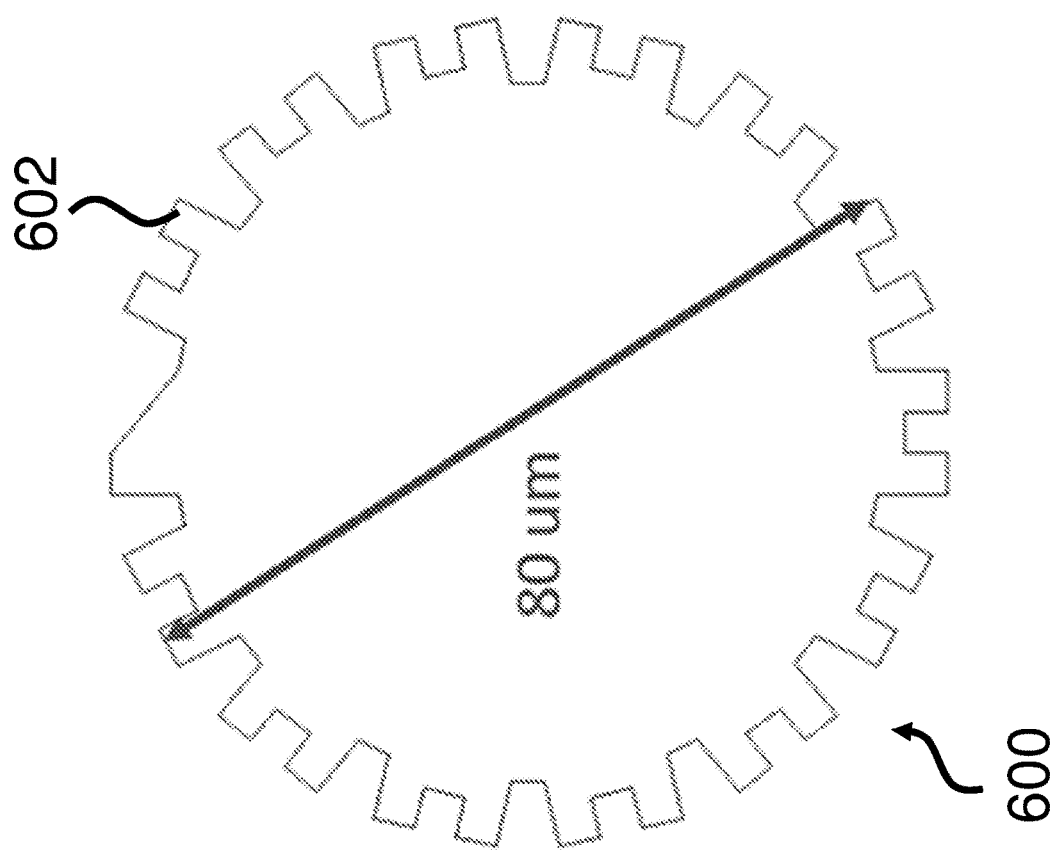

FIGS. 6A & 6B show exemplary bead 600 of this type. Bead 600 is a gear-shaped disc approximately 80 μm in diameter and 15 μm in height, including optional column elements (similar to column 510 as described above). Bead 600 is made of a single, non-transparent polymer layer 602, rather than separate transparent and non-transparent polymer layers. Bead 600 may be imaged as shown in FIG. 1D, but its analog code is imaged based on the entire bead shape (e.g., perimeter of the non-transparent polymer layer). One or both surfaces of bead 600 may be used for coupling a capture agent as above, and a center portion or the entire surface may be used.

Figure 6C:
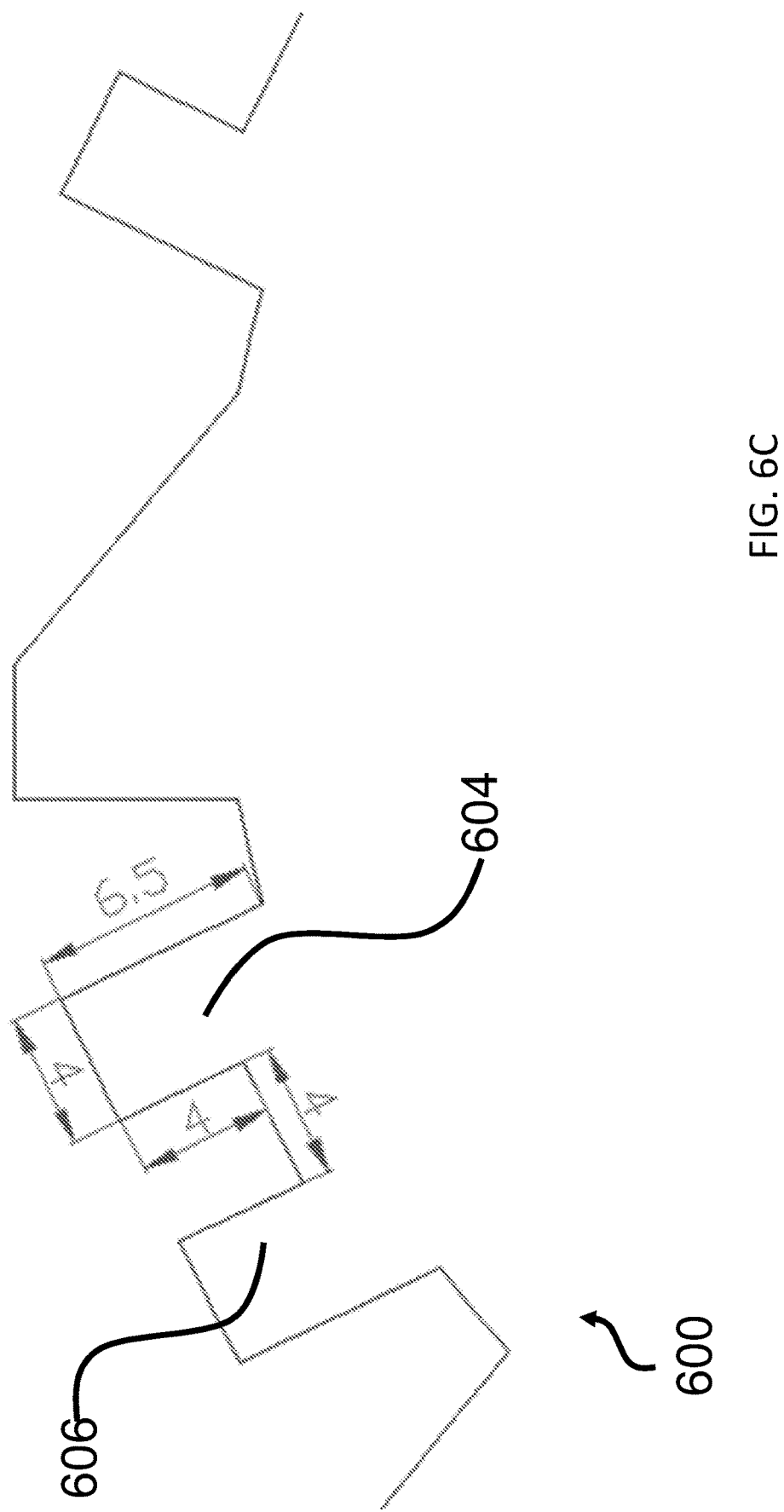
FIG. 6C shows the dimensions of an exemplary analog code. Dimensions are based on μm units.

FIG. 6C illustrates the dimensions of gear tooth 604 of bead 600. As shown, in this embodiment, gear tooth 604 is 4 μm wide and spaced 4 μm from adjacent gear tooth 606. Since the two-dimensional shape of bead 600 is analog encoded, the perimeter between adjacent gear teeth may be variable, allowing for multiple gear tooth shapes. For example, gear tooth 604 extends 4 or 6.5 μm in height, relative to the adjacent perimeter segment immediately to the left or right, respectively.

Figure 7:
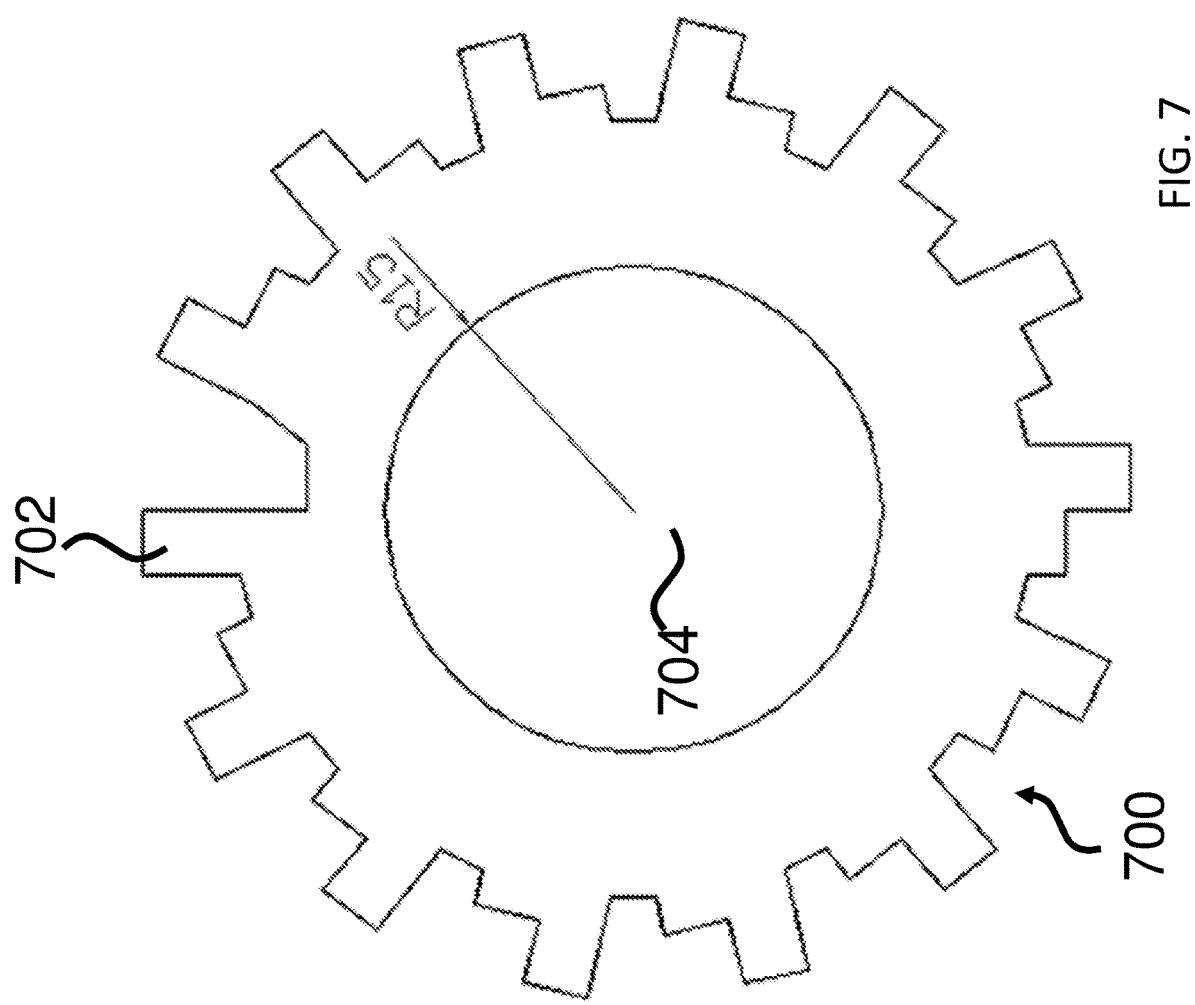
FIG. 7 shows an exemplary bead.

FIG. 7 illustrates another embodiment of this type of bead, bead 700. Like bead 600, bead 700 is made from non-transparent polymer layer 702. In addition, bead includes magnetic layer 704. Magnetic layer 704 may be affixed to one of the surfaces of bead 700, or it may be embedded within bead 700 (e.g., between two non-transparent polymer layers). Magnetic layer 704 may be generated, for example, by depositing nickel. As described above, a magnetic layer allows additional functionalities, such as the option for washing bead 700 while magnetically attached to another surface.

Figure 8A:
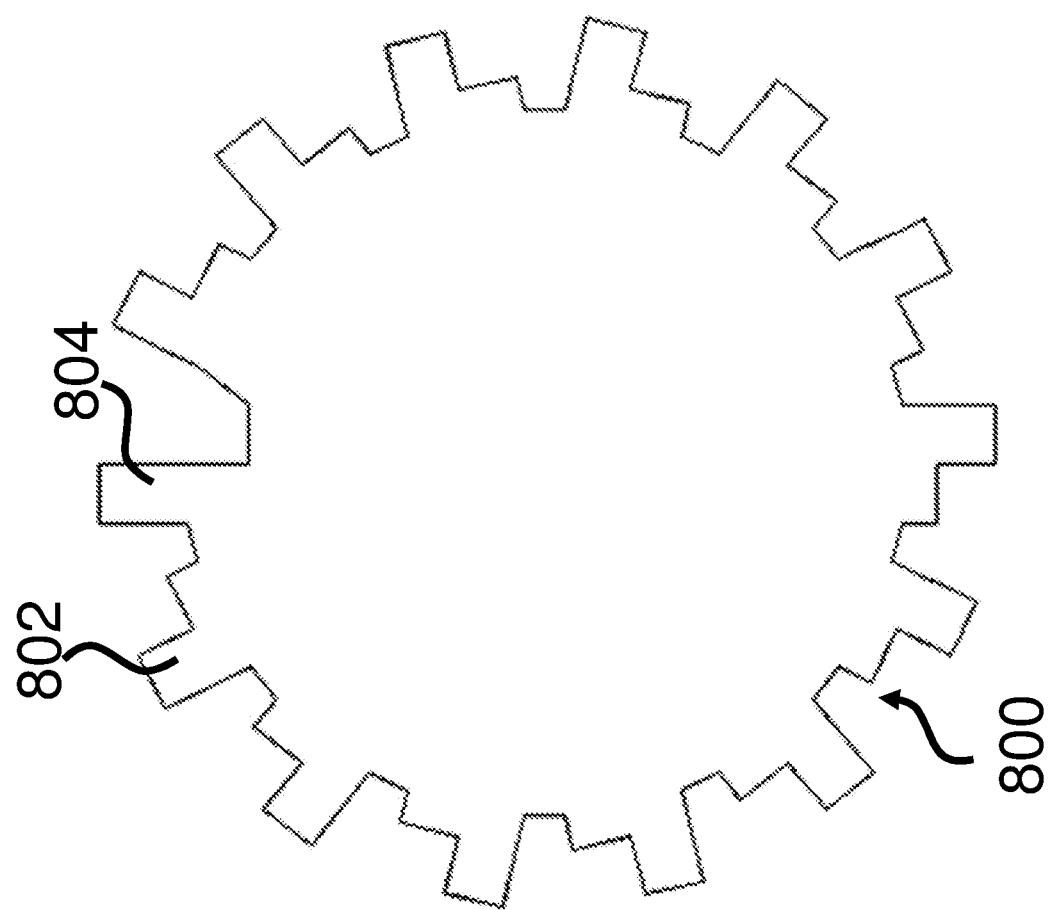
FIG. 8A shows an exemplary bead that includes an asymmetric start position as an orientation indicator.

Turning now to FIG. 8A, another exemplary bead 800 is shown. Like bead 700, bead 800 includes non-transparent polymer layer 802 (and optionally, a magnetic layer such as layer 704). In addition, bead 800 includes start position 804, which has a different shape than the rest of the perimeter of bead 800. Start position 804 may be used as an orientation indicator for image recognition, as described above in reference to gap 210 shown in FIG. 2A.

Figure 8B:
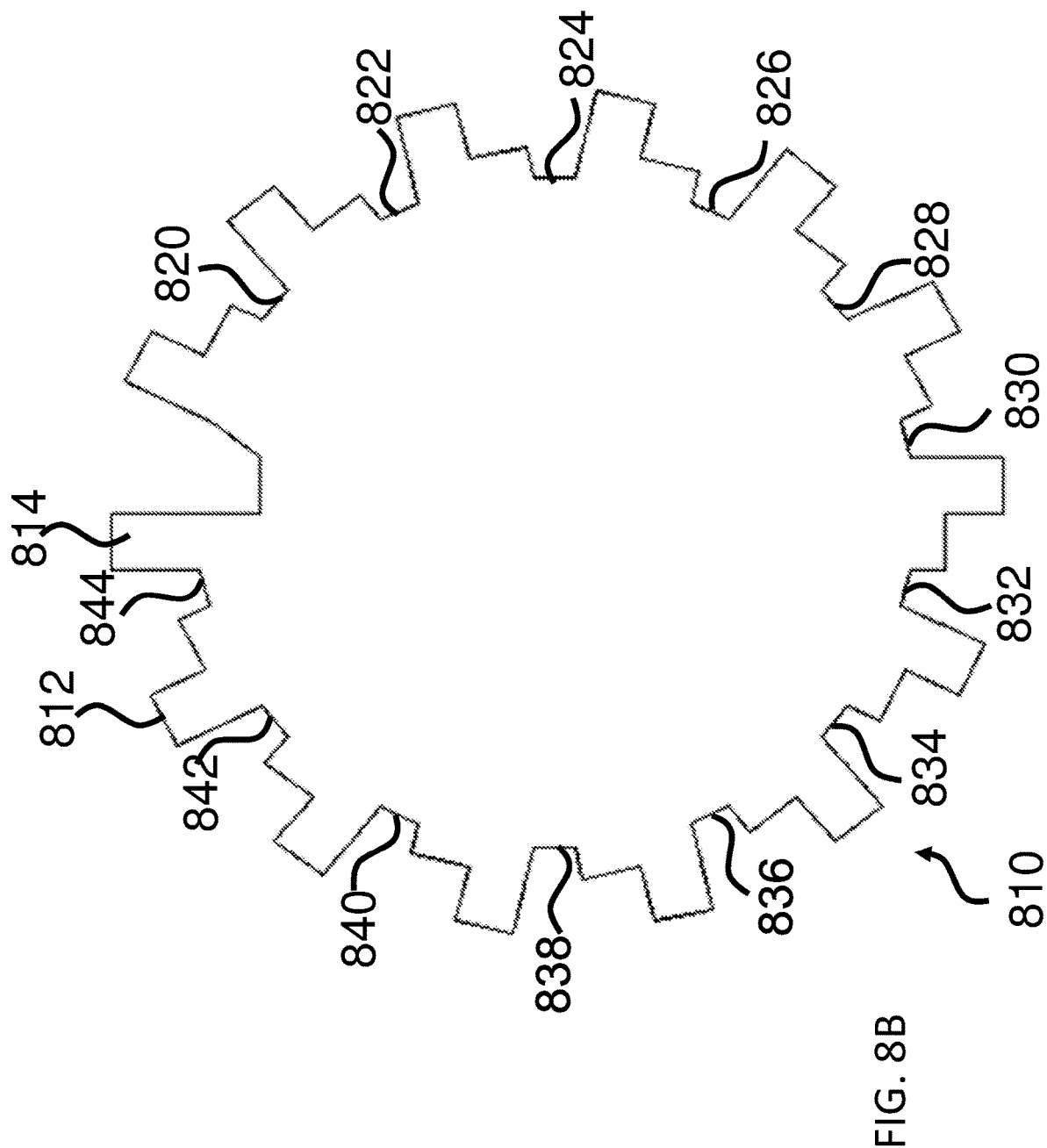
FIG. 8B shows an exemplary analog encoding scheme that includes multiple shape variation points for generating unique analog codes.

FIG. 8B illustrates a coding scheme that may be used. FIG. 8B shows bead 810, which like bead 800 includes non-transparent polymer layer 812 and start position 814 (and optionally, a magnetic layer such as layer 704). In this scheme, potential shape variation points around the gear are labeled, e.g., at positions 820, 822, 824, 826, 828, 830, 832, 834, 836, 838, 840, 842, and 844. As shown in FIG. 8B, even if only two potential shapes may be used for positions 820, 822, 824, 826, 828, 830, 832, 834, 836, 838, 840, 842, and 844, this embodiment allows up to $2^{13}$ unique codes. Further, as described above, the use of analog encoding greatly expands this number by allowing the use of more than two potential shapes at any or all of the indicated positions around the perimeter (e.g., at each shape variation point as labeled in FIG. 8B).

FIGS. 9A-9C illustrate yet another potential embodiment in bead 900. Like bead 800, bead 900 is a gear-shaped bead that includes non-transparent polymer layer 902 and start position 904 (and optionally, a magnetic layer such as layer 704). In addition, bead 900 may have one or more columns (e.g., column 906) affixed to one or both surfaces of bead 900. As shown in the cross-section in FIG. 9B, column 906 extends from a surface of layer 902. Advantageously, column 906 helps to reduce the potential for optical contact bonding (as described above in reference to column 510).

FIG. 9C illustrates the dimensions of column 906. In this example, column 906 is a cylinder 3 μm in height and 3 μm in diameter, although as described above such columns are in no way limited to a cylindrical shape. In some embodiments, column 906 is made of a magnetic material, such as nickel. This allows column 906 to function additionally as a magnetic element for magnetic manipulation of bead 900, as described above.

Example 3: Methods of Producing Beads with a Two-Dimensional, Analog Code Encoded in the Bead Shape Having described exemplary embodiments of multiple types of beads in the previous Examples, attention is now directed to methods of producing beads. As described above, the beads of the present disclosure may be made of one, two, or more constituent layers, depending on the desired configuration and/or optional features.

Figure 10:
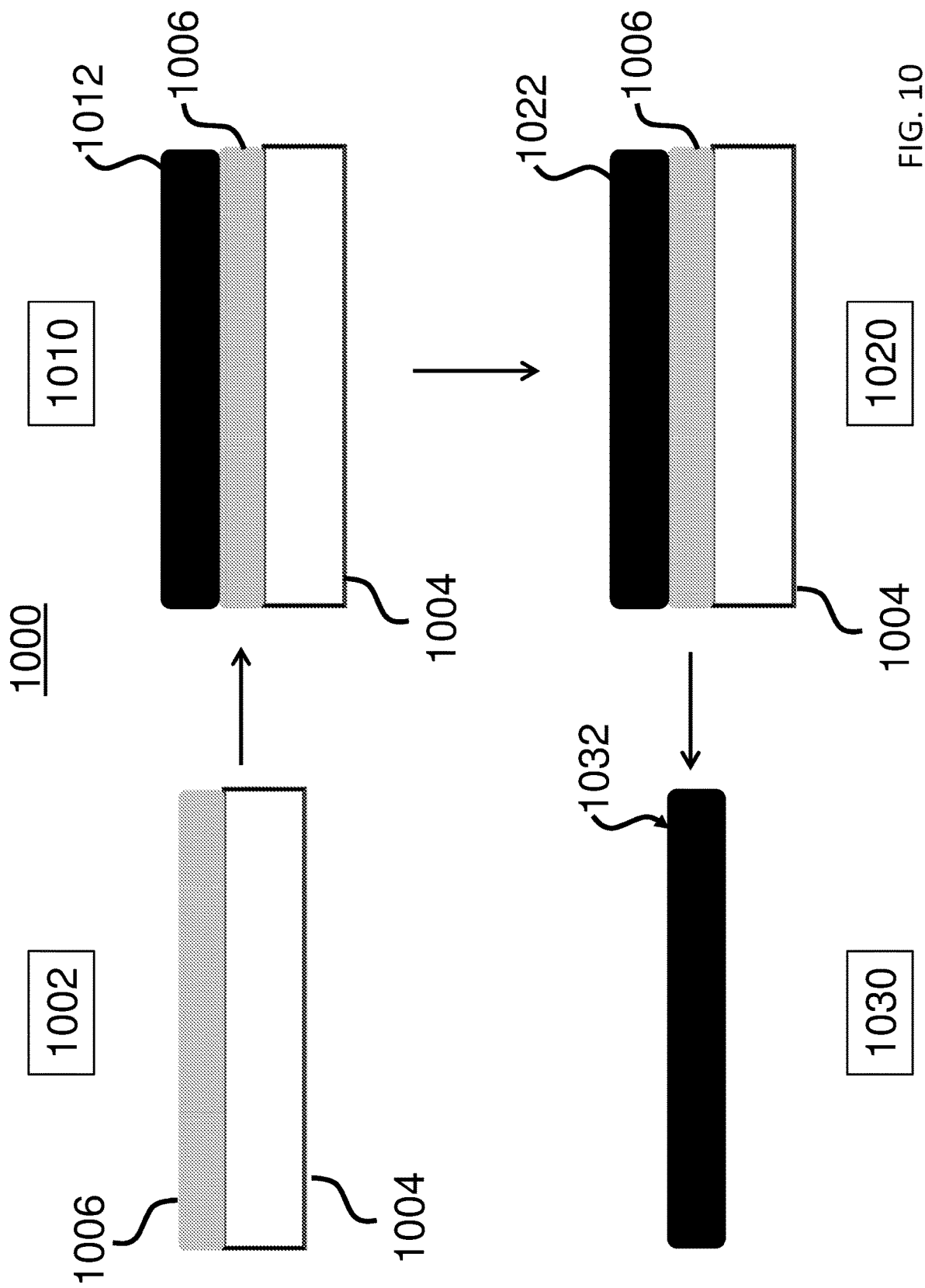
FIG. 10 shows a method for producing an exemplary bead.

Process 1000 shown in FIG. 10 illustrates an exemplary workflow for manufacturing a single layer bead, such as those described in Example 2 above. At block 1002, sacrificial layer 1006 is constructed on substrate 1004. In some embodiments, substrate 1004 may be a glass substrate. At block 1010, layer 1012 is deposited on sacrificial layer 1006. In some embodiments, layer 1012 is a non-transparent polymer layer. At block 1020, the perimeter of layer 1012 is shaped into a gear shape (as described above) using lithography to generate gear-shaped layer 1022. At block 1030, the entire structure (i.e., layer 1022, sacrificial layer 1006, and substrate 1004) is immersed in a solvent. This solvent treatment dissolves sacrificial layer 1006 and releases gear-shaped layer 1022 from substrate 1004, thereby generating bead 1032. In some embodiments, bead 1032 may be further modified, for example, by coupling a capture agent to one or both surfaces.

As described in Example 2 above, gear-shaped beads may include optional elements such as magnetic components (e.g., columns and/or magnetic layers). Process 1100 shown in FIGS. 11A & 11B illustrates an exemplary workflow for manufacturing gear-shaped beads with one or more magnetic components.

Figure 11A:
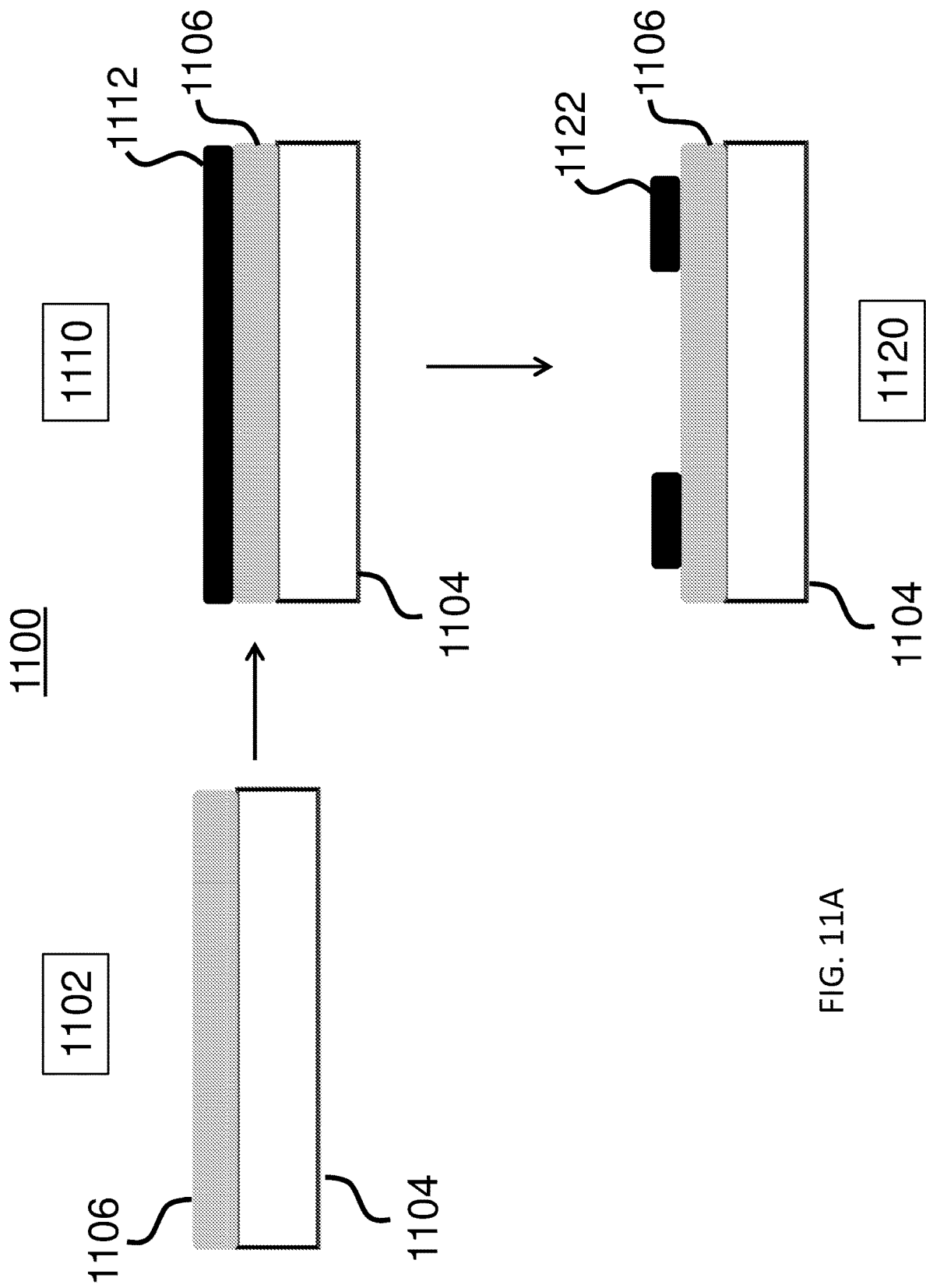
FIGS. 11A & 11B show a method for producing an exemplary bead.

As shown in FIG. 11A, at block 1102, sacrificial layer 1106 is constructed on substrate 1104. In some embodiments, substrate 1104 may be a glass substrate. At block 1110, magnetic layer 1112 is deposited on sacrificial layer 1106. In some embodiments, magnetic layer 1112 includes nickel. At block 1120, magnetic layer 1112 is shaped by lithography into shaped magnetic layer 1122. Shaped magnetic layer 1122 may take any desired shape, e.g., it may be shaped into one or more columns, as illustrated in FIG. 9A with column 906.

Figure 11B:
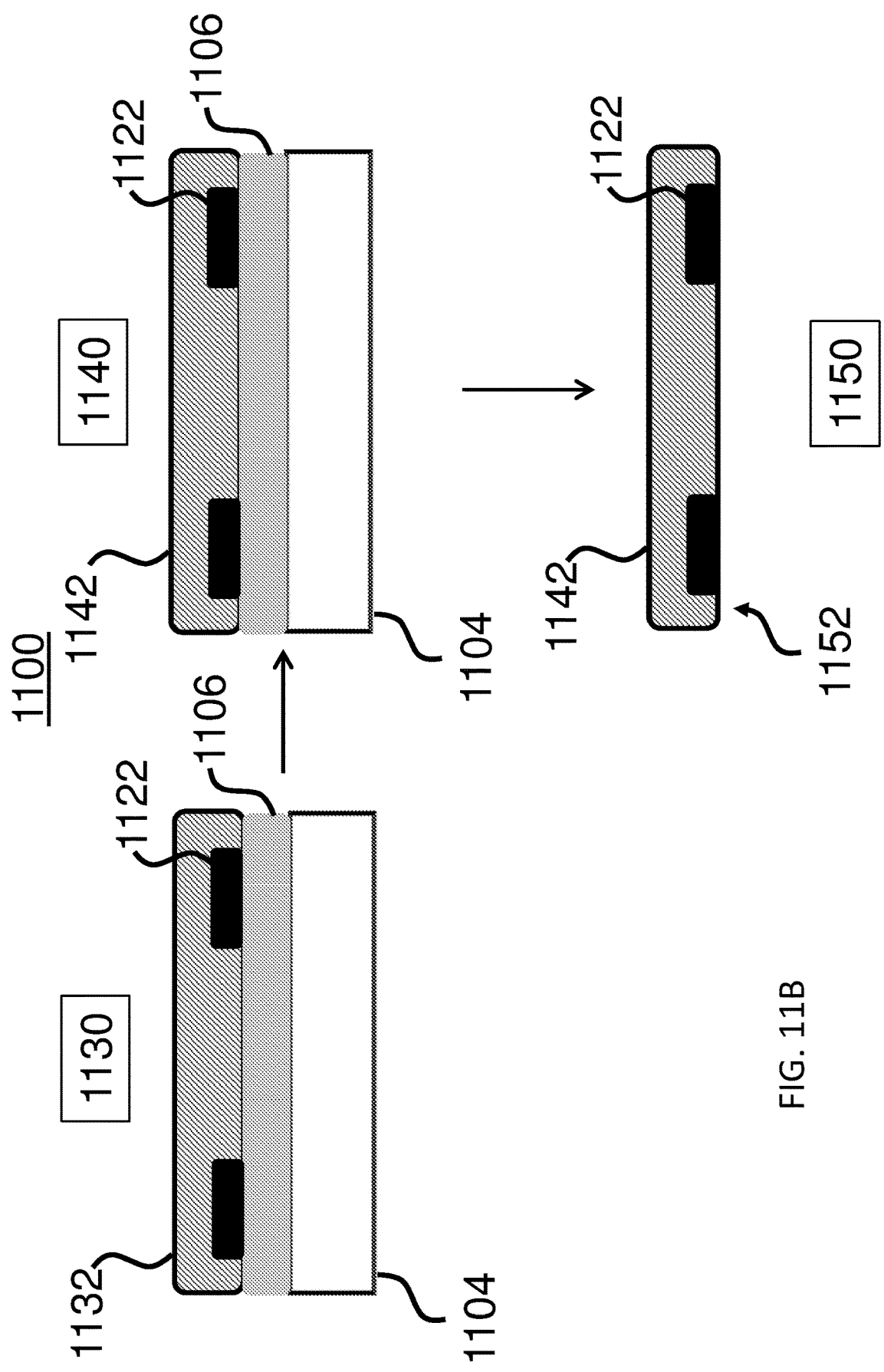

As shown in FIG. 11B, at block 1130, substantially non-transparent polymer layer 1132 is deposited over shaped magnetic layer 1122 and sacrificial layer 1106. At block 1140, the perimeter of layer 1132 is shaped by lithography into gear-shaped substantially non-transparent layer 1142 (such as one of the gear shapes illustrated in FIGS. 6A-9A). At block 1150, the entire structure (i.e., layer 1142, shaped magnetic layer 1122, sacrificial layer 1106, and substrate 1104) is immersed in a solvent. This solvent treatment dissolves sacrificial layer 1106 and releases gear-shaped layer 1142 and shaped magnetic layer 1122 from substrate 1104, thereby generating bead 1152. In some embodiments, bead 1152 may be further modified, for example, by coupling a capture agent to one or both surfaces.

Example 4: Methods of Producing Encoded Beads with a Two-Dimensional, Analog Code and Uniform Shape Attention is now directed to methods of producing encoded beads with a one or more substantially transparent and one or more substantially non-transparent polymer layers, such as those described in Example 1. FIGS. 12A-12E illustrate process 1200, an exemplary workflow for manufacturing beads with a substantially transparent polymer layer, a substantially non-transparent polymer layer (whose two-dimensional shape constitutes an analog code), and one or more columns.

Figure 12A:
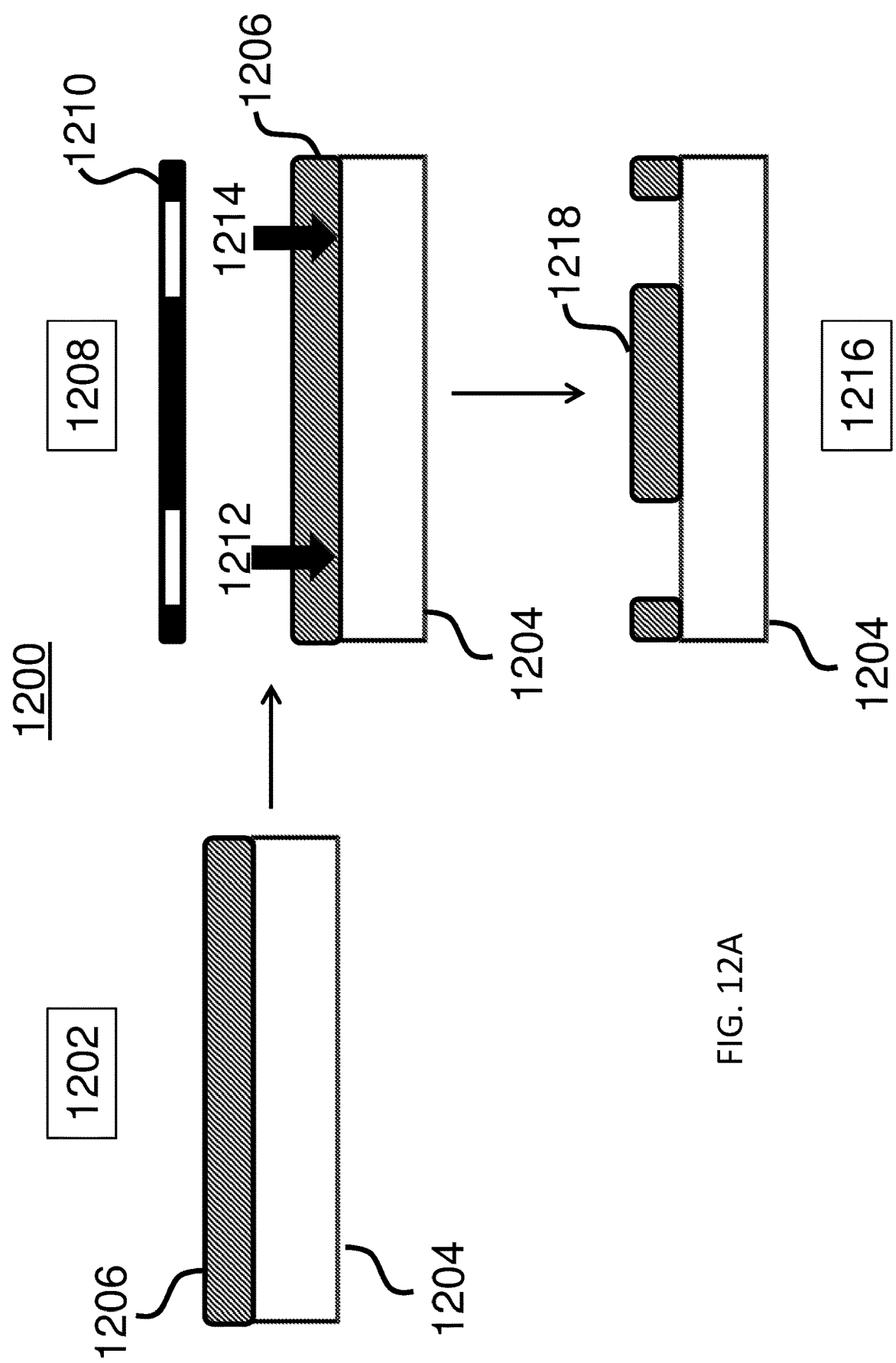
FIGS. 12A-12E show a method for producing an exemplary bead.
Figure 12B:
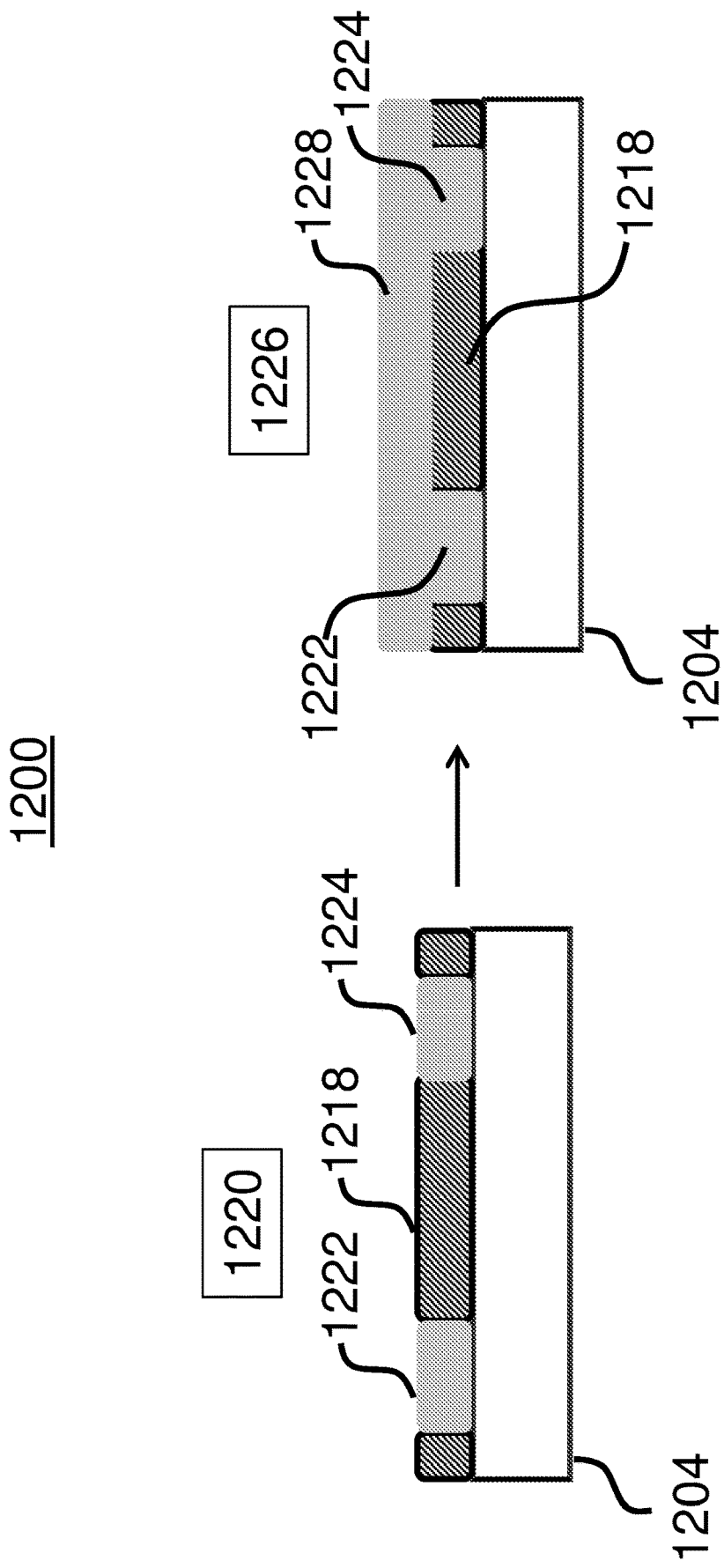
Figure 12C:
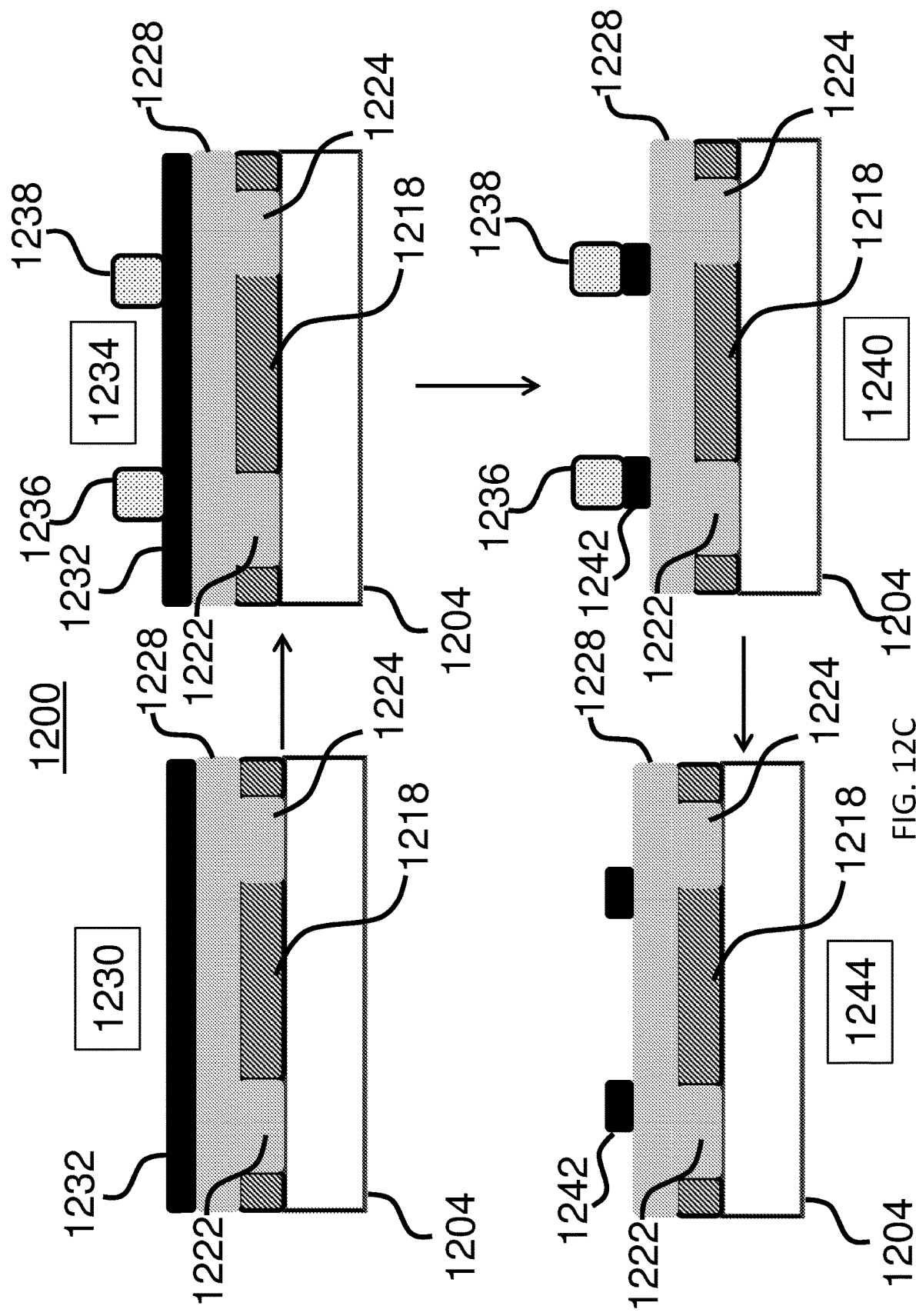
Figure 12D:
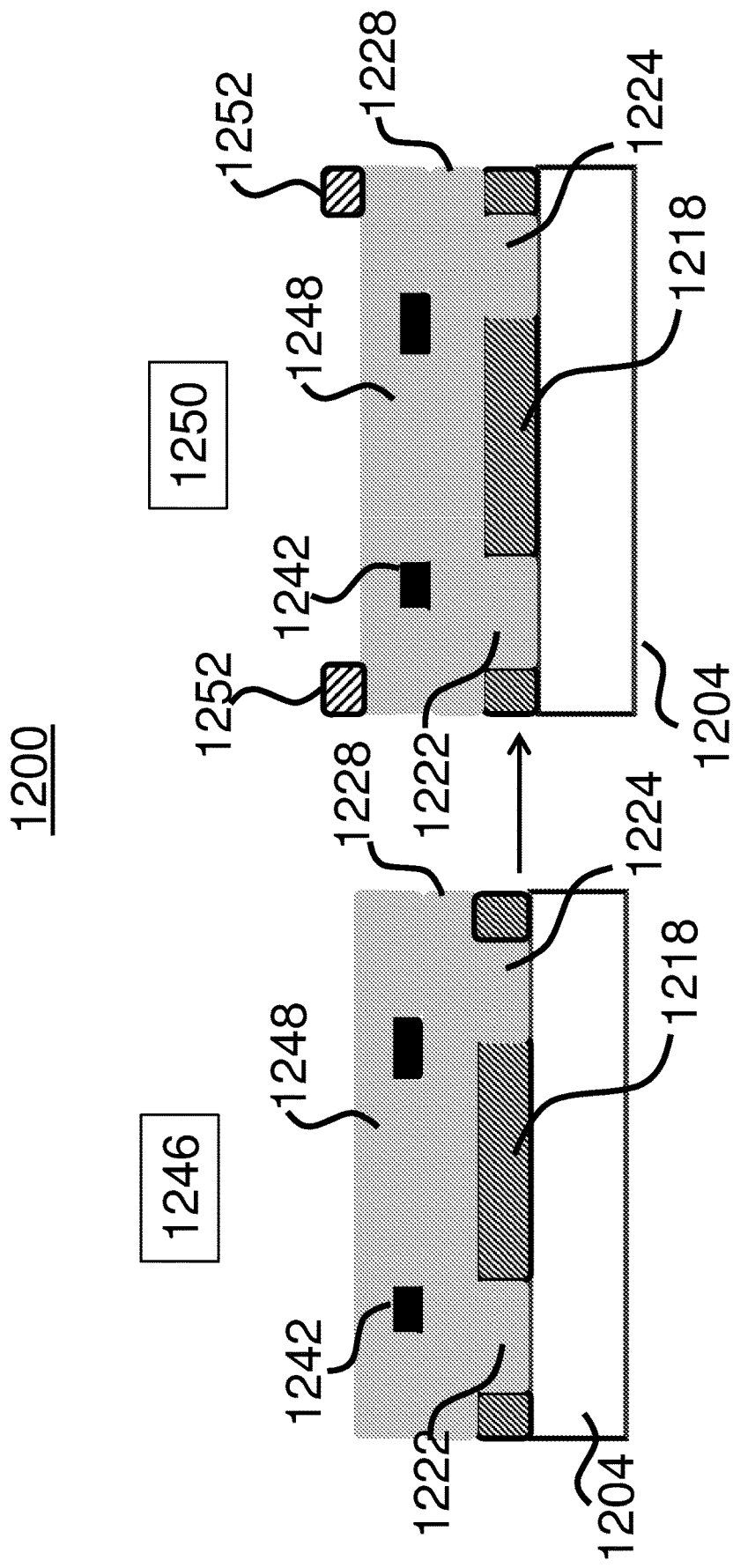
Figure 12E:
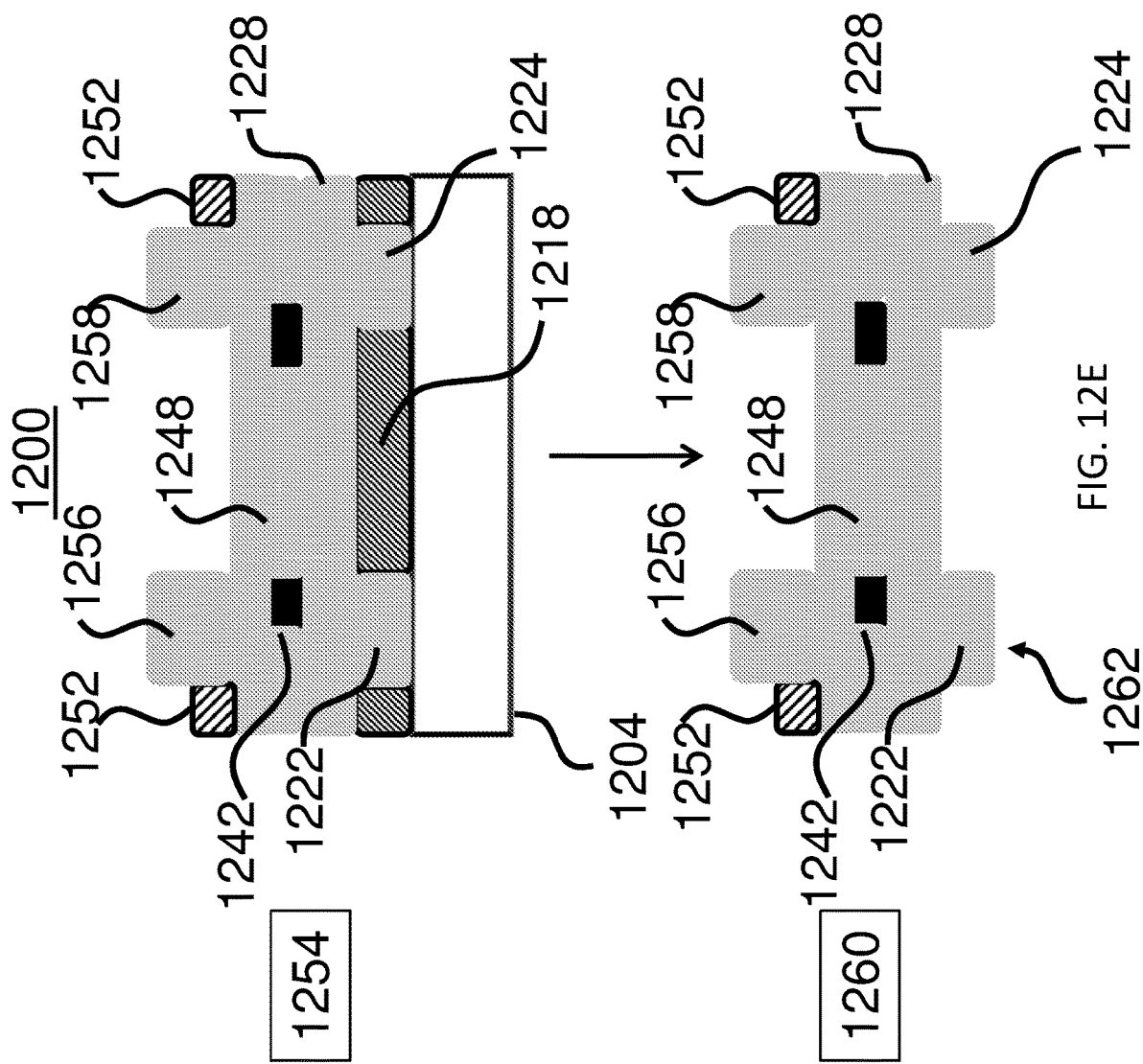

Beginning with FIG. 12A, at block 1202, sacrificial layer 1206 is deposited (e.g., by spin-coating) onto substrate 1204. In some embodiments, substrate 1204 may be a glass substrate. At block 1208, mask 1210 is applied, and sacrificial layer 1206 is exposed with UV light. UV light is applied through mask 1210, allowing UV light segments 1212 and 1214 to pass through and treat sacrificial layer 1206. At block 1216, after development of the structure through standard lithographic development, sacrificial layer 1206 is shaped into shaped sacrificial layer 1218 as a result of the masking of the UV treatment.

Process 1200 continues at block 1220 (FIG. 12B), where the masked holes in shaped sacrificial layer 1218 are filled with a substantially transparent polymer, creating columns 1222 and 1224. At block 1226, substantially transparent polymer layer 1228 is deposited over columns 1222 and 1224, as well as shaped sacrificial layer 1218.

Process 1200 continues at block 1230 (FIG. 12C), where magnetic layer 1232 is deposited over layer 1228. In some embodiments, magnetic layer 1232 includes nickel. In some embodiments, magnetic layer 1232 is deposited by sputtering. At block 1234, an etch-block layer is deposited over magnetic layer 1232, as represented by etch-blocks 1236 and 1238. At block 1240, the unblocked segments of magnetic layer 1232 are etched out, generated shaped magnetic layer 1242. In some embodiments, shaped magnetic layer 1242 may be shaped into a ring shape (with optional asymmetry for indication of orientation) surrounding a center portion of layer 1228 (see, e.g., layer 206 in FIG. 5A). At block 1244, the etch-block layer (as represented by etch-blocks 1236 and 1238) is removed.

Process 1200 continues at block 1246 (FIG. 12D), where substantially transparent polymer layer 1248 is deposited over layers 1228 and 1242 (filling in any holes in layer 1242 created by etch-blocking). At block 1250, substantially non-transparent layer 1252 is deposited and shaped by lithography on top of layer 1248. In some embodiments, layer 1252 is shaped with one or more gear teeth in a ring surrounding magnetic layer 1242 (see, e.g., layer 204 in relation to layers 202 and 206 and center portion 208 of FIG. 2A).

Process 1200 continues at block 1254 (FIG. 12E), where columns 1256 and 1258 are shaped by lithography on top of layer 1248. In some embodiments, columns 1256 and 1258 are made of a substantially transparent polymer. In some embodiments, the columns are positioned as shown in FIGS. 5A & 5B. At block 1260, substrate 1204 is cut into one or more beads of the same shape (i.e., although for simplicity of explanation only one bead is depicted in FIGS. 12A-12E, more than 1 bead may be constructed on substrate 1204 in process 1200). Also at block 1260, the entire structure (i.e., including 1204, 1218, 1222, 1224, 1228, 1242, 1248, 1252, 1256, and 1258) is immersed in a solvent. This solvent treatment dissolves sacrificial layer 1218 and releases bead 1262 from substrate 1204. In some embodiments, bead 1262 may be further modified, for example, by coupling a capture agent to one or both surfaces.

Figure 13A:
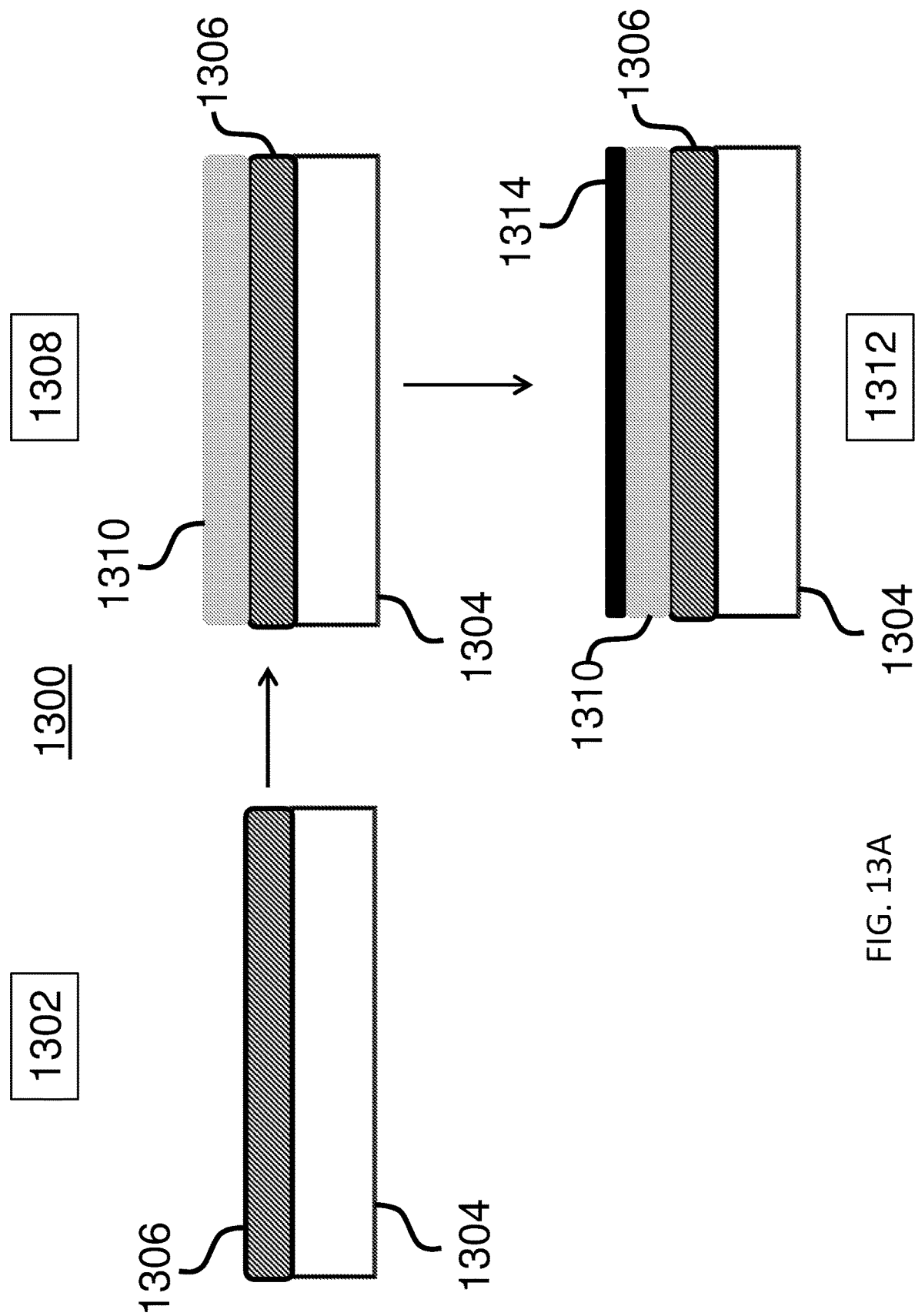
FIGS. 13A-13C show a method for producing an exemplary bead.
Figure 13B:
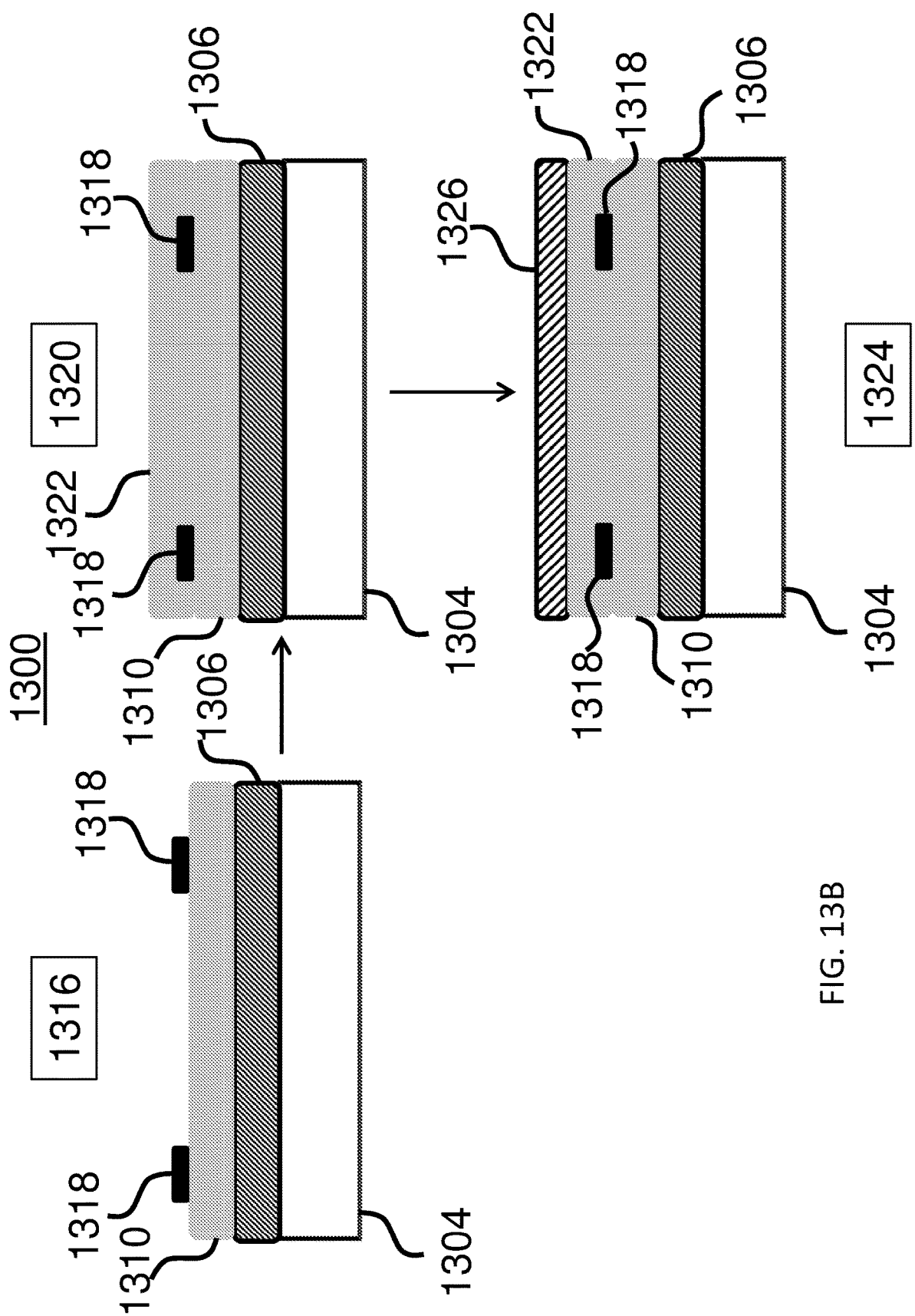
Figure 13C:
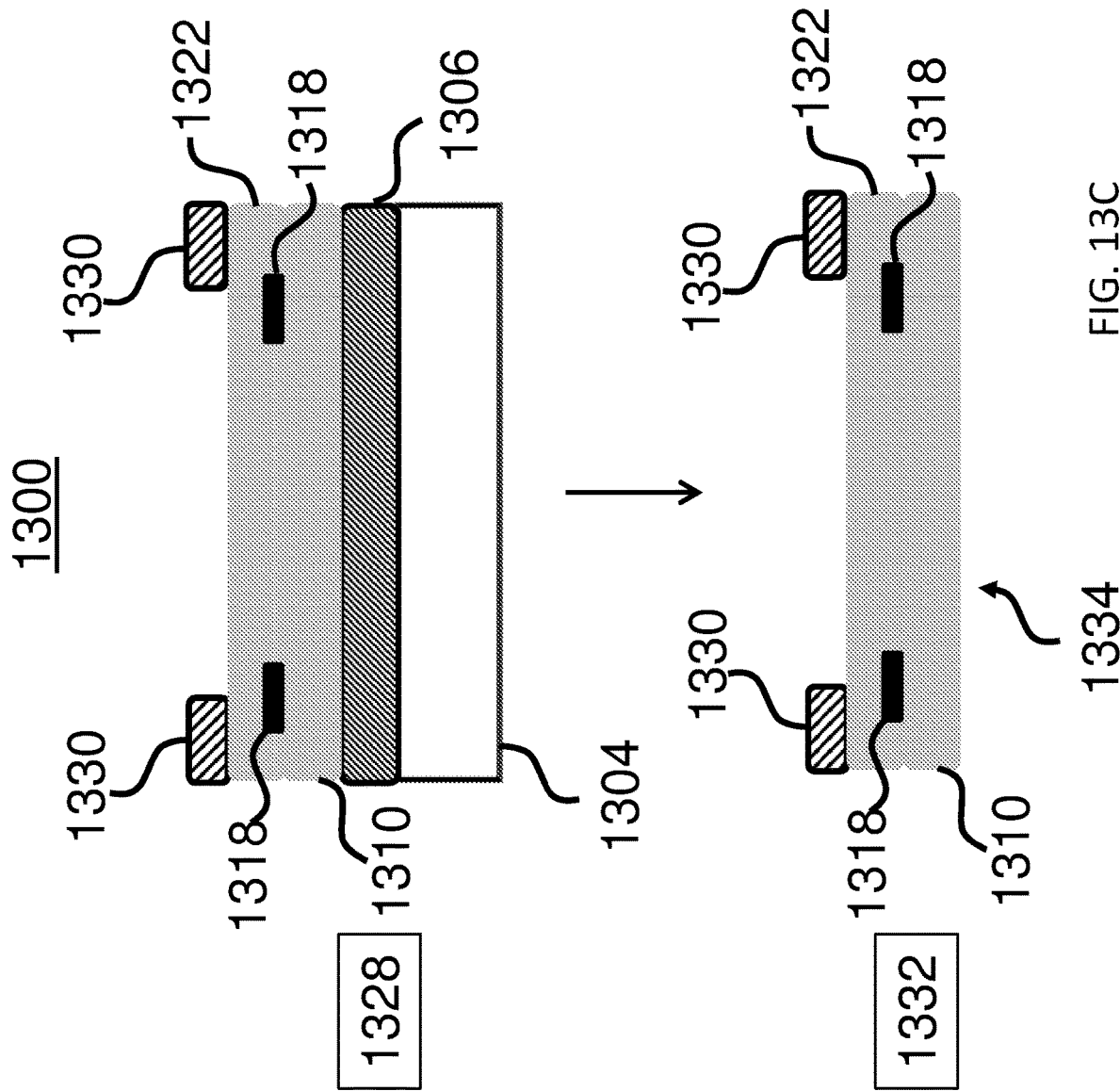

FIGS. 13A-13C illustrate process 1300, an exemplary workflow for generating a different type of multi-layer bead. Beginning with FIG. 13A, at block 1302, sacrificial layer 1306 is deposited on substrate layer 1304. In some embodiments, substrate 1304 is a glass substrate. At block 1308, substantially transparent layer 1310 is deposited over sacrificial layer 1306. At block 1312, magnetic layer 1314 is deposited over layer 1310. In some embodiments, magnetic layer 1314 includes nickel.

Process 1300 continues at block 1316 (FIG. 13B), where magnetic layer 1314 is defined into shaped magnetic layer 1318. In some embodiments, shaped magnetic layer 1318 is defined into a ring shape (with optional asymmetry for indication of orientation) surrounding a center portion of layer 1310 (see, e.g., layer 206 in FIG. 2A). At block 1320, substantially transparent layer 1322 is deposited over layers 1318 and 1310, filling in any holes created by defining shaped layer 1318. At block 1324, substantially non-transparent polymer layer 1326 is deposited over layer 1322.

Process 1300 continues at block 1328 (FIG. 13C), where substantially non-transparent polymer layer 1326 is shaped by lithography into gear-shaped substantially non-transparent polymer layer 1330. In some embodiments, layer 1330 is shaped with one or more gear teeth in a ring surrounding shaped magnetic layer 1318 (see, e.g., layer 204 in relation to layers 202 and 206 and center portion 208 of FIG. 2A). At block 1332, the entire structure (i.e., including 1304, 1306, 1310, 1318, 1322, and 1330) is immersed in a solvent. This solvent treatment dissolves sacrificial layer 1306 and releases bead 1334 from substrate 1304. In some embodiments, bead 1334 may be further modified, for example, by coupling a capture agent to one or both surfaces.

Example 5: An Assay Kit for a Multiplex Biological Assay

This example describes an exemplary assay kit for a multiplex biological assay using compositions of beads encoded with unique information-storing identifiers.
Materials and Methods
Bead Compositions A plurality of beads are functionalized and bound with two different capture agents: antibodies against each of tumor necrosis factor-alpha (TNF-α) and interleukin 6 (IL-6). The beads bound with antibodies against TNF-α are labeled with barcode 1011. The beads bound with antibodies against IL-6 are labeled with barcode 1012.

An additional plurality of beads are coated with biotinylated bovine serum albumin (BSA) and serve as the positive control. These beads comprise a barcode 3023 corresponding to the coating of biotinylated BSA, as well as to the identity of the assay kit ("Demo Kit").

An additional plurality of beads are coated with BSA and serve as the negative control. These beads comprise barcode 3024 or 3025 corresponding to the coating of BSA, as well as to the lot number PB031313-1 of the assay kit and the corresponding calibration data specific to the lot number.

An additional bead coated with BSA is labeled with a barcode 4013 corresponding to a particular patient ID 116707189.

An additional bead coated with BSA is labeled with a barcode 3080 corresponding to the research laboratory in which the assay was performed (PlexBio).
Reaction with Sample The pluralities of beads described above are added to a well (A2) containing a sample of serum spiked with TNF-α and IL-6. The mixture is then incubated at 37° C. for one hour. The sample is then washed with wash buffer (phosphate buffered saline containing 0.1% polysorbate 20 (Tween 20)). A biotin/secondary antibody solution is then added to the sample, containing biotinylated secondary antibodies capable of binding to TNF-α or IL-6 already bound with their primary antibodies. The sample is then incubated and washed with wash buffer. A solution containing streptavidin-phycoerythrin (PE) conjugate is then added and incubated with the bead mixture. The solution is then washed with wash buffer and a signal stabilizing solution to remove the excess fluorescent molecules.

Simultaneously, the pluralities of beads described above are added to eight other wells (A1, B1, C1, D1, E1, F1, G1, H1) containing known but different concentrations of TNF-α and IL-6, and the same assay process is carried out on these wells.

An imaging processor and reaction detection system are then used to simultaneously identify the barcode on each bead and detect the signal emitted from streptavidin-PE for all nine wells. A standard curve is determined for each of TNF-α and IL-6 using the identifications and signals detected from wells A1, B1, C1, D1, E1, F1, G1, H1, in combination with the known concentrations in each well. The median signal emitted by beads bound with the antibodies against TNF-α and IL-6 is then inputted into the standard curve for each of TNF-α and IL-6 to estimate the concentration of each in the sample.

Although the foregoing has been described in some detail by way of illustration and example for purposes of clarity of understanding, the descriptions and examples should not be construed as limiting the scope of the present disclosure. The disclosures of all patent and scientific literature cited herein are expressly incorporated in their entirety by reference.

What is claimed is:

1. A method for conducting a multiplex assay comprising the steps of:
 a) contacting a sample with beads in an assay system, wherein each bead in the system comprises
  (1) a substantially transparent polymer layer having a first surface and a second surface, the first and the second surfaces being parallel to each other;
  (2) a substantially non-transparent polymer layer, wherein the substantially non-transparent polymer layer is affixed to the first surface of the substantially transparent polymer layer and encloses a center portion of the substantially transparent polymer layer, wherein the substantially non-transparent polymer layer comprises one or more ring(s) enclosing the center portion of the substantially transparent polymer layer and represents an analog code, and wherein at least one of the one or more rings comprises a discontinuity;
 wherein the system comprises (i) at least one bead with an analog code that is recognized by an imaging processor as a specific assay, specific analyte, manufacturing lot, individual, locational identifier, or calibration signal and does not correspond to a capture agent associated with the at least one bead, and (ii) a plurality of beads, wherein each bead of the plurality of beads comprises a capture agent that specifically binds to an analyte, wherein the capture agent is immobilized on at least one of the first surface and the second surface of the substantially transparent polymer layer in at least the center portion of the substantially transparent polymer layer, and wherein each bead of the plurality of beads comprises an analog code corresponding to the capture agent; and
simultaneously or sequentially, in any order:
 b) identifying the analog code that is recognized by the imaging processor as the specific assay; and
 c) detecting the binding of the analyte in the sample by analyzing the binding of the analyte to the capture agent immobilized on the surface of the bead based on the identification of the analog code corresponding to the capture agent.

2. The method of claim 1, wherein the system further comprises (iii) at least two beads, at least three beads, at least four beads, at least five beads, or at least six beads, each with an analog code that is recognized by an imaging processor as a specific assay, specific analyte, manufacturing lot, individual, locational identifier, or calibration signal.

3. The method of claim 1, wherein the system further comprises (iv) at least one bead recognized by the imaging processor as a positive or negative control.

4. The method of claim 1, wherein the beads are less than about 300 μm in diameter.

5. The method of claim 1, wherein at least one surface of the bead comprises at least one site for chemical attachment of the capture agent.

6. The method of claim 1, wherein the capture agent is selected from the group consisting of: a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, and an antibody fragment.

7. The method of claim 1, wherein the plurality of beads are magnetic.

8. The method of claim 1, wherein the beads further comprise an orientation indicator for orienting the analog code of the substantially non-transparent polymer layer.

9. The method of claim 1, wherein the beads are less than about 50 μm in thickness.

10. The method of claim 1, wherein the analyte is selected from the group consisting of a DNA molecule, a DNA-analog-molecule, an RNA-molecule, an RNA-analog-molecule, a polynucleotide, a protein, an enzyme, a lipid, a phospholipid, a carbohydrate moiety, a polysaccharide, an antigen, a virus, a cell, an antibody, a small molecule, a bacterial cell, a cellular organelle, and an antibody fragment.

11. The method of claim 1, wherein the substantially transparent polymer layer comprises an epoxy-based polymer.

12. The method of claim 11, wherein the epoxy-based polymer is SU-8.

* * * * *